(12) United States Patent
Hansen et al.

(10) Patent No.: US 8,518,697 B2
(45) Date of Patent: Aug. 27, 2013

(54) SINGLE CHAIN TRIMERS AND USES THEREFOR

(75) Inventors: Ted Hansen, St. Louis, MO (US); Gerald Linette, St. Louis, MO (US); Michelle Becker-Hapak, St. Louis, MO (US)

(73) Assignee: Washington University, Saint Louis, MO (US)

( * ) Notice: Subject to any disclaimer, the term of this patent is extended or adjusted under 35 U.S.C. 154(b) by 503 days.

(21) Appl. No.: 12/691,489

(22) Filed: Jan. 21, 2010

(65) Prior Publication Data

US 2010/0159594 A1    Jun. 24, 2010

Related U.S. Application Data

(62) Division of application No. 11/397,377, filed on Apr. 4, 2006.

(51) Int. Cl.
| | | |
|---|---|---|
| *C12N 5/07* | (2010.01) | |
| *C12N 5/0783* | (2010.01) | |
| *A61K 39/00* | (2006.01) | |

(52) U.S. Cl.
USPC .......................................... 435/373; 435/375

(58) Field of Classification Search
None
See application file for complete search history.

(56) References Cited

U.S. PATENT DOCUMENTS

| | | | |
|---|---|---|---|
| 4,478,823 | A | 10/1984 | Sanderson |
| 5,468,481 | A | 11/1995 | Sharma et al. |
| 5,486,463 | A | 1/1996 | Lesslauer et al. |
| 5,492,813 | A | 2/1996 | Eisenbeis et al. |
| 5,733,550 | A | 3/1998 | Rock |
| 5,734,023 | A | 3/1998 | Nag et al. |
| 5,869,270 | A | 2/1999 | Rhode et al. |
| 5,976,551 | A | 11/1999 | Mottez et al. |
| 6,197,302 | B1 | 3/2001 | Hirsch et al. |
| 6,270,772 | B1 | 8/2001 | Burrows et al. |
| 6,309,645 | B1 | 10/2001 | Rhode et al. |
| 6,733,973 | B2 | 5/2004 | Diamond |
| 6,818,439 | B1 | 11/2004 | Jolly et al. |
| 2002/0198144 | A1 | 12/2002 | Wong et al. |
| 2003/0003535 | A1 | 1/2003 | Reiter |

FOREIGN PATENT DOCUMENTS

WO    WO 01/72768    10/2001

OTHER PUBLICATIONS

Knutson et al (Cancer Immunol. Immunother. 2006, 55: 96-103).*
Alexander et al., "Correlation Between CD8 Dependency and Determinant Density Using Peptide-Induced, Ld-Restricted Cytotoxic T Lymphocytes," J. Exp. Med., vol. 173, pp. 849-858, 1991.
Altman et al., "Phenotypic Analysis of Antigen-Specific T Lymphocytes," Science vol. 274, pp. 94-96, 1996.
Blattman et al., "Cancer Immunotherapy: A Treatment for the Masses," Science vol. 305, pp. 200-205, 2004.
Chung et al., "NK and CTL Recognition of a Single Chain H-2Dd Molecule: Distinct Sites of 2Dd Interact with NK and TCR," The Journal of Immunology, vol. 163, pp. 3699-3708, 1999.
Harris et al., "Interactions of HLA-B27 With the Peptide Loading Complex as Revealed by Heavy Chain Mutations," International Immunology, vol. 13, pp. 1275-1282, 2001.
Hennecke et al., "Structure of a Covalently Stabilized Complex of a Human a•T-Cell Receptor, Influenza HA Peptide and MHC Class II Molecule, HLA-DR1," The EMBO Journal, vol. 19, pp. 5611-5624, 2000.
Hogquist et al., "T Cell Receptor Antagonist Peptides Induce Positive Selection," Cell, vol. 76, pp. 17-27,1994.
Ignatowicz et al., "The Repertoire of T Cells Shaped by a Single MHC/Peptide Ligand," Cell, vol. 84, pp. 521-529, 1996.
Kohler et al., "Continuous cultures of fused cells secreting antibody of predefined specificity." Nature, vol. 256, pp. 495-497, 1975.
Kohler et al., "Derivation of Specific Antibody-Producing Tissue Culture and Tumor Lines by Cell Fusion," Eur. J. Immunol. vol. 6, pp. 511-519, 1976.
Kohler et al., "Fusion between immunoglobulin secreting and nonsecreting myeloma cell lines," Eur. J. Immunol. vol. 6, pp. 292-295, 1976.
Lybarger et al., "Enhanced immune presentation of a single-chain major histocompatibility complex class I molecule engineered to optimize linkage of a C-terminally extended peptide." J. Biol. Chem., vol. 278, pp. 27105-27111, 2003.
Lybarger et al., "Tapasin Enhances Peptide-Induced Expression of H2-M3 Molecules, But is Not Required for the Retention of Open Conformers," The Journal of Immunology, vol. 167, pp. 2097-2105, 2001.
Mage et al., "A Recombinant, Soluble, Single-Chain Class I Major Histocompatibility Complex Molecule with Biological Activity," Proc. Natl. Acad. Sci. USA, vol. 89, pp. 10658-10662, 1992.
Mottez et al., "Cells Expressing a Major Histocompatibility Complex Class I Molecule with a Single Covalently Bound Peptide Are Highly Immunogenic," J.Exp. Med., vol. 181, pp. 493-502, 1995.
Oosten et al., "Artificial antigen-presenting constructs efficiently stimulate minor histocompatibility antigen—specific cytotoxic T lymphocytes," Blood 104:224-226, 2004.

(Continued)

*Primary Examiner* — Gerald R Ewoldt
*Assistant Examiner* — Marianne Dibrino
(74) *Attorney, Agent, or Firm* — Zackson Law LLC; Saul L. Zackson

(57) ABSTRACT

Single chain trimer (SCT) molecules are disclosed, comprising an MHC antigen peptide sequence, a $\beta_2$-microglobulin sequence and a full-length MHC class I heavy chain sequence, joined by linker sequences. Further described are nucleic acids encoding single chain trimers. Methods for expansion of antigen-specific T cell populations using single chain trimer molecules are also disclosed. In some configurations, these methods comprise co-culturing, in a first stage, CD8+ T cells from a donor with antigen presenting cells comprising an MHC antigen peptide, and co-culturing, in a second stage, the CD8+ T cells with cells comprising an SCT which has an MHC antigen peptide sequence identical to the sequence of the antigen peptide in the first stage. The methods can provide 10,000-100,000 fold expansion of antigen-specific CD8+ T cells within about 28 days after establishing culture, and can yield over 1 billion antigen-specific CD8+ T cells expanded from an individual donor.

12 Claims, 18 Drawing Sheets

(56) References Cited

OTHER PUBLICATIONS

Reddehase et al., "A Pentapeptide as Minimal Antigenic Determinant for MHC Class I-Restricted T Lymphocytes," Nature, vol. 337, pp. 651-653, 1989.

Schumacher et al., "Peptide Selection by MHC Class I Molecules," Nature, vol. 350, pp. 703-706, 1991.

Smith et al., "Model for the in Vivo Assembly of Nascent Ld Class I Molecules and for the Expression of Unfolded LD Molecules at the Cell Surface," J.Exp.Med., vol. 178, pp. 2035-2046, 1993.

Smith et al., "Disparate Interaction of Peptide Ligand with Nascent Versus Mature Class I Major Histocompatibility Complex Molecules: Comparisons of Peptide Binding to Alternative Forms of Ld in Cell Lysates and the Cell Surface," J.Exp. Med., vol. 175, pp. 191-202, 1992.

Suri et al., "Specificity of peptide selection by antigen-presenting cells homozygous or heterozygous for expression of class II MHC molecules: The lack of competition," Proc. Natl. Acad. Sci. USA vol. 100, pp. 5330-5335, 2003.

Toshitani et al., "Expression of a Single-Chain HLA Class I Molecule in a Human Cell Line: Presentation of Exogenous Peptide and Processed Antigen to Cytotoxic T Lymphocytes," Proc. Natl. Acad. Sci. USA, vol. 93, pp. 236-240, 1996.

Udaka et al., "A Naturally Occurring Peptide Recognized by Alloreactive CD8+ Cytotoxic T Lymphocytes in Association with a Class I MHC Protein," Cell, vol. 69, pp. 989-998, 1992.

Uger et al.., "Creating CTL Targets with Epitope-Linked β2-Microglobulin Constructs," The Journal of Immunology, vol. 160, pp. 1598-1605, 1998.

Uger, et al, "Covalent Linkage to β2-Microglobulin Enhances the MHC Stability and Antigenicity of Suboptimal CTL Epitopes," The Journal of Immunology, vol. 162, pp. 6024-6028, 1999.

White et al., "Soluble class I MHC with beta2-microglobulin covalently linked peptides: specific binding to a T cell hybridoma," J Immunol 162:2671-2676, 1999.

York et al., "A Cytosolic Herpes Simplex Virus Protein Inhibits Antigen Presentation to CD8+ T Lymphocytes," Cell, vol. 77, pp. 525-535, 1994.

Yu et al., "Cutting Edge: Single-Chain Trimers of MHC Class I Molecules Form Stable Structures That Potently Stimulate Antigen-Specific T Cells and B Cells," J. Immunol. 168:3145-3149, 2002.

Yu et al., "Definition and Transfer of a Serological Epitope Specific for Peptide-Empty Forms of MHC Class I," International Immunology, vol. 11, pp. 1897-1905, 1999.

Zijlstra et al., "β2-Microglobulin Deficient Mice Lack CD4 8+ Cytolytic T Cells," Nature, vol. 344, pp. 742-746, 1990.

Long et al., "Efficient cDNA expression vectors for stable and transient expression of HLA-DR in transfected fibroblast and lymphoid cells." (Abstract) Hum. Immunol. Aug. 1991;31(4):229.

Carbone et al., "Induction of Ovalbumin-Specific Cytotoxic T Cells by in Vivo Peptide Immunization," J. Exp. Med., vol. 169, pp. 603-612, 1989.

Gattinoni et al., "Acquisition of full effector function in vitro paradoxically impairs the in vivo antitumor efficacy of adoptively transferred CD8+ T cells," J. Clin. Inv., vol. 115, pp. 1616-1626, 2005.

Myers et al., "Kb, Kd, and Ld Molecules Share Common Tapasin Dependencies as Determined Using a Novel Epitope Tag," The Journal of Immunology, vol. 165, pp. 5656-5663, 2000.

* cited by examiner

FIG. 7

AlignX Amino Acid Alignment of Example SCT's

```
                     1                                                  50
     CMV SCT     (1) MARSVTLVFLVLVSLTGLYANLVPMVATVGGGASGGGGSGGGGSIQRTPK
EBV BMLF1 SCT    (1) MARSVTLVFLVLVSLTGLYAGLCTLVAMLGGGASGGGGSGGGGSIQRTPK
    fluM1 SCT    (1) MARSVTLVFLVLVSLTGLYAGILGFVFTLGGGASGGGGSGGGGSIQRTPK
  G209-2M SCT    (1) MARSVTLVFLVLVSLTGLYAIMDQVPFSVGGGASGGGGSGGGGSIQRTPK
  G280-9V SCT    (1) MARSVTLVFLVLVSLTGLYAYLEPGPVTVGGGASGGGGSGGGGSIQRTPK
    Consensus    (1) MARSVTLVFLVLVSLTGLYA L  LV  TVGGGASGGGGSGGGGSIQRTPK 51                                                 100
     CMV SCT    (51) IQVYSRHPAENGKSNFLNCYVSGFHPSDIEVDLLKNGERIEKVEHSDLSF
EBV BMLF1 SCT   (51) IQVYSRHPAENGKSNFLNCYVSGFHPSDIEVDLLKNGERIEKVEHSDLSF
    fluM1 SCT   (51) IQVYSRHPAENGKSNFLNCYVSGFHPSDIEVDLLKNGERIEKVEHSDLSF
  G209-2M SCT   (51) IQVYSRHPAENGKSNFLNCYVSGFHPSDIEVDLLKNGERIEKVEHSDLSF
  G280-9V SCT   (51) IQVYSRHPAENGKSNFLNCYVSGFHPSDIEVDLLKNGERIEKVEHSDLSF
    Consensus   (51) IQVYSRHPAENGKSNFLNCYVSGFHPSDIEVDLLKNGERIEKVEHSDLSF 101                                                 150
     CMV SCT   (101) SKDWSFYLLYYTEFTPTEKDEYACRVNHVTLSQPKIVKWDRDMGGGGSGG
EBV BMLF1 SCT  (101) SKDWSFYLLYYTEFTPTEKDEYACRVNHVTLSQPKIVKWDRDMGGGGSGG
    fluM1 SCT  (101) SKDWSFYLLYYTEFTPTEKDEYACRVNHVTLSQPKIVKWDRDMGGGGSGG
  G209-2M SCT  (101) SKDWSFYLLYYTEFTPTEKDEYACRVNHVTLSQPKIVKWDRDMGGGGSGG
  G280-9V SCT  (101) SKDWSFYLLYYTEFTPTEKDEYACRVNHVTLSQPKIVKWDRDMGGGGSGG
    Consensus  (101) SKDWSFYLLYYTEFTPTEKDEYACRVNHVTLSQPKIVKWDRDMGGGGSGG 151                                                 200
     CMV SCT   (151) GGSGGGGSGGGGSGSHSMRYFFTSVSRPGRGEPRFIAVGYVDDTQFVRFD
EBV BMLF1 SCT  (151) GGSGGGGSGGGGSGSHSMRYFFTSVSRPGRGEPRFIAVGYVDDTQFVRFD
    fluM1 SCT  (151) GGSGGGGSGGGGSGSHSMRYFFTSVSRPGRGEPRFIAVGYVDDTQFVRFD
  G209-2M SCT  (151) GGSGGGGSGGGGSGSHSMRYFFTSVSRPGRGEPRFIAVGYVDDTQFVRFD
  G280-9V SCT  (151) GGSGGGGSGGGGSGSHSMRYFFTSVSRPGRGEPRFIAVGYVDDTQFVRFD
    Consensus  (151) GGSGGGGSGGGGSGSHSMRYFFTSVSRPGRGEPRFIAVGYVDDTQFVRFD 201                                                 250
     CMV SCT   (201) SDAASQRMEPRAPWIEQEGPEYWDGETRKVKAHSQTHRVDLGTLRGYYNQ
EBV BMLF1 SCT  (201) SDAASQRMEPRAPWIEQEGPEYWDGETRKVKAHSQTHRVDLGTLRGYYNQ
    fluM1 SCT  (201) SDAASQRMEPRAPWIEQEGPEYWDGETRKVKAHSQTHRVDLGTLRGYYNQ
  G209-2M SCT  (201) SDAASQRMEPRAPWIEQEGPEYWDGETRKVKAHSQTHRVDLGTLRGYYNQ
  G280-9V SCT  (201) SDAASQRMEPRAPWIEQEGPEYWDGETRKVKAHSQTHRVDLGTLRGYYNQ
    Consensus  (201) SDAASQRMEPRAPWIEQEGPEYWDGETRKVKAHSQTHRVDLGTLRGYYNQ 251                                                 300
     CMV SCT   (251) SEAGSHTVQRMYGCDVGSDWRFLRGYHQYAYDGKDYIALKEDLRSWTAAD
EBV BMLF1 SCT  (251) SEAGSHTVQRMYGCDVGSDWRFLRGYHQYAYDGKDYIALKEDLRSWTAAD
    fluM1 SCT  (251) SEAGSHTVQRMYGCDVGSDWRFLRGYHQYAYDGKDYIALKEDLRSWTAAD
  G209-2M SCT  (251) SEAGSHTVQRMYGCDVGSDWRFLRGYHQYAYDGKDYIALKEDLRSWTAAD
  G280-9V SCT  (251) SEAGSHTVQRMYGCDVGSDWRFLRGYHQYAYDGKDYIALKEDLRSWTAAD
    Consensus  (251) SEAGSHTVQRMYGCDVGSDWRFLRGYHQYAYDGKDYIALKEDLRSWTAAD
```

FIG.7 Continued

```
                     301                                                350
      CMV SCT  (301) MAAQTTKHKWEAAHVAEQLRAYLEGTCVEWLRRYLENGKETLQRTDAPKT
EBV BMLF1 SCT  (301) MAAQTTKHKWEAAHVAEQLRAYLEGTCVEWLRRYLENGKETLQRTDAPKT
     fluM1 SCT (301) MAAQTTKHKWEAAHVAEQLRAYLEGTCVEWLRRYLENGKETLQRTDAPKT
    G209-2M SCT (301) MAAQTTKHKWEAAHVAEQLRAYLEGTCVEWLRRYLENGKETLQRTDAPKT
    G280-9V SCT (301) MAAQTTKHKWEAAHVAEQLRAYLEGTCVEWLRRYLENGKETLQRTDAPKT
    Consensus  (301) MAAQTTKHKWEAAHVAEQLRAYLEGTCVEWLRRYLENGKETLQRTDAPKT 351                                                400
      CMV SCT  (351) HMTHHAVSDHEATLRCWALSFYPAEITLTWQRDGEDQTQDTELVETRPAG
EBV BMLF1 SCT  (351) HMTHHAVSDHEATLRCWALSFYPAEITLTWQRDGEDQTQDTELVETRPAG
     fluM1 SCT (351) HMTHHAVSDHEATLRCWALSFYPAEITLTWQRDGEDQTQDTELVETRPAG
    G209-2M SCT (351) HMTHHAVSDHEATLRCWALSFYPAEITLTWQRDGEDQTQDTELVETRPAG
    G280-9V SCT (351) HMTHHAVSDHEATLRCWALSFYPAEITLTWQRDGEDQTQDTELVETRPAG
    Consensus  (351) HMTHHAVSDHEATLRCWALSFYPAEITLTWQRDGEDQTQDTELVETRPAG 401                                                450
      CMV SCT  (401) DGTFQKWAAVVVPSGQEQRYTCHVQHEGLPKPLTLRWEPSSQPTIPIVGI
EBV BMLF1 SCT  (401) DGTFQKWAAVVVPSGQEQRYTCHVQHEGLPKPLTLRWEPSSQPTIPIVGI
     fluM1 SCT (401) DGTFQKWAAVVVPSGQEQRYTCHVQHEGLPKPLTLRWEPSSQPTIPIVGI
    G209-2M SCT (401) DGTFQKWAAVVVPSGQEQRYTCHVQHEGLPKPLTLRWEPSSQPTIPIVGI
    G280-9V SCT (401) DGTFQKWAAVVVPSGQEQRYTCHVQHEGLPKPLTLRWEPSSQPTIPIVGI
    Consensus  (401) DGTFQKWAAVVVPSGQEQRYTCHVQHEGLPKPLTLRWEPSSQPTIPIVGI 451                                                500
      CMV SCT  (451) IAGLVLFGAVITGAVVAAVMWRRKSSDRKGGSYSQAASSDSAQGSDVSLT
EBV BMLF1 SCT  (451) IAGLVLFGAVITGAVVAAVMWRRKSSDRKGGSYSQAASSDSAQGSDVSLT
     fluM1 SCT (451) IAGLVLFGAVITGAVVAAVMWRRKSSDRKGGSYSQAASSDSAQGSDVSLT
    G209-2M SCT (451) IAGLVLFGAVITGAVVAAVMWRRKSSDRKGGSYSQAASSDSAQGSDVSLT
    G280-9V SCT (451) IAGLVLFGAVITGAVVAAVMWRRKSSDRKGGSYSQAASSDSAQGSDVSLT
    Consensus  (451) IAGLVLFGAVITGAVVAAVMWRRKSSDRKGGSYSQAASSDSAQGSDVSLT 501
      CMV SCT  (501) ACKV-   (SEQ ID NO: 21)
EBV BMLF1 SCT  (501) ACKV-   (SEQ ID NO: 22)
     fluM1 SCT (501) ACKV-   (SEQ ID NO: 23)
    G209-2M SCT (501) ACKV-   (SEQ ID NO: 24)
    G280-9V SCT (501) ACKV-   (SEQ ID NO: 25)
    Consensus  (501) ACKV    (SEQ ID NO: 26)
```

FIG. 12A
Control Mice
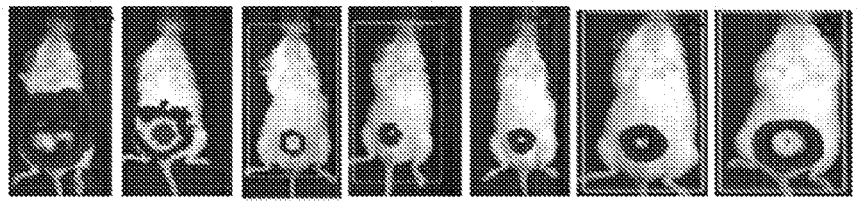
B1
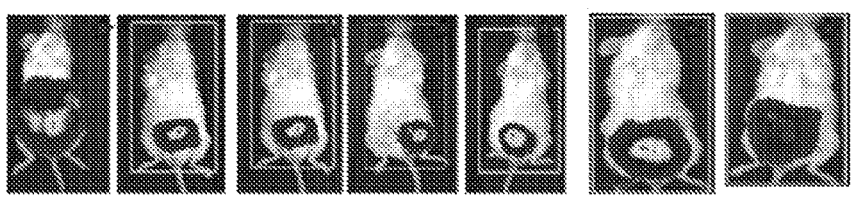
B2
Experimental mice
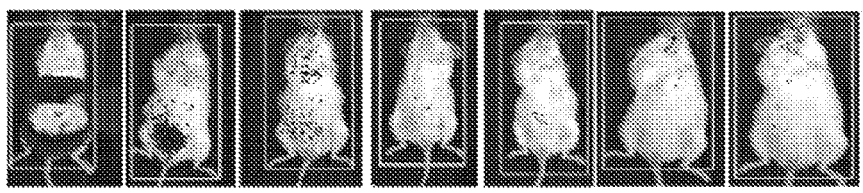
A1
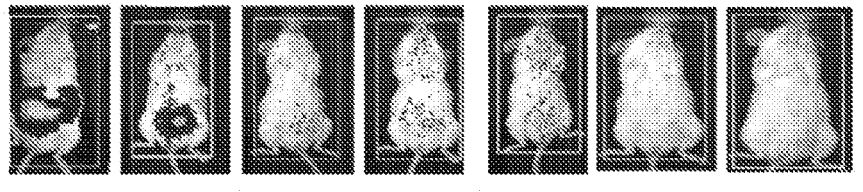
A2
A3

SEQUENCE LISTING

```
<160> NUMBER OF SEQ ID NOS: 42

<210> SEQ ID NO 1
<211> LENGTH: 9
<212> TYPE: PRT
<213> ORGANISM: Artificial
<220> FEATURE:
<223> OTHER INFORMATION: Cytomegalovirus

<400> SEQUENCE: 1

Asn Leu Val Pro Met Val Ala Thr Val
1               5

<210> SEQ ID NO 2
<211> LENGTH: 9
<212> TYPE: PRT
<213> ORGANISM: Artificial
<220> FEATURE:
<223> OTHER INFORMATION: Epstein-Barr virus

<400> SEQUENCE: 2

Gly Leu Cys Thr Leu Val Ala Met Leu
1               5

<210> SEQ ID NO 3
<211> LENGTH: 9
<212> TYPE: PRT
<213> ORGANISM: Influenza A virus

<400> SEQUENCE: 3
```

```
Gly Ile Leu Gly Phe Val Phe Thr Leu
 1               5
```

<210> SEQ ID NO 4
<211> LENGTH: 9
<212> TYPE: PRT
<213> ORGANISM: Homo sapiens

<400> SEQUENCE: 4

```
Ile Met Asp Gln Val Pro Phe Ser Val
 1               5
```

<210> SEQ ID NO 5
<211> LENGTH: 9
<212> TYPE: PRT
<213> ORGANISM: Homo sapiens

<400> SEQUENCE: 5

```
Tyr Leu Glu Pro Gly Pro Val Thr Val
 1               5
```

<210> SEQ ID NO 6
<211> LENGTH: 99
<212> TYPE: PRT
<213> ORGANISM: Homo sapiens

<400> SEQUENCE: 6

```
Ile Gln Arg Thr Pro Lys Ile Gln Val Tyr Ser Arg His Pro Ala Glu
 1               5                  10                  15

Asn Gly Lys Ser Asn Phe Leu Asn Cys Tyr Val Ser Gly Phe His Pro
                20                  25                  30

Ser Asp Ile Glu Val Asp Leu Leu Lys Asn Gly Glu Arg Ile Glu Lys
            35                  40                  45

Val Glu His Ser Asp Leu Ser Phe Ser Lys Asp Trp Ser Phe Tyr Leu
        50                  55                  60

Leu Tyr Tyr Thr Glu Phe Thr Pro Thr Glu Lys Asp Glu Tyr Ala Cys
 65                  70                  75                  80

Arg Val Asn His Val Thr Leu Ser Gln Pro Lys Ile Val Lys Trp Asp
                85                  90                  95

Arg Asp Met
```

<210> SEQ ID NO 7
<211> LENGTH: 341
<212> TYPE: PRT
<213> ORGANISM: Homo sapiens

<400> SEQUENCE: 7

```
Gly Ser His Ser Met Arg Tyr Phe Phe Thr Ser Val Ser Arg Pro Gly
 1               5                  10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Gly Glu Thr
        50                  55                  60

Arg Lys Val Lys Ala His Ser Gln Thr His Arg Val Asp Leu Gly Thr
 65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
```

-continued

```
                100              105              110
Tyr His Gln Tyr Ala Tyr Asp Gly Lys Asp Tyr Ile Ala Leu Lys Glu
            115                  120                  125

Asp Leu Arg Ser Trp Thr Ala Ala Asp Met Ala Ala Gln Thr Thr Lys
        130                  135                  140

His Lys Trp Glu Ala Ala His Val Ala Glu Gln Leu Arg Ala Tyr Leu
145                  150                  155                  160

Glu Gly Thr Cys Val Glu Trp Leu Arg Arg Tyr Leu Glu Asn Gly Lys
                    165                  170                  175

Glu Thr Leu Gln Arg Thr Asp Ala Pro Lys Thr His Met Thr His His
            180                  185                  190

Ala Val Ser Asp His Glu Ala Thr Leu Arg Cys Trp Ala Leu Ser Phe
        195                  200                  205

Tyr Pro Ala Glu Ile Thr Leu Thr Trp Gln Arg Asp Gly Glu Asp Gln
            210                  215                  220

Thr Gln Asp Thr Glu Leu Val Glu Thr Arg Pro Ala Gly Asp Gly Thr
225                  230                  235                  240

Phe Gln Lys Trp Ala Ala Val Val Val Pro Ser Gly Gln Glu Gln Arg
                    245                  250                  255

Tyr Thr Cys His Val Gln His Glu Gly Leu Pro Lys Pro Leu Thr Leu
            260                  265                  270

Arg Trp Glu Pro Ser Ser Gln Pro Thr Ile Pro Ile Val Gly Ile Ile
        275                  280                  285

Ala Gly Leu Val Leu Phe Gly Ala Val Ile Thr Gly Ala Val Val Ala
            290                  295                  300

Ala Val Met Trp Arg Arg Lys Ser Ser Asp Arg Lys Gly Gly Ser Tyr
305                  310                  315                  320

Ser Gln Ala Ala Ser Ser Asp Ser Ala Gln Gly Ser Asp Val Ser Leu
                    325                  330                  335

Thr Ala Cys Lys Val
            340
```

<210> SEQ ID NO 8
<211> LENGTH: 341
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (84)..(84)
<223> OTHER INFORMATION: X: substitution of tyr-84 with a non-aromatic
      amino acid other than proline

<400> SEQUENCE: 8

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Xaa Tyr Asn Gln Ser Glu Ala Gly Ser His Thr Val Gln
                85                  90                  95
```

```
Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
            115                 120                 125

Asp Leu Arg Ser Trp Thr Ala Asp Met Ala Gln Thr Thr Lys
130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
            195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
            275                 280                 285

Ala Gly Leu Val Leu Phe Gly Ala Val Ile Thr Gly Ala Val Val Ala
            290                 295                 300

Ala Val Met Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala Cys Lys Val
            340

<210> SEQ ID NO 9
<211> LENGTH: 341
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (84)..(84)
<223> OTHER INFORMATION: Tyr-84 substituted with alanine

<400> SEQUENCE: 9

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Ala Tyr Asn Gln Ser Glu Ala Gly Ser His Thr Val Gln
                85                  90                  95
```

```
Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
            115                 120                 125

Asp Leu Arg Ser Trp Thr Ala Ala Asp Met Ala Ala Gln Thr Thr Lys
        130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Ile Thr Gly Ala Val Val Ala
        290                 295                 300

Ala Val Met Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala Cys Lys Val
            340

<210> SEQ ID NO 10
<211> LENGTH: 20
<212> TYPE: PRT
<213> ORGANISM: Mus musculus

<400> SEQUENCE: 10

Met Ala Arg Ser Val Thr Leu Val Phe Leu Val Leu Val Ser Leu Thr
1               5                   10                  15

Gly Leu Tyr Ala
            20

<210> SEQ ID NO 11
<211> LENGTH: 10
<212> TYPE: PRT
<213> ORGANISM: Artificial
<220> FEATURE:
<223> OTHER INFORMATION: Synthetic

<400> SEQUENCE: 11

Gly Gly Gly Gly Ser Gly Gly Gly Gly Ser
1               5                   10

<210> SEQ ID NO 12
<211> LENGTH: 15
<212> TYPE: PRT
<213> ORGANISM: Artificial
```

```
-continued

<220> FEATURE:
<223> OTHER INFORMATION: Synthetic

<400> SEQUENCE: 12

Gly Gly Gly Ala Ser Gly Gly Gly Ser Gly Gly Gly Gly Ser
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthetic

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 20
<212> TYPE: PRT
<213> ORGANISM: Artificial
<220> FEATURE:
<223> OTHER INFORMATION: Synthetic

<400> SEQUENCE: 14

Gly Gly Gly Gly Ser Gly Gly Gly Gly Ser Gly Gly Gly Gly Ser Gly
1               5                   10                  15

Gly Gly Gly Ser
            20

<210> SEQ ID NO 15
<211> LENGTH: 504
<212> TYPE: PRT
<213> ORGANISM: Artificial
<220> FEATURE:
<223> OTHER INFORMATION: Synthetic; sequence comprising antigen peptide
      sequence, beta2-microglobulin sequence and human MHC class I heavy
      chain sequence
<220> FEATURE:
<221> NAME/KEY: PEPTIDE
<222> LOCATION: (21)..(29)
<223> OTHER INFORMATION: Antigen peptide sequence

<400> SEQUENCE: 15

Met Ala Arg Ser Val Thr Leu Val Phe Leu Val Leu Val Ser Leu Thr
1               5                   10                  15

Gly Leu Tyr Ala Xaa Xaa Xaa Xaa Xaa Xaa Xaa Xaa Xaa Gly Gly Gly
            20                  25                  30

Ala Ser Gly Gly Gly Gly Ser Gly Gly Gly Gly Ser Ile Gln Arg Thr
        35                  40                  45

Pro Lys Ile Gln Val Tyr Ser Arg His Pro Ala Glu Asn Gly Lys Ser
    50                  55                  60

Asn Phe Leu Asn Cys Tyr Val Ser Gly Phe His Pro Ser Asp Ile Glu
65                  70                  75                  80

Val Asp Leu Leu Lys Asn Gly Glu Arg Ile Glu Lys Val Glu His Ser
                85                  90                  95

Asp Leu Ser Phe Ser Lys Asp Trp Ser Phe Tyr Leu Leu Tyr Tyr Thr
            100                 105                 110

Glu Phe Thr Pro Thr Glu Lys Asp Glu Tyr Ala Cys Arg Val Asn His
        115                 120                 125

Val Thr Leu Ser Gln Pro Lys Ile Val Lys Trp Asp Arg Asp Met Gly
    130                 135                 140
```

Gly Gly Gly Ser Gly Gly Gly Ser Gly Gly Gly Ser Gly Gly
145                 150                 155                 160

Gly Gly Ser Gly Ser His Ser Met Arg Tyr Phe Phe Thr Ser Val Ser
            165                 170                 175

Arg Pro Gly Arg Gly Glu Pro Arg Phe Ile Ala Val Gly Tyr Val Asp
            180                 185                 190

Asp Thr Gln Phe Val Arg Phe Asp Ser Asp Ala Ala Ser Gln Arg Met
            195                 200                 205

Glu Pro Arg Ala Pro Trp Ile Glu Gln Glu Gly Pro Glu Tyr Trp Asp
210                 215                 220

Gly Glu Thr Arg Lys Val Lys Ala His Ser Gln Thr His Arg Val Asp
225                 230                 235                 240

Leu Gly Thr Leu Arg Gly Tyr Tyr Asn Gln Ser Glu Ala Gly Ser His
            245                 250                 255

Thr Val Gln Arg Met Tyr Gly Cys Asp Val Gly Ser Asp Trp Arg Phe
            260                 265                 270

Leu Arg Gly Tyr His Gln Tyr Ala Tyr Asp Gly Lys Asp Tyr Ile Ala
            275                 280                 285

Leu Lys Glu Asp Leu Arg Ser Trp Thr Ala Ala Asp Met Ala Ala Gln
290                 295                 300

Thr Thr Lys His Lys Trp Glu Ala Ala His Val Ala Glu Gln Leu Arg
305                 310                 315                 320

Ala Tyr Leu Glu Gly Thr Cys Val Glu Trp Leu Arg Arg Tyr Leu Glu
            325                 330                 335

Asn Gly Lys Glu Thr Leu Gln Arg Thr Asp Ala Pro Lys Thr His Met
            340                 345                 350

Thr His His Ala Val Ser Asp His Glu Ala Thr Leu Arg Cys Trp Ala
            355                 360                 365

Leu Ser Phe Tyr Pro Ala Glu Ile Thr Leu Thr Trp Gln Arg Asp Gly
370                 375                 380

Glu Asp Gln Thr Gln Asp Thr Glu Leu Val Glu Thr Arg Pro Ala Gly
385                 390                 395                 400

Asp Gly Thr Phe Gln Lys Trp Ala Ala Val Val Val Pro Ser Gly Gln
            405                 410                 415

Glu Gln Arg Tyr Thr Cys His Val Gln His Glu Gly Leu Pro Lys Pro
            420                 425                 430

Leu Thr Leu Arg Trp Glu Pro Ser Ser Gln Pro Thr Ile Pro Ile Val
            435                 440                 445

Gly Ile Ile Ala Gly Leu Val Leu Phe Gly Ala Val Ile Thr Gly Ala
450                 455                 460

Val Val Ala Ala Val Met Trp Arg Arg Lys Ser Ser Asp Arg Lys Gly
465                 470                 475                 480

Gly Ser Tyr Ser Gln Ala Ala Ser Ser Asp Ser Ala Gln Gly Ser Asp
            485                 490                 495

Val Ser Leu Thr Ala Cys Lys Val
            500

<210> SEQ ID NO 16
<211> LENGTH: 504
<212> TYPE: PRT
<213> ORGANISM: Artificial
<220> FEATURE:
<223> OTHER INFORMATION: Synthetic; sequence comprising antigen peptide
      sequence, beta2-microglobulin sequence and human MHC class I heavy
      chain sequence
<220> FEATURE:
<221> NAME/KEY: PEPTIDE

```
<222> LOCATION: (21)..(29)
<223> OTHER INFORMATION: Antigen peptide sequence
<220> FEATURE:
<221> NAME/KEY: MISC_FEATURE
<222> LOCATION: (247)..(247)
<223> OTHER INFORMATION: X: amino acid substitution for tyr-247

<400> SEQUENCE: 16

Met Ala Arg Ser Val Thr Leu Val Phe Leu Val Leu Val Ser Leu Thr
1               5                   10                  15

Gly Leu Tyr Ala Xaa Xaa Xaa Xaa Xaa Xaa Xaa Gly Gly Gly
            20                  25                  30

Ala Ser Gly Gly Gly Ser Gly Gly Gly Ser Ile Gln Arg Thr
        35                  40                  45

Pro Lys Ile Gln Val Tyr Ser Arg His Pro Ala Glu Asn Gly Lys Ser
50                  55                  60

Asn Phe Leu Asn Cys Tyr Val Ser Gly Phe His Pro Ser Asp Ile Glu
65                  70                  75                  80

Val Asp Leu Leu Lys Asn Gly Glu Arg Ile Glu Lys Val Glu His Ser
                85                  90                  95

Asp Leu Ser Phe Ser Lys Asp Trp Ser Phe Tyr Leu Leu Tyr Tyr Thr
                100                 105                 110

Glu Phe Thr Pro Thr Glu Lys Asp Glu Tyr Ala Cys Arg Val Asn His
            115                 120                 125

Val Thr Leu Ser Gln Pro Lys Ile Val Lys Trp Asp Arg Asp Met Gly
130                 135                 140

Gly Gly Gly Ser Gly Gly Gly Gly Ser Gly Gly Gly Gly Ser Gly Gly
145                 150                 155                 160

Gly Gly Ser Gly Ser His Ser Met Arg Tyr Phe Phe Thr Ser Val Ser
            165                 170                 175

Arg Pro Gly Arg Gly Glu Pro Arg Phe Ile Ala Val Gly Tyr Val Asp
            180                 185                 190

Asp Thr Gln Phe Val Arg Phe Asp Ser Asp Ala Ala Ser Gln Arg Met
        195                 200                 205

Glu Pro Arg Ala Pro Trp Ile Glu Gln Glu Gly Pro Glu Tyr Trp Asp
210                 215                 220

Gly Glu Thr Arg Lys Val Lys Ala His Ser Gln Thr His Arg Val Asp
225                 230                 235                 240

Leu Gly Thr Leu Arg Gly Xaa Tyr Asn Gln Ser Glu Ala Gly Ser His
                245                 250                 255

Thr Val Gln Arg Met Tyr Gly Cys Asp Val Gly Ser Asp Trp Arg Phe
            260                 265                 270

Leu Arg Gly Tyr His Gln Tyr Ala Tyr Asp Gly Lys Asp Tyr Ile Ala
        275                 280                 285

Leu Lys Glu Asp Leu Arg Ser Trp Thr Ala Ala Asp Met Ala Ala Gln
290                 295                 300

Thr Thr Lys His Lys Trp Glu Ala Ala His Val Ala Glu Gln Leu Arg
305                 310                 315                 320

Ala Tyr Leu Glu Gly Thr Cys Val Glu Trp Leu Arg Arg Tyr Leu Glu
                325                 330                 335

Asn Gly Lys Glu Thr Leu Gln Arg Thr Asp Ala Pro Lys Thr His Met
            340                 345                 350

Thr His His Ala Val Ser Asp His Glu Ala Thr Leu Arg Cys Trp Ala
        355                 360                 365

Leu Ser Phe Tyr Pro Ala Glu Ile Thr Leu Thr Trp Gln Arg Asp Gly
370                 375                 380
```

```
Glu Asp Gln Thr Gln Asp Thr Glu Leu Val Glu Thr Arg Pro Ala Gly
385                 390                 395                 400

Asp Gly Thr Phe Gln Lys Trp Ala Ala Val Val Pro Ser Gly Gln
            405                 410                 415

Glu Gln Arg Tyr Thr Cys His Val Gln His Glu Gly Leu Pro Lys Pro
            420                 425                 430

Leu Thr Leu Arg Trp Glu Pro Ser Ser Gln Pro Thr Ile Pro Ile Val
            435                 440                 445

Gly Ile Ile Ala Gly Leu Val Leu Phe Gly Ala Val Ile Thr Gly Ala
        450                 455                 460

Val Val Ala Ala Val Met Trp Arg Arg Lys Ser Ser Asp Arg Lys Gly
465                 470                 475                 480

Gly Ser Tyr Ser Gln Ala Ala Ser Ser Asp Ser Ala Gln Gly Ser Asp
            485                 490                 495

Val Ser Leu Thr Ala Cys Lys Val
            500

<210> SEQ ID NO 17
<211> LENGTH: 504
<212> TYPE: PRT
<213> ORGANISM: Artificial
<220> FEATURE:
<223> OTHER INFORMATION: Synthetic; sequence comprising antigen peptide
      sequence, beta2-microglobulin sequence and human MHC class I heavy
      chain sequence
<220> FEATURE:
<221> NAME/KEY: PEPTIDE
<222> LOCATION: (21)..(29)
<223> OTHER INFORMATION: Antigen peptide sequence
<220> FEATURE:
<221> NAME/KEY: MISC_FEATURE
<222> LOCATION: (247)..(247)
<223> OTHER INFORMATION: Tyr-247 substituted with alanine

<400> SEQUENCE: 17

Met Ala Arg Ser Val Thr Leu Val Phe Leu Val Leu Val Ser Leu Thr
1               5                   10                  15

Gly Leu Tyr Ala Xaa Xaa Xaa Xaa Xaa Xaa Xaa Xaa Xaa Gly Gly Gly
            20                  25                  30

Ala Ser Gly Gly Gly Gly Ser Gly Gly Gly Gly Ser Ile Gln Arg Thr
        35                  40                  45

Pro Lys Ile Gln Val Tyr Ser Arg His Pro Ala Glu Asn Gly Lys Ser
50                  55                  60

Asn Phe Leu Asn Cys Tyr Val Ser Gly Phe His Pro Ser Asp Ile Glu
65                  70                  75                  80

Val Asp Leu Leu Lys Asn Gly Glu Arg Ile Glu Lys Val Glu His Ser
                85                  90                  95

Asp Leu Ser Phe Ser Lys Asp Trp Ser Phe Tyr Leu Leu Tyr Tyr Thr
            100                 105                 110

Glu Phe Thr Pro Thr Glu Lys Asp Glu Tyr Ala Cys Arg Val Asn His
        115                 120                 125

Val Thr Leu Ser Gln Pro Lys Ile Val Lys Trp Asp Arg Asp Met Gly
130                 135                 140

Gly Gly Gly Ser Gly Gly Gly Gly Ser Gly Gly Gly Gly Ser Gly Gly
145                 150                 155                 160

Gly Gly Ser Gly Ser His Ser Met Arg Tyr Phe Phe Thr Ser Val Ser
            165                 170                 175

Arg Pro Gly Arg Gly Glu Pro Arg Phe Ile Ala Val Gly Tyr Val Asp
        180                 185                 190
```

```
Asp Thr Gln Phe Val Arg Phe Asp Ser Asp Ala Ala Ser Gln Arg Met
        195                 200                 205

Glu Pro Arg Ala Pro Trp Ile Glu Gln Glu Gly Pro Glu Tyr Trp Asp
    210                 215                 220

Gly Glu Thr Arg Lys Val Lys Ala His Ser Gln Thr His Arg Val Asp
225                 230                 235                 240

Leu Gly Thr Leu Arg Gly Ala Tyr Asn Gln Ser Glu Ala Gly Ser His
                245                 250                 255

Thr Val Gln Arg Met Tyr Gly Cys Asp Val Gly Ser Asp Trp Arg Phe
            260                 265                 270

Leu Arg Gly Tyr His Gln Tyr Ala Tyr Asp Gly Lys Asp Tyr Ile Ala
        275                 280                 285

Leu Lys Glu Asp Leu Arg Ser Trp Thr Ala Ala Asp Met Ala Ala Gln
    290                 295                 300

Thr Thr Lys His Lys Trp Glu Ala Ala His Val Ala Glu Gln Leu Arg
305                 310                 315                 320

Ala Tyr Leu Glu Gly Thr Cys Val Glu Trp Leu Arg Arg Tyr Leu Glu
                325                 330                 335

Asn Gly Lys Glu Thr Leu Gln Arg Thr Asp Ala Pro Lys Thr His Met
            340                 345                 350

Thr His His Ala Val Ser Asp His Glu Ala Thr Leu Arg Cys Trp Ala
        355                 360                 365

Leu Ser Phe Tyr Pro Ala Glu Ile Thr Leu Thr Trp Gln Arg Asp Gly
    370                 375                 380

Glu Asp Gln Thr Gln Asp Thr Glu Leu Val Glu Thr Arg Pro Ala Gly
385                 390                 395                 400

Asp Gly Thr Phe Gln Lys Trp Ala Ala Val Val Val Pro Ser Gly Gln
                405                 410                 415

Glu Gln Arg Tyr Thr Cys His Val Gln His Glu Gly Leu Pro Lys Pro
            420                 425                 430

Leu Thr Leu Arg Trp Glu Pro Ser Ser Gln Pro Thr Ile Pro Ile Val
        435                 440                 445

Gly Ile Ile Ala Gly Leu Val Leu Phe Gly Ala Val Ile Thr Gly Ala
    450                 455                 460

Val Val Ala Ala Val Met Trp Arg Arg Lys Ser Ser Asp Arg Lys Gly
465                 470                 475                 480

Gly Ser Tyr Ser Gln Ala Ala Ser Ser Asp Ser Ala Gln Gly Ser Asp
                485                 490                 495

Val Ser Leu Thr Ala Cys Lys Val
            500

<210> SEQ ID NO 18
<211> LENGTH: 8
<212> TYPE: PRT
<213> ORGANISM: Gallus gallus

<400> SEQUENCE: 18

Ser Ile Ile Asn Phe Glu Lys Leu
1               5

<210> SEQ ID NO 19
<211> LENGTH: 9
<212> TYPE: PRT
<213> ORGANISM: Mus musculus

<400> SEQUENCE: 19
```

```
Gln Leu Ser Pro Phe Asp Phe Asp Leu
1               5
```

```
<210> SEQ ID NO 20
<211> LENGTH: 8
<212> TYPE: PRT
<213> ORGANISM: Artificial
<220> FEATURE:
<223> OTHER INFORMATION: Synthetic

<400> SEQUENCE: 20

Ser Ile Tyr Arg Tyr Tyr Gly Leu
1               5
```

```
<210> SEQ ID NO 21
<211> LENGTH: 504
<212> TYPE: PRT
<213> ORGANISM: Artificial
<220> FEATURE:
<223> OTHER INFORMATION: Cytomegalovirus

<400> SEQUENCE: 21

Met Ala Arg Ser Val Thr Leu Val Phe Leu Val Leu Val Ser Leu Thr
1               5                   10                  15

Gly Leu Tyr Ala Asn Leu Val Pro Met Val Ala Thr Val Gly Gly Gly
                20                  25                  30

Ala Ser Gly Gly Gly Gly Ser Gly Gly Gly Gly Ser Ile Gln Arg Thr
            35                  40                  45

Pro Lys Ile Gln Val Tyr Ser Arg His Pro Ala Glu Asn Gly Lys Ser
    50                  55                  60

Asn Phe Leu Asn Cys Tyr Val Ser Gly Phe His Pro Ser Asp Ile Glu
65                  70                  75                  80

Val Asp Leu Leu Lys Asn Gly Glu Arg Ile Glu Lys Val Glu His Ser
                85                  90                  95

Asp Leu Ser Phe Ser Lys Asp Trp Ser Phe Tyr Leu Leu Tyr Tyr Thr
                100                 105                 110

Glu Phe Thr Pro Thr Glu Lys Asp Glu Tyr Ala Cys Arg Val Asn His
            115                 120                 125

Val Thr Leu Ser Gln Pro Lys Ile Val Lys Trp Asp Arg Asp Met Gly
    130                 135                 140

Gly Gly Gly Ser Gly Gly Gly Gly Ser Gly Gly Gly Gly Ser Gly Gly
145                 150                 155                 160

Gly Gly Ser Gly Ser His Ser Met Arg Tyr Phe Phe Thr Ser Val Ser
                165                 170                 175

Arg Pro Gly Arg Gly Glu Pro Arg Phe Ile Ala Val Gly Tyr Val Asp
                180                 185                 190

Asp Thr Gln Phe Val Arg Phe Asp Ser Asp Ala Ala Ser Gln Arg Met
            195                 200                 205

Glu Pro Arg Ala Pro Trp Ile Glu Gln Glu Gly Pro Glu Tyr Trp Asp
    210                 215                 220

Gly Glu Thr Arg Lys Val Lys Ala His Ser Gln Thr His Arg Val Asp
225                 230                 235                 240

Leu Gly Thr Leu Arg Gly Tyr Tyr Asn Gln Ser Glu Ala Gly Ser His
                245                 250                 255

Thr Val Gln Arg Met Tyr Gly Cys Asp Val Gly Ser Asp Trp Arg Phe
                260                 265                 270

Leu Arg Gly Tyr His Gln Tyr Ala Tyr Asp Gly Lys Asp Tyr Ile Ala
            275                 280                 285
```

```
Leu Lys Glu Asp Leu Arg Ser Trp Thr Ala Ala Asp Met Ala Ala Gln
        290                 295                 300

Thr Thr Lys His Lys Trp Glu Ala Ala His Val Ala Glu Gln Leu Arg
305                 310                 315                 320

Ala Tyr Leu Glu Gly Thr Cys Val Glu Trp Leu Arg Arg Tyr Leu Glu
                325                 330                 335

Asn Gly Lys Glu Thr Leu Gln Arg Thr Asp Ala Pro Lys Thr His Met
                340                 345                 350

Thr His His Ala Val Ser Asp His Glu Ala Thr Leu Arg Cys Trp Ala
            355                 360                 365

Leu Ser Phe Tyr Pro Ala Glu Ile Thr Leu Thr Trp Gln Arg Asp Gly
        370                 375                 380

Glu Asp Gln Thr Gln Asp Thr Glu Leu Val Glu Thr Arg Pro Ala Gly
385                 390                 395                 400

Asp Gly Thr Phe Gln Lys Trp Ala Ala Val Val Val Pro Ser Gly Gln
                405                 410                 415

Glu Gln Arg Tyr Thr Cys His Val Gln His Glu Gly Leu Pro Lys Pro
                420                 425                 430

Leu Thr Leu Arg Trp Glu Pro Ser Ser Gln Pro Thr Ile Pro Ile Val
            435                 440                 445

Gly Ile Ile Ala Gly Leu Val Leu Phe Gly Ala Val Ile Thr Gly Ala
450                 455                 460

Val Val Ala Ala Val Met Trp Arg Arg Lys Ser Ser Asp Arg Lys Gly
465                 470                 475                 480

Gly Ser Tyr Ser Gln Ala Ala Ser Ser Asp Ser Ala Gln Gly Ser Asp
                485                 490                 495

Val Ser Leu Thr Ala Cys Lys Val
            500

<210> SEQ ID NO 22
<211> LENGTH: 504
<212> TYPE: PRT
<213> ORGANISM: Artificial
<220> FEATURE:
<223> OTHER INFORMATION: Epstein-Barr virus

<400> SEQUENCE: 22

Met Ala Arg Ser Val Thr Leu Val Phe Leu Val Leu Val Ser Leu Thr
1               5                   10                  15

Gly Leu Tyr Ala Gly Leu Cys Thr Leu Val Ala Met Leu Gly Gly Gly
                20                  25                  30

Ala Ser Gly Gly Gly Gly Ser Gly Gly Gly Ser Ile Gln Arg Thr
            35                  40                  45

Pro Lys Ile Gln Val Tyr Ser Arg His Pro Ala Glu Asn Gly Lys Ser
        50                  55                  60

Asn Phe Leu Asn Cys Tyr Val Ser Gly Phe His Pro Ser Asp Ile Glu
65                  70                  75                  80

Val Asp Leu Leu Lys Asn Gly Glu Arg Ile Glu Lys Val Glu His Ser
                85                  90                  95

Asp Leu Ser Phe Ser Lys Asp Trp Ser Phe Tyr Leu Leu Tyr Tyr Thr
            100                 105                 110

Glu Phe Thr Pro Thr Glu Lys Asp Glu Tyr Ala Cys Arg Val Asn His
        115                 120                 125

Val Thr Leu Ser Gln Pro Lys Ile Val Lys Trp Asp Arg Asp Met Gly
    130                 135                 140

Gly Gly Gly Ser Gly Gly Gly Gly Ser Gly Gly Gly Gly Ser Gly Gly
```

```
            145                 150                 155                 160
Gly Gly Ser Gly Ser His Ser Met Arg Tyr Phe Phe Thr Ser Val Ser
                165                 170                 175
Arg Pro Gly Arg Gly Glu Pro Arg Phe Ile Ala Val Gly Tyr Val Asp
            180                 185                 190
Asp Thr Gln Phe Val Arg Phe Asp Ser Asp Ala Ala Ser Gln Arg Met
        195                 200                 205
Glu Pro Arg Ala Pro Trp Ile Glu Gln Glu Gly Pro Glu Tyr Trp Asp
    210                 215                 220
Gly Glu Thr Arg Lys Val Lys Ala His Ser Gln Thr His Arg Val Asp
225                 230                 235                 240
Leu Gly Thr Leu Arg Gly Tyr Tyr Asn Gln Ser Glu Ala Gly Ser His
                245                 250                 255
Thr Val Gln Arg Met Tyr Gly Cys Asp Val Gly Ser Asp Trp Arg Phe
            260                 265                 270
Leu Arg Gly Tyr His Gln Tyr Ala Tyr Asp Gly Lys Asp Tyr Ile Ala
        275                 280                 285
Leu Lys Glu Asp Leu Arg Ser Trp Thr Ala Ala Asp Met Ala Ala Gln
    290                 295                 300
Thr Thr Lys His Lys Trp Glu Ala Ala His Val Ala Glu Gln Leu Arg
305                 310                 315                 320
Ala Tyr Leu Glu Gly Thr Cys Val Glu Trp Leu Arg Arg Tyr Leu Glu
                325                 330                 335
Asn Gly Lys Glu Thr Leu Gln Arg Thr Asp Ala Pro Lys Thr His Met
            340                 345                 350
Thr His His Ala Val Ser Asp His Glu Ala Thr Leu Arg Cys Trp Ala
        355                 360                 365
Leu Ser Phe Tyr Pro Ala Glu Ile Thr Leu Thr Trp Gln Arg Asp Gly
    370                 375                 380
Glu Asp Gln Thr Gln Asp Thr Glu Leu Val Glu Thr Arg Pro Ala Gly
385                 390                 395                 400
Asp Gly Thr Phe Gln Lys Trp Ala Ala Val Val Val Pro Ser Gly Gln
                405                 410                 415
Glu Gln Arg Tyr Thr Cys His Val Gln His Glu Gly Leu Pro Lys Pro
            420                 425                 430
Leu Thr Leu Arg Trp Glu Pro Ser Ser Gln Pro Thr Ile Pro Ile Val
        435                 440                 445
Gly Ile Ile Ala Gly Leu Val Leu Phe Gly Ala Val Ile Thr Gly Ala
    450                 455                 460
Val Val Ala Ala Val Met Trp Arg Arg Lys Ser Ser Asp Arg Lys Gly
465                 470                 475                 480
Gly Ser Tyr Ser Gln Ala Ala Ser Ser Asp Ser Ala Gln Gly Ser Asp
                485                 490                 495
Val Ser Leu Thr Ala Cys Lys Val
            500

<210> SEQ ID NO 23
<211> LENGTH: 504
<212> TYPE: PRT
<213> ORGANISM: Artificial
<220> FEATURE:
<223> OTHER INFORMATION: Synthetic

<400> SEQUENCE: 23

Met Ala Arg Ser Val Thr Leu Val Phe Leu Val Leu Val Ser Leu Thr
1               5                   10                  15
```

Gly Leu Tyr Ala Gly Ile Leu Gly Phe Val Phe Thr Leu Gly Gly
            20                  25                  30

Ala Ser Gly Gly Gly Ser Gly Gly Gly Ser Ile Gln Arg Thr
        35                  40                  45

Pro Lys Ile Gln Val Tyr Ser Arg His Pro Ala Glu Asn Gly Lys Ser
50                  55                  60

Asn Phe Leu Asn Cys Tyr Val Ser Gly Phe His Pro Ser Asp Ile Glu
65                  70                  75                  80

Val Asp Leu Leu Lys Asn Gly Glu Arg Ile Glu Lys Val Glu His Ser
                85                  90                  95

Asp Leu Ser Phe Ser Lys Asp Trp Ser Phe Tyr Leu Leu Tyr Tyr Thr
                100                 105                 110

Glu Phe Thr Pro Thr Glu Lys Asp Glu Tyr Ala Cys Arg Val Asn His
            115                 120                 125

Val Thr Leu Ser Gln Pro Lys Ile Val Lys Trp Asp Arg Asp Met Gly
    130                 135                 140

Gly Gly Gly Ser Gly Gly Gly Ser Gly Gly Gly Ser Gly Gly
145                 150                 155                 160

Gly Gly Ser Gly Ser His Ser Met Arg Tyr Phe Phe Thr Ser Val Ser
                165                 170                 175

Arg Pro Gly Arg Gly Glu Pro Arg Phe Ile Ala Val Gly Tyr Val Asp
            180                 185                 190

Asp Thr Gln Phe Val Arg Phe Asp Ser Asp Ala Ala Ser Gln Arg Met
        195                 200                 205

Glu Pro Arg Ala Pro Trp Ile Glu Gln Glu Gly Pro Glu Tyr Trp Asp
210                 215                 220

Gly Glu Thr Arg Lys Val Lys Ala His Ser Gln Thr His Arg Val Asp
225                 230                 235                 240

Leu Gly Thr Leu Arg Gly Tyr Tyr Asn Gln Ser Glu Ala Gly Ser His
                245                 250                 255

Thr Val Gln Arg Met Tyr Gly Cys Asp Val Gly Ser Asp Trp Arg Phe
            260                 265                 270

Leu Arg Gly Tyr His Gln Tyr Ala Tyr Asp Gly Lys Asp Tyr Ile Ala
        275                 280                 285

Leu Lys Glu Asp Leu Arg Ser Trp Thr Ala Ala Asp Met Ala Ala Gln
290                 295                 300

Thr Thr Lys His Lys Trp Glu Ala Ala His Val Ala Glu Gln Leu Arg
305                 310                 315                 320

Ala Tyr Leu Glu Gly Thr Cys Val Glu Trp Leu Arg Arg Tyr Leu Glu
                325                 330                 335

Asn Gly Lys Glu Thr Leu Gln Arg Thr Asp Ala Pro Lys Thr His Met
            340                 345                 350

Thr His His Ala Val Ser Asp His Glu Ala Thr Leu Arg Cys Trp Ala
        355                 360                 365

Leu Ser Phe Tyr Pro Ala Glu Ile Thr Leu Thr Trp Gln Arg Asp Gly
370                 375                 380

Glu Asp Gln Thr Gln Asp Thr Glu Leu Val Glu Thr Arg Pro Ala Gly
385                 390                 395                 400

Asp Gly Thr Phe Gln Lys Trp Ala Ala Val Val Val Pro Ser Gly Gln
                405                 410                 415

Glu Gln Arg Tyr Thr Cys His Val Gln His Glu Gly Leu Pro Lys Pro
            420                 425                 430

Leu Thr Leu Arg Trp Glu Pro Ser Ser Gln Pro Thr Ile Pro Ile Val

```
                    435                 440                 445
Gly Ile Ile Ala Gly Leu Val Leu Phe Gly Ala Val Ile Thr Gly Ala
        450                 455                 460
Val Val Ala Ala Val Met Trp Arg Arg Lys Ser Ser Asp Arg Lys Gly
465                 470                 475                 480
Gly Ser Tyr Ser Gln Ala Ala Ser Ser Asp Ser Ala Gln Gly Ser Asp
                485                 490                 495
Val Ser Leu Thr Ala Cys Lys Val
            500

<210> SEQ ID NO 24
<211> LENGTH: 504
<212> TYPE: PRT
<213> ORGANISM: Artificial
<220> FEATURE:
<223> OTHER INFORMATION: Synthetic

<400> SEQUENCE: 24

Met Ala Arg Ser Val Thr Leu Val Phe Leu Val Leu Val Ser Leu Thr
1               5                   10                  15
Gly Leu Tyr Ala Ile Met Asp Gln Val Pro Phe Ser Val Gly Gly Gly
            20                  25                  30
Ala Ser Gly Gly Gly Gly Ser Gly Gly Gly Gly Ser Ile Gln Arg Thr
        35                  40                  45
Pro Lys Ile Gln Val Tyr Ser Arg His Pro Ala Glu Asn Gly Lys Ser
    50                  55                  60
Asn Phe Leu Asn Cys Tyr Val Ser Gly Phe His Pro Ser Asp Ile Glu
65                  70                  75                  80
Val Asp Leu Leu Lys Asn Gly Glu Arg Ile Glu Lys Val Glu His Ser
                85                  90                  95
Asp Leu Ser Phe Ser Lys Asp Trp Ser Phe Tyr Leu Leu Tyr Tyr Thr
            100                 105                 110
Glu Phe Thr Pro Thr Glu Lys Asp Glu Tyr Ala Cys Arg Val Asn His
        115                 120                 125
Val Thr Leu Ser Gln Pro Lys Ile Val Lys Trp Asp Arg Asp Met Gly
    130                 135                 140
Gly Gly Gly Ser Gly Gly Gly Gly Ser Gly Gly Gly Gly Ser Gly Gly
145                 150                 155                 160
Gly Gly Ser Gly Ser His Ser Met Arg Tyr Phe Phe Thr Ser Val Ser
                165                 170                 175
Arg Pro Gly Arg Gly Glu Pro Arg Phe Ile Ala Val Gly Tyr Val Asp
            180                 185                 190
Asp Thr Gln Phe Val Arg Phe Asp Ser Asp Ala Ala Ser Gln Arg Met
        195                 200                 205
Glu Pro Arg Ala Pro Trp Ile Glu Gln Glu Gly Pro Glu Tyr Trp Asp
    210                 215                 220
Gly Glu Thr Arg Lys Val Lys Ala His Ser Gln Thr His Arg Val Asp
225                 230                 235                 240
Leu Gly Thr Leu Arg Gly Tyr Tyr Asn Gln Ser Glu Ala Gly Ser His
                245                 250                 255
Thr Val Gln Arg Met Tyr Gly Cys Asp Val Gly Ser Asp Trp Arg Phe
            260                 265                 270
Leu Arg Gly Tyr His Gln Tyr Ala Tyr Asp Gly Lys Asp Tyr Ile Ala
        275                 280                 285
Leu Lys Glu Asp Leu Arg Ser Trp Thr Ala Ala Asp Met Ala Ala Gln
    290                 295                 300
```

-continued

```
Thr Thr Lys His Lys Trp Glu Ala Ala His Val Ala Glu Gln Leu Arg
305                 310                 315                 320

Ala Tyr Leu Glu Gly Thr Cys Val Glu Trp Leu Arg Arg Tyr Leu Glu
                325                 330                 335

Asn Gly Lys Glu Thr Leu Gln Arg Thr Asp Ala Pro Lys Thr His Met
            340                 345                 350

Thr His His Ala Val Ser Asp His Glu Ala Thr Leu Arg Cys Trp Ala
        355                 360                 365

Leu Ser Phe Tyr Pro Ala Glu Ile Thr Leu Thr Trp Gln Arg Asp Gly
    370                 375                 380

Glu Asp Gln Thr Gln Asp Thr Glu Leu Val Glu Thr Arg Pro Ala Gly
385                 390                 395                 400

Asp Gly Thr Phe Gln Lys Trp Ala Ala Val Val Val Pro Ser Gly Gln
                405                 410                 415

Glu Gln Arg Tyr Thr Cys His Val Gln His Glu Gly Leu Pro Lys Pro
            420                 425                 430

Leu Thr Leu Arg Trp Glu Pro Ser Ser Gln Pro Thr Ile Pro Ile Val
        435                 440                 445

Gly Ile Ile Ala Gly Leu Val Leu Phe Gly Ala Val Ile Thr Gly Ala
    450                 455                 460

Val Val Ala Ala Val Met Trp Arg Arg Lys Ser Ser Asp Arg Lys Gly
465                 470                 475                 480

Gly Ser Tyr Ser Gln Ala Ala Ser Ser Asp Ser Ala Gln Gly Ser Asp
                485                 490                 495

Val Ser Leu Thr Ala Cys Lys Val
            500

<210> SEQ ID NO 25
<211> LENGTH: 504
<212> TYPE: PRT
<213> ORGANISM: Artificial
<220> FEATURE:
<223> OTHER INFORMATION: Synthetic

<400> SEQUENCE: 25

Met Ala Arg Ser Val Thr Leu Val Phe Leu Val Leu Val Ser Leu Thr
1               5                   10                  15

Gly Leu Tyr Ala Tyr Leu Glu Pro Gly Pro Val Thr Val Gly Gly Gly
            20                  25                  30

Ala Ser Gly Gly Gly Gly Ser Gly Gly Gly Gly Ser Ile Gln Arg Thr
        35                  40                  45

Pro Lys Ile Gln Val Tyr Ser Arg His Pro Ala Glu Asn Gly Lys Ser
    50                  55                  60

Asn Phe Leu Asn Cys Tyr Val Ser Gly Phe His Pro Ser Asp Ile Glu
65                  70                  75                  80

Val Asp Leu Leu Lys Asn Gly Glu Arg Ile Glu Lys Val Glu His Ser
                85                  90                  95

Asp Leu Ser Phe Ser Lys Asp Trp Ser Phe Tyr Leu Leu Tyr Tyr Thr
            100                 105                 110

Glu Phe Thr Pro Thr Glu Lys Asp Glu Tyr Ala Cys Arg Val Asn His
        115                 120                 125

Val Thr Leu Ser Gln Pro Lys Ile Val Lys Trp Asp Arg Asp Met Gly
    130                 135                 140

Gly Gly Gly Ser Gly Gly Gly Gly Ser Gly Gly Gly Gly Ser Gly Gly
145                 150                 155                 160
```

Gly Gly Ser Gly Ser His Ser Met Arg Tyr Phe Phe Thr Ser Val Ser
            165                 170                 175

Arg Pro Gly Arg Gly Glu Pro Arg Phe Ile Ala Val Gly Tyr Val Asp
        180                 185                 190

Asp Thr Gln Phe Val Arg Phe Asp Ser Asp Ala Ala Ser Gln Arg Met
    195                 200                 205

Glu Pro Arg Ala Pro Trp Ile Glu Gln Glu Gly Pro Glu Tyr Trp Asp
210                 215                 220

Gly Glu Thr Arg Lys Val Lys Ala His Ser Gln Thr His Arg Val Asp
225                 230                 235                 240

Leu Gly Thr Leu Arg Gly Tyr Tyr Asn Gln Ser Glu Ala Gly Ser His
            245                 250                 255

Thr Val Gln Arg Met Tyr Gly Cys Asp Val Gly Ser Asp Trp Arg Phe
        260                 265                 270

Leu Arg Gly Tyr His Gln Tyr Ala Tyr Asp Gly Lys Asp Tyr Ile Ala
    275                 280                 285

Leu Lys Glu Asp Leu Arg Ser Trp Thr Ala Ala Asp Met Ala Ala Gln
290                 295                 300

Thr Thr Lys His Lys Trp Glu Ala Ala His Val Ala Glu Gln Leu Arg
305                 310                 315                 320

Ala Tyr Leu Glu Gly Thr Cys Val Glu Trp Leu Arg Arg Tyr Leu Glu
            325                 330                 335

Asn Gly Lys Glu Thr Leu Gln Arg Thr Asp Ala Pro Lys Thr His Met
        340                 345                 350

Thr His His Ala Val Ser Asp His Glu Ala Thr Leu Arg Cys Trp Ala
    355                 360                 365

Leu Ser Phe Tyr Pro Ala Glu Ile Thr Leu Thr Trp Gln Arg Asp Gly
370                 375                 380

Glu Asp Gln Thr Gln Asp Thr Glu Leu Val Glu Thr Arg Pro Ala Gly
385                 390                 395                 400

Asp Gly Thr Phe Gln Lys Trp Ala Ala Val Val Val Pro Ser Gly Gln
            405                 410                 415

Glu Gln Arg Tyr Thr Cys His Val Gln His Glu Gly Leu Pro Lys Pro
        420                 425                 430

Leu Thr Leu Arg Trp Glu Pro Ser Ser Gln Pro Thr Ile Pro Ile Val
    435                 440                 445

Gly Ile Ile Ala Gly Leu Val Leu Phe Gly Ala Val Ile Thr Gly Ala
450                 455                 460

Val Val Ala Ala Val Met Trp Arg Arg Lys Ser Ser Asp Arg Lys Gly
465                 470                 475                 480

Gly Ser Tyr Ser Gln Ala Ala Ser Ser Asp Ser Ala Gln Gly Ser Asp
            485                 490                 495

Val Ser Leu Thr Ala Cys Lys Val
        500

<210> SEQ ID NO 26
<211> LENGTH: 504
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(24)

<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 26

```
Met Ala Arg Ser Val Thr Leu Val Phe Leu Val Leu Val Ser Leu Thr
 1               5                  10                  15

Gly Leu Tyr Ala Xaa Leu Xaa Xaa Leu Val Xaa Thr Val Gly Gly Gly
             20                  25                  30

Ala Ser Gly Gly Gly Ser Gly Gly Gly Ser Ile Gln Arg Thr
         35                  40                  45

Pro Lys Ile Gln Val Tyr Ser Arg His Pro Ala Glu Asn Gly Lys Ser
 50                  55                  60

Asn Phe Leu Asn Cys Tyr Val Ser Gly Phe His Pro Ser Asp Ile Glu
 65                  70                  75                  80

Val Asp Leu Leu Lys Asn Gly Glu Arg Ile Glu Lys Val Glu His Ser
                 85                  90                  95

Asp Leu Ser Phe Ser Lys Asp Trp Ser Phe Tyr Leu Leu Tyr Tyr Thr
            100                 105                 110

Glu Phe Thr Pro Thr Glu Lys Asp Glu Tyr Ala Cys Arg Val Asn His
        115                 120                 125

Val Thr Leu Ser Gln Pro Lys Ile Val Lys Trp Asp Arg Asp Met Gly
130                 135                 140

Gly Gly Ser Gly Gly Gly Gly Ser Gly Gly Gly Gly Ser Gly Gly Gly
145                 150                 155                 160

Gly Gly Ser Gly Ser His Ser Met Arg Tyr Phe Phe Thr Ser Val Ser
                165                 170                 175

Arg Pro Gly Arg Gly Glu Pro Arg Phe Ile Ala Val Gly Tyr Val Asp
            180                 185                 190

Asp Thr Gln Phe Val Arg Phe Asp Ser Asp Ala Ala Ser Gln Arg Met
        195                 200                 205

Glu Pro Arg Ala Pro Trp Ile Glu Gln Glu Gly Pro Glu Tyr Trp Asp
210                 215                 220

Gly Glu Thr Arg Lys Val Lys Ala His Ser Gln Thr His Arg Val Asp
225                 230                 235                 240

Leu Gly Thr Leu Arg Gly Tyr Tyr Asn Gln Ser Glu Ala Gly Ser His
                245                 250                 255

Thr Val Gln Arg Met Tyr Gly Cys Asp Val Gly Ser Asp Trp Arg Phe
            260                 265                 270

Leu Arg Gly Tyr His Gln Tyr Ala Tyr Asp Gly Lys Asp Tyr Ile Ala
        275                 280                 285

Leu Lys Glu Asp Leu Arg Ser Trp Thr Ala Ala Asp Met Ala Ala Gln
290                 295                 300

Thr Thr Lys His Lys Trp Glu Ala Ala His Val Ala Glu Gln Leu Arg
305                 310                 315                 320

Ala Tyr Leu Glu Gly Thr Cys Val Glu Trp Leu Arg Arg Tyr Leu Glu
                325                 330                 335

Asn Gly Lys Glu Thr Leu Gln Arg Thr Asp Ala Pro Lys Thr His Met
            340                 345                 350

Thr His His Ala Val Ser Asp His Glu Ala Thr Leu Arg Cys Trp Ala
        355                 360                 365

Leu Ser Phe Tyr Pro Ala Glu Ile Thr Leu Thr Trp Gln Arg Asp Gly
370                 375                 380
```

```
Glu Asp Gln Thr Gln Asp Thr Glu Leu Val Glu Thr Arg Pro Ala Gly
385                 390                 395                 400

Asp Gly Thr Phe Gln Lys Trp Ala Ala Val Val Pro Ser Gly Gln
            405                 410                 415

Glu Gln Arg Tyr Thr Cys His Val Gln His Glu Gly Leu Pro Lys Pro
            420                 425                 430

Leu Thr Leu Arg Trp Glu Pro Ser Ser Gln Pro Thr Ile Pro Ile Val
        435                 440                 445

Gly Ile Ile Ala Gly Leu Val Leu Phe Gly Ala Val Ile Thr Gly Ala
        450                 455                 460

Val Val Ala Ala Val Met Trp Arg Arg Lys Ser Ser Asp Arg Lys Gly
465                 470                 475                 480

Gly Ser Tyr Ser Gln Ala Ala Ser Ser Asp Ser Ala Gln Gly Ser Asp
            485                 490                 495

Val Ser Leu Thr Ala Cys Lys Val
            500

<210> SEQ ID NO 27
<211> LENGTH: 10
<212> TYPE: PRT
<213> ORGANISM: Artificial
<220> FEATURE:
<223> OTHER INFORMATION: Synthetic

<400> SEQUENCE: 27

Gly Gly Gly Ala Ser Gly Gly Gly Gly Ser
1               5                   10

<210> SEQ ID NO 28
<211> LENGTH: 6960
<212> TYPE: DNA
<213> ORGANISM: Artificial
<220> FEATURE:
<223> OTHER INFORMATION: Synthetic; plasmid
<220> FEATURE:
<221> NAME/KEY: misc_feature
<222> LOCATION: (2170)..(2196)
<223> OTHER INFORMATION: Sequence encoding antigen peptide
<220> FEATURE:
<221> NAME/KEY: misc_feature
<222> LOCATION: (2242)..(2538)
<223> OTHER INFORMATION: Sequence encoding beta2-microglobulin
<220> FEATURE:
<221> NAME/KEY: misc_feature
<222> LOCATION: (2599)..(3621)
<223> OTHER INFORMATION: Sequence encoding A2 MHC heavy chain

<400> SEQUENCE: 28
aagcttccca ttgcatacgt tgtatccata tcataatatg tacatttata ttggctcatg    60
tccaacatta ccgccatgtt gacattgatt attgactagt tattaatagt aatcaattac   120
ggggtcatta gttcatagcc catattggag ttccgcgtta cataacttac ggtaaatggc   180
ccgcctggct gaccgcccaa cgacccccgc ccttgacgt caataatgac gtatgttccc    240
atagtaacgc caatagggac tttccattga cgtcaatggg tggagtattt acggtaaact   300
gcccacttgg cagtacatca agtgtatcat atgccaagta cgccccctat tgacgtcaat   360
gacggtaaat ggcccgcctg gcattatgcc cagtacatga ccttatggga ctttcctact   420
tggcagtaca tctacgtatt agtcatcgct attaccatgg tgatgcggtt gtggcagtac   480
atcaatgggc gtggatagcg gtttgactca cggggatttc caagtctcca ccccattgac   540
gtcaatggga gtttgttttg gcaccaaaat caacgggact ttccaaaatg tcgtaacaac   600
tccgccccat tgacgcaaat gggcggtagg cgtgtacggt gggaggtcta taagcaga    660
```

-continued

```
gctcgtttag tgaaccggcg ccagtcctcc gattgactga gtcgcccggg tacccgtgta    720
tccaataaac cctcttgcag ttgcatccga cttgtggtct cgctgttcct tgggagggtc    780
tcctctgagt gattgactac ccgtcagcgg gggtctttca tttgggggct cgtccgggat    840
cgggagaccc ctgcccaggg accaccgacc caccaccggg aggtaagctg ccagcaact     900 tatctgtgtc tgtccgattg tctagtgtct atgactgatt ttatgcgcct cgtcggtac     960 tagttagcta actagctctg tatctggcgg acccgtggtg gaactgacga gttcggaaca    1020
cccggccgca accctgggag acgtcccagg gacttcgggg gccgttttg tggcccgacc     1080 tgagtcctaa aatcccgatc gtttaggact cttttggtgca ccccccttag aggagggata   1140
tgtggttctg gtaggagacg agaacctaaa acagttcccg cctccgtctg aattttgct     1200 ttcggtttgg gaccgaagcc gcgccgcgcg tcttgtctgc tgcagcatcg ttctgtgttg    1260
tctctgtctg actgtgtttc tgtatttgtc tgaaaatatg ggcccgggct agactgttac    1320
cactccctta agtttgacct taggtcactg gaaagatgtc gagcggatcg ctcacaacca    1380
gtcggtagat gtcaagaaga gacgttgggt taccttctgc tctgcagaat ggccaacctt    1440
taacgtcgga tggccgcgag acggcacctt taaccgagac ctcatcaccc aggttaagat    1500
caaggtcttt tcacctggcc cgcatggaca cccagaccag gtggggtaca tcgtgacctg    1560
ggaagccttg gcttttgacc ccctcccctg ggtcaagccc tttgtacacc ctaagcctcc    1620
gcctcctctt cctccatccg ccccgtctct ccccccttgaa cctcctcgtt cgaccccgcc   1680
tcgatcctcc ctttatccag ccctcactcc ttctctaggc gcccccatat ggccatatga    1740
gatcttatat ggggcacccc cgcccccttgt aaacttccct gaccctgaca tgacaagagt   1800
tactaacagc ccctctctcc aagctcactt acaggctctc tacttagtcc agcacgaagt    1860
ctggagacct ctggcggcag cctaccaaga acaactggac cgaccggtgg tacctcaccc    1920
ttaccgagtc ggcgacacag tgtgggtccg ccgacaccag actaagaacc tagaacctcg    1980
ctggaaagga ccttacacag tcctgctgac cacccccacc gccctcaaag tagacggcat    2040
cgcagcttgg atacacgccg cccacgtgaa ggctgccgac cccggggtgtg gaccatcctc   2100 tagactgcca tggctcgctc ggtgaccctg gtctttctgg tgcttgtctc actgaccggt    2160
ttgtatgcta acctggtgcc aatggtggct accgtgggag gaggtgctag cggtggtgga    2220
ggtagcggag gtggaggaag catccagcgt actccaaaga ttcaggttta ctcacgtcat    2280
ccagcagaga atggaaagtc aaatttcctg aattgctatg tgtctgggtt tcatccatcc    2340
gacattgaag ttgacttact gaagaatgga gagagaattg aaaaagtgga gcattcagac    2400
ttgtctttca gcaaggactg gtctttctat ctcttgtact acactgaatt caccccccact   2460 gaaaaagatg agtatgcctg ccgtgtgaac catgtgactt tgtcacagcc caagatagtt    2520
aagtgggatc gagacatggg cggtggtggt tccggtggag gcggttccgg aggtggtgga    2580
tccggtggtg gaggtagtgg ctctcactcc atgaggtatt tcttcacatc cgtgtcccgg    2640 cccgccgcg gggagccccg cttcatcgca gtgggctacg tggacgacac gcagttcgtg    2700
cggttcgaca gcgacgccgc gagccagagg atggagccgc gggcgccgtg gatagagcag    2760
gagggtccgg agtattggga cggggagaca cggaaagtga aggcccactc acagactcac    2820
cgagtggacc tggggacccct gcgcggctac tacaaccaga cgcaggccgg ttctcacacc    2880
gtccagagga tgtatggctg cgacgtgggg tcggactggc gcttcctccg cgggtaccac    2940
cagtacgcct acgacggcaa ggattacatc gccctgaaag aggacctgcg ctcttggacc    3000
gcggcggaca tggcagctca gaccaccaag cacaagtggg aggcggccca tgtggcggag    3060
```

```
cagttgagag cctacctgga gggcacgtgc gtggagtggc tccgcagata cctggagaac  3120
gggaaggaga cgctgcagcg cacggacgcc cccaaaacgc atatgactca ccacgctgtc  3180
tctgaccatg aagccaccct gaggtgctgg gccctgagct tctaccctgc ggagatcaca  3240
ctgacctggc agcgggatgg ggaggaccag acccaggaca cggagctcgt ggagaccagg  3300
cctgcagggg atggaacctt ccagaagtgg gcggctgtgg tggtgccttc tggacaggag  3360
cagagataca cctgccatgt gcagcatgag ggtttgccca gcccctcac cctgagatgg  3420 gagccgtctt cccagcccac catccccatc gtgggcatca ttgctggcct ggttctcttt  3480
ggagctgtga tcactggagc tgtggtcgct gctgtgatgt ggaggaggaa gagctcagat  3540
agaaaaggag ggagctactc tcaggctgca agcagtgaca gtgcccaggg ctctgatgtg  3600
tctctcacag cttgtaaagt gtgagcggcc gctggattag tccaatttgt taaagacagg  3660
atatcagtgg tccaggctct agttttgact caacaatatc accagctgaa gcctatagag  3720
tacgagccat agataaaata aaagatttta tttagtctcc agaaaaggg gggaatgaaa  3780 gacccccacct gtaggtttgg caagctagct taagtaacgc cattttgcaa ggcatggaaa  3840
aatacataac tgagaataga gaagttcaga tcaaggtcag gaacagatgg aacagctgaa  3900
tatgggccaa acaggatatc tgtggtaagc agttcctgcc ccggctcagg gccaagaaca  3960 gatgaacag ctgaatatgg gccaaacagg atatctgtgg taagcagttc ctgcccggc  4020 tcagggccaa gaacagatgg tccccagatg cggtccagcc ctcagcagtt tctagagaac  4080
catcagatgt ttccagggtg ccccaaggac ctgaaatgac cctgtgcctt atttgaacta  4140
accaatcagt tcgcttctcg cttctgttcg cgcgcttctg ctccccgagc tcaataaaag  4200
agcccacaac ccctcactcg gggcgccagt cctccgattg actgagtcgc ccgggtaccc  4260
gtgtatccaa taaaccctct tgcagttgca tccgacttgt ggtctcgctg ttccttggga  4320
gggtctcctc tgagtgattg actacccgtc agcggggtc tttcacacat gcagcatgta  4380
tcaaaattaa tttggtttt tttcttaagt atttacatta aatggccata gtgggtaccg  4440
agctcgaatt ccgtaatcat ggtcatagct gtttcctgtg tgaaattgtt atccgctcac  4500
aattccacac aacatacgag ccggaagcat aaagtgtaaa gcctggggtg cctaatgagt  4560
gagctaactc acattaattg cgttgcgctc actgcccgct ttccagtcgg gaaacctgtc  4620
gtgccagctg cattaatgaa tcggccaacg cgcggggaga ggcggtttgc gtattgggcg  4680
ctcttccgct tcctcgctca ctgactcgct gcgctcggtc gttcggctgc ggcgagcggt  4740
atcagctcac tcaaaggcgg taatacggtt atccacagaa tcagggata cgcaggaaa  4800 gaacatgtga gcaaaaggcc agcaaaaggc caggaaccgt aaaaaggccg cgttgctggc  4860
gtttttccat aggctccgcc cccctgacga gcatcacaaa aatcgacgct caagtcagag  4920
gtggcgaaac ccgacaggac tataaagata ccaggcgttt ccccctggaa gctccctcgt  4980
gcgctctcct gttccgaccc tgccgcttac cggatacctg tccgcctttc tcccttcggg  5040
aagcgtggcg ctttctcaat gctcacgctg taggtatctc agttcggtgt aggtcgttcg  5100
ctccaagctg ggctgtgtgc acgaaccccc cgttcagccc gaccgctgcg ccttatccgg  5160
taactatcgt cttgagtcca acccggtaag acacgactta tcgccactgg cagcagccac  5220
tggtaacagg attagcagag cgaggtatgt aggcggtgct acagagttct tgaagtggtg  5280
gcctaactac ggctacacta aggacagt atttggtatc tgcgctctgc tgaagccagt  5340
taccttcgga aaaagagttg gtagctcttg atccggcaaa caaaccaccg ctggtagcgg  5400 tggtttttt gtttgcaagc agcagattac gcgcagaaaa aaaggatctc aagaagatcc  5460
```

```
tttgatcttt tctacggggt ctgacgctca gtggaacgaa aactcacgtt aagggatttt    5520
ggtcatgaga ttatcaaaaa ggatcttcac ctagatcctt ttaaattaaa aatgaagttt    5580
taaatcaatc taaagtatat atgagtaaac ttggtctgac agttaccaat gcttaatcag    5640
tgaggcacct atctcagcga tctgtctatt tcgttcatcc atagttgcct gactccccgt    5700
cgtgtagata actacgatac gggagggctt accatctggc cccagtgctg caatgatacc    5760
gcgagaccca cgctcaccgg ctccagattt atcagcaata accagccagc cggaagggc    5820 cgagcgcaga agtggtcctg caactttatc cgcctccatc cagtctatta attgttgccg    5880
ggaagctaga gtaagtagtt cgccagttaa tagtttgcgc aacgttgttg ccattgctac    5940
aggcatcgtg gtgtcacgct cgtcgtttgg tatggcttca ttcagctccg gttcccaacg    6000
atcaaggcga gttacatgat cccccatgtt gtgcaaaaaa gcggttagct ccttcggtcc    6060
tccgatcgtt gtcagaagta agttggccgc agtgttatca ctcatggtta tggcagcact    6120
gcataattct cttactgtca tgccatccgt aagatgcttt tctgtgactg gtgagtactc    6180
aaccaagtca ttctgagaat agtgtatgcg gcgaccgagt tgctcttgcc cggcgtcaat    6240
acgggataat accgcgccac atagcagaac tttaaaagtg ctcatcattg gaaaacgttc    6300
ttcggggcga aaactctcaa ggatcttacc gctgttgaga tccagttcga tgtaacccac    6360
tcgtgcaccc aactgatctt cagcatcttt tactttcacc agcgtttctg ggtgagcaaa    6420
aacaggaagg caaaatgccg caaaaaggg aataagggcg acacggaaat gttgaatact    6480
catactcttc cttttcaat attattgaag catttatcag ggttattgtc tcatgagcgg    6540
atacatattt gaatgtattt agaaaaataa acaaataggg gttccgcgca catttccccg    6600
aaaagtgcca cctgacgtct aagaaaccat tattatcatg acattaacct ataaaaatag    6660
gcgtatcacg aggccctttc gtctcgcgcg tttcggtgat gacggtgaaa acctctgaca    6720
catgcagctc ccggagacgg tcacagcttg tctgtaagcg gatgccggga gcagacaagc    6780
ccgtcagggc gcgtcagcgg gtgttggcgg gtgtcggggc tggcttaact atgcggcatc    6840
agagcagatt gtactgagag tgcaccatat gcggtgtgaa ataccgcaca gatgcgtaag    6900
gagaaaatac cgcatcaggc gccattcgcc attcaggctg cgcaactgtt gggaagggcg    6960
```

<210> SEQ ID NO 29
<211> LENGTH: 7080
<212> TYPE: DNA
<213> ORGANISM: Artificial
<220> FEATURE:
<223> OTHER INFORMATION: Synthetic; plasmid
<220> FEATURE:
<221> NAME/KEY: misc_feature
<222> LOCATION: (2170)..(2196)
<223> OTHER INFORMATION: Sequence encoding antigen peptide
<220> FEATURE:
<221> NAME/KEY: misc_feature
<222> LOCATION: (2242)..(2538)
<223> OTHER INFORMATION: Sequence encoding beta2-microglobulin
<220> FEATURE:
<221> NAME/KEY: misc_feature
<222> LOCATION: (2599)..(3621)
<223> OTHER INFORMATION: Sequence encoding A2 MHC heavy chain

<400> SEQUENCE: 29

```
aagcttccca ttgcatacgt tgtatccata tcataatatg tacatttata ttggctcatg      60
tccaacatta ccgccatgtt gacattgatt attgactagt tattaatagt aatcaattac     120
ggggtcatta gttcatagcc catattggag ttccgcgtta cataacttac ggtaaatggc     180
ccgcctggct gaccgcccaa cgacccccgc ccttgacgt caataatgac gtatgttccc     240
```

| | |
|---|---|
| atagtaacgc caatagggac tttccattga cgtcaatggg tggagtattt acggtaaact | 300 |
| gcccacttgg cagtacatca agtgtatcat atgccaagta cgcccectat tgacgtcaat | 360 |
| gacggtaaat ggcccgcctg gcattatgcc cagtacatga ccttatggga ctttcctact | 420 |
| tggcagtaca tctacgtatt agtcatcgct attaccatgg tgatgcggtt gtggcagtac | 480 |
| atcaatgggc gtggatagcg gtttgactca cggggatttc caagtctcca ccccattgac | 540 |
| gtcaatggga gtttgttttg gcaccaaaat caacgggact ttccaaaatg tcgtaacaac | 600 |
| tccgccccat tgacgcaaat gggcggtagg cgtgtacggt gggaggtcta tataagcaga | 660 |
| gctcgtttag tgaaccggcg ccagtcctcc gattgactga gtcgcccggg tacccgtgta | 720 |
| tccaataaac cctcttgcag ttgcatccga cttgtggtct cgctgttcct gggagggtc | 780 |
| tcctctgagt gattgactac ccgtcagcgg gggtctttca tttgggggct cgtccgggat | 840 |
| cgggagaccc ctgcccaggg accaccgacc caccaccggg aggtaagctg gccagcaact | 900 |
| tatctgtgtc tgtccgattg tctagtgtct atgactgatt ttatgcgcct gcgtcggtac | 960 |
| tagttagcta actagctctg tatctggcgg acccgtggtg gaactgacga gttcggaaca | 1020 |
| cccggccgca accctgggag acgtcccagg gacttcgggg gccgttttg tggcccgacc | 1080 |
| tgagtcctaa aatcccgatc gtttaggact ctttggtgca cccccctag aggagggata | 1140 |
| tgtggttctg gtaggagacg agaacctaaa acagttcccg cctccgtctg aattttgct | 1200 |
| ttcggtttgg gaccgaagcc gcgccgcgcg tcttgtctgc tgcagcatcg ttctgtgttg | 1260 |
| tctctgtctg actgtgtttc tgtatttgtc tgaaaatatg ggcccgggct agactgttac | 1320 |
| cactcccta agtttgacct taggtcactg gaaagatgtc gagcggatcg ctcacaacca | 1380 |
| gtcggtagat gtcaagaaga gacgttgggt taccttctgc tctgcagaat ggccaacctt | 1440 |
| taacgtcgga tggccgcgag acggcacctt taaccgagac ctcatcaccc aggttaagat | 1500 |
| caaggtcttt tcacctggcc cgcatggaca cccagaccag gtggggtaca tcgtgacctg | 1560 |
| ggaagccttg gcttttgacc cccctccctg ggtcaagccc tttgtacacc ctaagcctcc | 1620 |
| gcctcctctt cctccatccg ccccgtctct cccccttgaa cctcctcgtt cgaccccgcc | 1680 |
| tcgatcctcc ctttatccag ccctcactcc ttctctaggc gccccccatat ggccatatga | 1740 |
| gatcttatat ggggcacccc cgccccttgt aaacttccct gaccctgaca tgacaagagt | 1800 |
| tactaacagc ccctctctcc aagctcactt acaggctctc tacttagtcc agcacgaagt | 1860 |
| ctggagacct ctggcggcag cctaccaaga acaactggac cgaccggtgg tacctcaccc | 1920 |
| ttaccgagtc ggcgacacag tgtgggtccg ccgacaccag actaagaacc tagaacctcg | 1980 |
| ctggaaagga ccttacacag tcctgctgac cacccccacc gccctcaaag tagacggcat | 2040 |
| cgcagcttgg atacacgccg cccacgtgaa ggctgccgac cccgggggtg gaccatcctc | 2100 |
| tagactgcca tggctcgctc ggtgaccctg gtctttctgg tgcttgtctc actgaccggt | 2160 |
| ttgtatgctg gcctgtgcac cctggtggcc atgctgggag gaggtgctag cggtggtgga | 2220 |
| ggtagcggag gtgaggaag catccagcgt actccaaaga ttcaggttta ctcacgtcat | 2280 |
| ccagcagaga atgaaaagtc aaatttcctg aattgctatg tgtctggggt tcatccatcc | 2340 |
| gacattgaag ttgacttact gaagaatgga gagagaattg aaaaagtgga gcattcagac | 2400 |
| ttgtcttca gcaaggactg gtcttttctat ctccttgtact acactgaatt cacccccact | 2460 |
| gaaaaagatg agtatgcctg ccgtgtgaac catgtgactt tgtcacagcc caagatagtt | 2520 |
| aagtgggatc gagacatggg cggtggtggt tccggtggag gcggtccgg aggtggtgga | 2580 |
| tccggtggtg gaggtagtgg ctctcactcc atgaggtatt tcttcacatc cgtgtcccgg | 2640 |

```
cccggccgcg gggagccccg cttcatcgca gtgggctacg tggacgacac gcagttcgtg   2700
cggttcgaca gcgacgccgc gagccagagg atggagccgc gggcgccgtg gatagagcag   2760
gagggtccgg agtattggga cggggagaca cggaaagtga aggcccactc acagactcac   2820
cgagtggacc tggggaccct gcgcggctac tacaaccaga gcgaggccgg ttctcacacc   2880
gtccagagga tgtatggctg cgacgtgggg tcggactggc gcttcctccg cgggtaccac   2940
cagtacgcct acgacggcaa ggattacatc gccctgaaag aggacctgcg ctcttggacc   3000
gcggcggaca tggcagctca gaccaccaag cacaagtggg aggcggccca tgtggcggag   3060
cagttgagag cctacctgga gggcacgtgc gtggagtggc tccgcagata cctggagaac   3120
gggaaggaga cgctgcagcg cacggacgcc cccaaaacgc atatgactca ccacgctgtc   3180
tctgaccatg aagccaccct gaggtgctgg gccctgagct tctaccctgc ggagatcaca   3240
ctgacctggc agcgggatgg ggaggaccag acccaggaca cggagctcgt ggagaccagg   3300
cctgcagggg atggaacctt ccagaagtgg gcggctgtgg tggtgccttc tggacaggag   3360
cagagataca cctgccatgt gcagcatgag ggtttgccca agcccctcac cctgagatgg   3420
gagccgtctt cccagcccac catccccatc gtgggcatca ttgctggcct ggttctcttt   3480
ggagctgtga tcactggagc tgtggtcgct gctgtgatgt ggaggaggaa gagctcagat   3540
agaaaaggag ggagctactc tcaggctgca agcagtgaca gtgcccaggg ctctgatgtg   3600
tctctcacag cttgtaaagt gtgagcggcc gctggattag tccaatttgt taaagacagg   3660
atatcagtgg tccaggctct agttttgact caacaatatc accagctgaa gcctatagag   3720
tacgagccat agataaaata aagattttta tttagtctcc agaaaagggg gggaatgaaa   3780
gaccccacct gtaggtttgg caagctagct taagtaacgc cattttgcaa ggcatggaaa   3840
aatacataac tgagaataga aagttcaga tcaaggtcag gaacagatgg aacagctgaa   3900
tatgggccaa acaggatatc tgtggtaagc agttcctgcc ccggctcagg gccaagaaca   3960
gatggaacag ctgaatatgg gccaaacagg atatctgtgg taagcagttc ctgccccggc   4020
tcagggccaa gaacagatgg tccccagatg cggtccagcc ctcagcagtt tctagagaac   4080
catcagatgt ttccagggtg ccccaaggac ctgaaatgac cctgtgcctt atttgaacta   4140
accaatcagt tcgcttctcg cttctgttcg cgcgcttctg ctccccgagc tcaataaaag   4200
agcccacaac ccctcactcg gggcgccagt cctccgattg actgagtcgc ccgggtaccc   4260
gtgtatccaa taaccctctt gcagttgca tccgacttgt ggtctcgctg ttccttggga   4320
gggtctcctc tgagtgattg actacccgtc agcggggtc tttcacacat gcagcatgta   4380
tcaaaattaa tttggttttt ttcttaagt atttacatta aatggccata gtgggtaccg   4440
agctcgaatt ccgtaatcat ggtcatagct gtttcctgtg tgaaattgtt atccgctcac   4500
aattccacac aacatacgag ccggaagcat aaagtgtaaa gcctgggtg cctaatgagt   4560 gagctaactc acattaattg cgttgcgctc actgcccgct ttccagtcgg gaaacctgtc   4620
gtgccagctg cattaatgaa tcggccaacg cgcggggaga gcggtttgc gtattgggcg   4680 ctcttccgct tcctcgctca ctgactcgct gcgctcggtc gttcggctgc ggcgagcggt   4740
atcagctcac tcaaaggcgg taatacggtt atccacagaa tcaggggata acgcaggaaa   4800
gaacatgtga gcaaaaggcc agcaaaaggc caggaaccgt aaaaaggccg cgttgctggc   4860
gtttttccat aggctccgcc ccctgacga gcatcacaaa aatcgacgct caagtcagag   4920
gtggcgaaac ccgacaggac tataaagata ccaggcgttt ccccctggaa gctccctcgt   4980
gcgctctcct gttccgaccc tgccgcttac cggatacctg tccgcctttc tcccttcggg   5040
```

```
aagcgtggcg ctttctcaat gctcacgctg taggtatctc agttcggtgt aggtcgttcg    5100
ctccaagctg ggctgtgtgc acgaaccccc cgttcagccc gaccgctgcg ccttatccgg    5160
taactatcgt cttgagtcca acccggtaag acacgactta tcgccactgg cagcagccac    5220
tggtaacagg attagcagag cgaggtatgt aggcggtgct acagagttct tgaagtggtg    5280
gcctaactac ggctacacta aaggacagt atttggtatc tgcgctctgc tgaagccagt    5340
taccttcgga aaagagttg gtagctcttg atccggcaaa caaccaccg ctggtagcgg    5400 tggttttttt gtttgcaagc agcagattac gcgcagaaaa aaggatctc aagaagatcc    5460 tttgatcttt tctacggggt ctgacgctca gtggaacgaa aactcacgtt aagggatttt    5520
ggtcatgaga ttatcaaaaa ggatcttcac ctagatcctt ttaaattaaa aatgaagttt    5580
taaatcaatc taaagtatat atgagtaaac ttggtctgac agttaccaat gcttaatcag    5640
tgaggcacct atctcagcga tctgtctatt tcgttcatcc atagttgcct gactcccgt    5700 cgtgtagata actacgatac gggagggctt accatctggc cccagtgctg caatgatacc    5760
gcgagaccca cgctcaccgg ctccagattt atcagcaata aaccagccag ccggaagggc    5820
cgagcgcaga agtggtcctg caactttatc cgcctccatc cagtctatta attgttgccg    5880
ggaagctaga gtaagtagtt cgccagttaa tagtttgcgc aacgttgttg ccattgctac    5940
aggcatcgtg gtgtcacgct cgtcgtttgg tatggcttca ttcagctccg gttcccaacg    6000
atcaaggcga gttacatgat cccccatgtt gtgcaaaaaa gcggttagct ccttcggtcc    6060
tccgatcgtt gtcagaagta agttggccgc agtgttatca ctcatggtta tggcagcact    6120
gcataattct cttactgtca tgccatccgt aagatgcttt tctgtgactg gtgagtactc    6180
aaccaagtca ttctgagaat agtgtatgcg gcgaccgagt tgctcttgcc cggcgtcaat    6240
acgggataat accgcgccac atagcagaac tttaaaagtg ctcatcattg gaaaacgttc    6300
ttcggggcga aaactctcaa ggatcttacc gctgttgaga tccagttcga tgtaacccac    6360
tcgtgcaccc aactgatctt cagcatcttt tactttcacc agcgtttctg ggtgagcaaa    6420
aacaggaagg caaaatgccg caaaaaaggg aataagggcg acacggaaat gttgaatact    6480
catactcttc ctttttcaat attattgaag catttatcag ggttattgtc tcatgagcgg    6540
atacatattt gaatgtattt agaaaaataa acaataggg gttccgcgca catttccccg    6600
aaaagtgcca cctgacgtct aagaaaccat tattatcatg acattaacct ataaaaatag    6660
gcgtatcacg aggccctttc gtctcgcgcg tttcggtgat gacggtgaaa acctctgaca    6720
catgcagctc ccggagacgg tcacagcttg tctgtaagcg gatgccggga gcagacaagc    6780
ccgtcagggc gcgtcagcgg gtgttggcgg gtgtcggggc tggcttaact atgcggcatc    6840
agagcagatt gtactgagag tgcaccatat gcggtgtgaa ataccgcaca gatgcgtaag    6900
gagaaaatac cgcatcaggc gccattcgcc attcaggctg cgcaactgtt gggaagggcg    6960
atcggtgcgg gcctcttcgc tattacgcca gctggcgaaa gggggatgtg ctgcaaggcg    7020
attaagttgg gtaacgccag ggttttccca gtcacgacgt tgtaaaacga cggccagtcc    7080
```

<210> SEQ ID NO 30
<211> LENGTH: 7080
<212> TYPE: DNA
<213> ORGANISM: Artificial
<220> FEATURE:
<223> OTHER INFORMATION: Synthetic; plasmid
<220> FEATURE:
<221> NAME/KEY: misc_feature
<222> LOCATION: (2170)..(2196)
<223> OTHER INFORMATION: Sequence encoding antigen peptide

```
<220> FEATURE:
<221> NAME/KEY: misc_feature
<222> LOCATION: (2242)..(2538)
<223> OTHER INFORMATION: Sequence encoding beta2-microglobulin
<220> FEATURE:
<221> NAME/KEY: misc_feature
<222> LOCATION: (2599)..(3621)
<223> OTHER INFORMATION: Sequence encoding A2 MHC heavy chain

<400> SEQUENCE: 30
```

| | | | | | |
|---|---|---|---|---|---|
| aagcttccca | ttgcatacgt | tgtatccata | tcataatatg | tacatttata | ttggctcatg | 60 |
| tccaacatta | ccgccatgtt | gacattgatt | attgactagt | tattaatagt | aatcaattac | 120 |
| ggggtcatta | gttcatagcc | catattggag | ttccgcgtta | cataacttac | ggtaaatggc | 180 |
| ccgcctggct | gaccgcccaa | cgaccccgc | ccttgacgt | caataatgac | gtatgttccc | 240 |
| atagtaacgc | caatagggac | tttccattga | cgtcaatggg | tggagtattt | acggtaaact | 300 |
| gcccacttgg | cagtacatca | agtgtatcat | atgccaagta | cgccccctat | tgacgtcaat | 360 |
| gacggtaaat | ggcccgcctg | gcattatgcc | cagtacatga | ccttatggga | ctttcctact | 420 |
| tggcagtaca | tctacgtatt | agtcatcgct | attaccatgg | tgatgcggtt | gtggcagtac | 480 |
| atcaatgggc | gtggatagcg | gtttgactca | cggggatttc | caagtctcca | ccccattgac | 540 |
| gtcaatggga | gtttgttttg | gcaccaaaat | caacgggact | ttccaaaatg | tcgtaacaac | 600 |
| tccgccccat | tgacgcaaat | gggcggtagg | cgtgtacggt | gggaggtcta | tataagcaga | 660 |
| gctcgtttag | tgaaccggcg | ccagtcctcc | gattgactga | gtcgcccggg | tacccgtgta | 720 |
| tccaataaac | cctcttgcag | ttgcatccga | cttgtggtct | cgctgttcct | tgggagggtc | 780 |
| tcctctgagt | gattgactac | ccgtcagcgg | gggtctttca | tttgggggct | cgtccgggat | 840 |
| cgggagaccc | ctgcccaggg | accaccgacc | caccaccggg | aggtaagctg | gccagcaact | 900 |
| tatctgtgtc | tgtccgattg | tctagtgtct | atgactgatt | ttatgcgcct | gcgtcggtac | 960 |
| tagttagcta | actagctctg | tatctggcgg | acccgtggtg | gaactgacga | gttcggaaca | 1020 |
| cccggccgca | accctgggag | acgtcccagg | gacttcgggg | gccgttttttg | tggcccgacc | 1080 |
| tgagtcctaa | aatcccgatc | gtttaggact | cttttggtgca | cccccttag | aggagggata | 1140 |
| tgtggttctg | gtaggagacg | agaacctaaa | acagttcccg | cctccgtctg | aatttttgct | 1200 |
| ttcggtttgg | gaccgaagcc | gcgccgcgcg | tcttgtctgc | tgcagcatcg | ttctgtgttg | 1260 |
| tctctgtctg | actgtgtttc | tgtatttgtc | tgaaaatatg | ggcccgggct | agactgttac | 1320 |
| cactcccttla | agtttgacct | taggtcactg | gaaagatgtc | gagcggatcg | ctcacaacca | 1380 |
| gtcggtagat | gtcaagaaga | gacgttgggt | taccttctgc | tctgcagaat | ggccaacctt | 1440 |
| taacgtcgga | tggccgcgag | acggcacctt | taaccgagac | ctcatcaccc | aggttaagat | 1500 |
| caaggtctttt | tcacctggcc | cgcatggaca | cccagaccag | gtggggtaca | tcgtgacctg | 1560 |
| ggaagccttg | gcttttgacc | cccctccctg | ggtcaagccc | tttgtacacc | ctaagcctcc | 1620 |
| gcctcctctt | cctccatccg | ccccgtctct | cccccttgaa | cctcctcgtt | cgaccccgcc | 1680 |
| tcgatcctcc | ctttatccag | ccctcactcc | ttctctaggc | gccccatat | ggccatatga | 1740 |
| gatcttatat | ggggcacccc | cgccccttgt | aaacttccct | gaccctgaca | tgacaagagt | 1800 |
| tactaacagc | ccctctctcc | aagctcactt | acaggctctc | tacttagtcc | agcacgaagt | 1860 |
| ctggagacct | ctggcggcag | cctaccaaga | caactggacg | gaccggtgg | tacctcaccc | 1920 |
| ttaccgagtc | ggcgacacag | tgtgggtccg | ccgacaccag | actaagaacc | tagaacctcg | 1980 |
| ctggaaagga | ccttacacag | tcctgctgac | caccccacc | gccctcaaag | tagacggcat | 2040 |
| cgcagcttgg | atacacgccg | cccacgtgaa | ggctgccgac | cccggggggtg | gaccatcctc | 2100 |

```
tagactgcca tggctcgctc ggtgaccctg gtctttctgg tgcttgtctc actgaccggt    2160
ttgtatgcta tcatggacca ggtgcctttc tccgtgggag gaggtgctag cggtggtgga    2220
ggtagcggag gtggaggaag catccagcgt actccaaaga ttcaggttta ctcacgtcat    2280
ccagcagaga atggaaagtc aaatttcctg aattgctatg tgtctggtt tcatccatcc     2340 gacattgaag ttgacttact gaagaatgga gagagaattg aaaaagtgga gcattcagac    2400
ttgtctttca gcaaggactg gtctttctat ctcttgtact acactgaatt caccccccact   2460 gaaaaagatg agtatgcctg ccgtgtgaac catgtgactt tgtcacagcc caagatagtt    2520
aagtgggatc gagacatggg cggtggtggt tccggtggag gcggttccgg aggtggtgga    2580
tccggtggtg gaggtagtgg ctctcactcc atgaggtatt tcttcacatc cgtgtcccgg    2640
cccggccgcg gggagccccg cttcatcgca gtgggctacg tggacgacac gcagttcgtg    2700
cggttcgaca cgcacgccgc gagccagagg atggagccgc gggcgccgtg gatagagcag    2760
gagggtccgg agtattggga cggggagaca cggaaagtga aggcccactc acagactcac    2820
cgagtggacc tggggaccct gcgcggctac tacaaccaga gcgaggccgg ttctcacacc    2880
gtccagagga tgtatggctg cgacgtgggg tcggactggc gcttcctccg cgggtaccac    2940
cagtacgcct acgacggcaa ggattacatc gccctgaaag aggacctgcg ctcttggacc    3000
gcggcggaca tggcagctca gaccaccaag cacaagtggg aggcggccca tgtggcggag    3060
cagttgagag cctacctgga gggcacgtgc gtggagtggc tccgcagata cctggagaac    3120
gggaaggaga cgctgcagcg cacggacgcc cccaaaacgc atatgactca ccacgctgtc    3180
tctgaccatg aagccaccct gaggtgctgg gccctgagct ctacctgc ggagatcaca     3240 ctgacctggc agcgggatgg ggaggaccag acccaggaca cggagctcgt ggagaccagg    3300
cctgcagggg atggaacctt ccagaagtgg gcggctgtgg tggtgccttc tggacaggag    3360
cagagataca cctgccatgt gcagcatgag gtttgccca gcccctcac cctgagatgg      3420 gagccgtctt cccagcccac catccccatc gtgggcatca ttgctggcct ggttctcttt    3480
ggagctgtga tcactggagc tgtggtcgct gctgtgatgt ggaggaggaa gagctcagat    3540
agaaaaggag ggagctactc tcaggctgca agcagtgaca gtgcccaggg ctctgatgtg    3600
tctctcacag cttgtaaagt gtgagcggcc gctggattag tccaatttgt taaagacagg    3660
atatcagtgg tccaggctct agttttgact caacaatatc accagctgaa gcctatagag    3720
tacgagccat agataaaata aaagatttta tttagtctcc agaaaaaggg gggaatgaaa    3780
gaccccacct gtaggtttgg caagctagct taagtaacgc cattttgcaa ggcatggaaa    3840
aatacataac tgagaataga aagttcaga tcaaggtcag gaacagatgg aacagctgaa    3900
tatgggccaa acaggatatc tgtggtaagc agttcctgcc ccggctcagg gccaagaaca    3960 gatgaacag ctgaatatgg gccaaacagg atatctgtgg taagcagttc ctgccccggc     4020
tcagggccaa gaacagatgg tccccagatg cggtccagcc ctcagcagtt tctagagaac    4080
catcagatgt ttccaggtg ccccaaggac ctgaaatgac cctgtgcctt atttgaacta     4140
accaatcagt tcgcttctcg cttctgttcg cgcgcttctg ctccccgagc tcaataaaag    4200
agcccacaac ccctcactcg gggcgccagt cctccgattg actgagtcgc ccgggtaccc    4260
gtgtatccaa taaaccctct tgcagttgca tccgacttgt ggtctcgctg ttccttggga    4320
gggtctcctc tgagtgattg actacccgtc agcgggggtc tttcacacat gcagcatgta    4380
tcaaaattaa tttggttttt tttcttaagt atttacatta aatggccata gtgggtaccg    4440
agctcgaatt ccgtaatcat ggtcatagct gtttcctgtg tgaaattgtt atccgctcac    4500
```

```
aattccacac aacatacgag ccggaagcat aaagtgtaaa gcctggggtg cctaatgagt      4560
gagctaactc acattaattg cgttgcgctc actgcccgct ttccagtcgg gaaacctgtc      4620
gtgccagctg cattaatgaa tcggccaacg cgcggggaga ggcggtttgc gtattgggcg      4680
ctcttccgct tcctcgctca ctgactcgct gcgctcggtc gttcggctgc ggcgagcggt      4740
atcagctcac tcaaaggcgg taatacggtt atccacagaa tcaggggata acgcaggaaa      4800
gaacatgtga gcaaaaggcc agcaaaaggc caggaaccgt aaaaaggccg cgttgctggc      4860
gtttttccat aggctccgcc ccctgacga gcatcacaaa aatcgacgct caagtcagag       4920
gtggcgaaac ccgacaggac tataaagata ccaggcgttt ccccctggaa gctccctcgt      4980
gcgctctcct gttccgaccc tgccgcttac cggatacctg tccgcctttc tcccttcggg      5040
aagcgtggcg ctttctcaat gctcacgctg taggtatctc agttcggtgt aggtcgttcg      5100
ctccaagctg ggctgtgtgc acgaaccccc cgttcagccc gaccgctgcg ccttatccgg      5160
taactatcgt cttgagtcca acccggtaag acacgactta tcgccactgg cagcagccac      5220
tggtaacagg attagcagag cgaggtatgt aggcggtgct acagagttct tgaagtggtg      5280
gcctaactac ggctacacta aggacagt atttggtatc tgcgctctgc tgaagccagt       5340
taccttcgga aaagagttg gtagctcttg atccggcaaa caaaccaccg ctggtagcgg       5400
tggttttttt gtttgcaagc agcagattac gcgcagaaaa aaaggatctc aagaagatcc      5460
tttgatcttt tctacggggt ctgacgctca gtggaacgaa aactcacgtt aagggatttt      5520
ggtcatgaga ttatcaaaaa ggatcttcac ctagatcctt ttaaattaaa aatgaagttt      5580
taaatcaatc taaagtatat atgagtaaac ttggtctgac agttaccaat gcttaatcag      5640
tgaggcacct atctcagcga tctgtctatt tcgttcatcc atagttgcct gactccccgt      5700
cgtgtagata actacgatac gggagggctt accatctggc cccagtgctg caatgatacc      5760
gcgagaccca cgctcaccgg ctccagattt atcagcaata aaccagccag ccggaagggc      5820
cgagcgcaga agtggtcctg caactttatc cgcctccatc cagtctatta attgttgccg      5880
ggaagctaga gtaagtagtt cgccagttaa tagtttcgcc aacgttgttg ccattgctac      5940
aggcatcgtg gtgtcacgct cgtcgtttgg tatggcttca ttcagctccg gttcccaacg      6000
atcaaggcga gttacatgat cccccatgtt gtgcaaaaaa gcggttagct ccttcggtcc      6060
tccgatcgtt gtcagaagta agttggccgc agtgttatca ctcatggtta tggcagcact      6120
gcataattct cttactgtca tgccatccgt aagatgcttt tctgtgactg gtgagtactc      6180
aaccaagtca ttctgagaat agtgtatgcg gcgaccgagt tgctcttgcc cggcgtcaat      6240 acggataat accgcgccac atagcagaac tttaaaagtg ctcatcattg gaaaacgttc       6300
ttcggggcga aaactctcaa ggatcttacc gctgttgaga tccagttcga tgtaacccac      6360
tcgtgcaccc aactgatctt cagcatcttt tactttcacc agcgtttctg ggtgagcaaa      6420
aacaggaagg caaaatgccg caaaaaaggg aataagggcg acacggaaat gttgaatact      6480
catactcttc cttttcaat attattgaag catttatcag ggttattgtc tcatgagcgg       6540
atacatattt gaatgtattt agaaaaataa acaataggg gttccgcgca catttccccg       6600
aaaagtgcca cctgacgtct aagaaaccat tattatcatg acattaacct ataaaaatag      6660
gcgtatcacg aggcccttc gtctcgcgcg tttcggtgat gacggtgaaa acctctgaca       6720
catgcagctc ccggagacgg tcacagcttg tctgtaagcg gatgccggga gcagacaagc      6780
ccgtcagggc gcgtcagcgg gtgttggcgg gtgtcggggc tggcttaact atgcggcatc      6840
agagcagatt gtactgagag tgcaccatat gcggtgtgaa ataccgcaca gatgcgtaag      6900
```

| | |
|---|---|
| gagaaaatac cgcatcaggc gccattcgcc attcaggctg cgcaactgtt gggaagggcg | 6960 |
| atcggtgcgg gcctcttcgc tattacgcca gctggcgaaa gggggatgtg ctgcaaggcg | 7020 |
| attaagttgg gtaacgccag ggttttccca gtcacgacgt tgtaaaacga cggccagtcc | 7080 |

<210> SEQ ID NO 31
<211> LENGTH: 7080
<212> TYPE: DNA
<213> ORGANISM: Artificial
<220> FEATURE:
<223> OTHER INFORMATION: Synthetic; plasmid
<220> FEATURE:
<221> NAME/KEY: misc_feature
<222> LOCATION: (2170)..(2196)
<223> OTHER INFORMATION: Sequence encoding antigen peptide
<220> FEATURE:
<221> NAME/KEY: misc_feature
<222> LOCATION: (2242)..(2538)
<223> OTHER INFORMATION: Sequence encoding beta2-microglobulin
<220> FEATURE:
<221> NAME/KEY: misc_feature
<222> LOCATION: (2599)..(3621)
<223> OTHER INFORMATION: Sequence encoding A2 MHC heavy chain

<400> SEQUENCE: 31

| | |
|---|---|
| aagcttccca ttgcatacgt tgtatccata tcataatatg tacatttata ttggctcatg | 60 |
| tccaacatta ccgccatgtt gacattgatt attgactagt tattaatagt aatcaattac | 120 |
| ggggtcatta gttcatagcc catattggag ttccgcgtta cataacttac ggtaaatggc | 180 |
| ccgcctggct gaccgcccaa cgaccccgc cccttgacgt caataatgac gtatgttccc | 240 |
| atagtaacgc caatagggac tttccattga cgtcaatggg tggagtattt acggtaaact | 300 |
| gcccacttgg cagtacatca agtgtatcat atgccaagta cgccccctat tgacgtcaat | 360 |
| gacggtaaat ggcccgcctg gcattatgcc cagtacatga ccttatggga ctttcctact | 420 |
| tggcagtaca tctacgtatt agtcatcgct attaccatgg tgatgcggtt gtggcagtac | 480 |
| atcaatgggc gtggatagcg gtttgactca cggggatttc caagtctcca ccccattgac | 540 |
| gtcaatggga gtttgttttg gcaccaaaat caacgggact ttccaaaatg tcgtaacaac | 600 |
| tccgccccat tgacgcaaat gggcggtagg cgtgtacggt gggaggtcta taagcaga | 660 |
| gctcgtttag tgaaccggcg ccagtcctcc gattgactga gtcgcccggg tacccgtgta | 720 |
| tccaataaac cctcttgcag ttgcatccga cttgtggtct cgctgttcct tgggagggtc | 780 |
| tcctctgagt gattgactac ccgtcagcgg gggtctttca tttgggggct cgtccgggat | 840 |
| cgggagaccc ctgcccaggg accaccgacc caccaccggg aggtaagctg gccagcaact | 900 |
| tatctgtgtc tgtccgattg tctagtgtct atgactgatt ttatgcgcct gcgtcggtac | 960 |
| tagttagcta actagctctg tatctggcgg acccgtggtg gaactgacga gttcggaaca | 1020 |
| cccggccgca accctgggag acgtcccagg gacttcgggg gccgtttttg tggcccgacc | 1080 |
| tgagtcctaa aatcccgatc gtttaggact ctttggtgca ccccccttag aggagggata | 1140 |
| tgtggttctg gtaggagacg agaacctaaa acagttcccg cctccgtctg aattttttgct | 1200 |
| ttcggtttgg gaccgaagcc gcgccgcgcg tcttgtctgc tgcagcatcg ttctgtgttg | 1260 |
| tctctgtctg actgtgtttc tgtatttgtc tgaaaatatg ggcccgggct agactgttac | 1320 |
| cactcccta agtttgaccct taggtcactg gaaagatgtc gagcggatcg ctcacaacca | 1380 |
| gtcggtagat gtcaagaaga gacgttgggt taccttctgc tctgcagaat ggccaacctt | 1440 |
| taacgtcgga tggccgcgag acggcacctt taaccgagac ctcatcaccc aggttaagat | 1500 |
| caaggtcttt tcacctggcc cgcatggaca cccagaccag gtggggtaca tcgtgacctg | 1560 |

```
ggaagccttg gcttttgacc cccctccctg ggtcaagccc tttgtacacc ctaagcctcc    1620
gcctcctctt cctccatccg ccccgtctct cccccttgaa cctcctcgtt cgaccccgcc    1680
tcgatcctcc ctttatccag ccctcactcc ttctctaggc gcccccatat ggccatatga    1740
gatcttatat ggggcacccc cgcccttgt aaacttccct gaccctgaca tgacaagagt     1800
tactaacagc ccctctctcc aagctcactt acaggctctc tacttagtcc agcacgaagt    1860
ctggagacct ctggcggcag cctaccaaga acaactggac cgaccggtgg tacctcaccc    1920
ttaccgagtc ggcgacacag tgtgggtccg ccgacaccag actaagaacc tagaacctcg    1980
ctggaaagga ccttacacag tcctgctgac caccccacc gccctcaaag tagacggcat     2040
cgcagcttgg atacgcgcg cccacgtgaa ggctgccgac cccgggggtg gaccatcctc     2100
tagactgcca tggctcgctc ggtgaccctg gtctttctgg tgcttgtctc actgaccggt    2160
ttgtatgctt attggagcc cgggcctgtg actgtaggag gaggtgctag cggtggtgga     2220
ggtagcggag gtggaggaag catccagcgt actccaaaga ttcaggttta ctcacgtcat    2280
ccagcagaga atggaaagtc aaatttcctg aattgctatg tgtctgggtt tcatccatcc    2340
gacattgaag ttgacttact gaagaatgga gagagaattg aaaaagtgga gcattcagac    2400
ttgtctttca gcaaggactg gtcttttctat ctcttgtact acactgaatt cacccccact    2460
gaaaaagatg agtatgcctg ccgtgtgaac catgtgactt tgtcacagcc caagatagtt    2520
aagtgggatc gagacatggg cggtggtggt tccggtggag gcggttccgg aggtggtgga    2580
tccggtggtg gaggtagtgg ctctcactcc atgaggtatt tcttcacatc cgtgtcccgg    2640
cccggccgcg gggagccccg cttcatcgca gtgggctacg tggacgacac gcagttcgtg    2700
cggttcgaca cgcgacgccg cgagccagag gatggagccg cgggcgccgtg gatagagcag    2760 gagggtccgg agtattggga cggggagaca cggaaagtga aggcccactc acagactcac    2820
cgagtggacc tggggaccct gcgcggctac tacaaccaga gcgaggccgg ttctcacacc    2880
gtccagagga tgtatggctg cgacgtgggg tcggactggc gcttcctccg cgggtaccac    2940
cagtacgcct acgacggcaa ggattacatc gccctgaaag aggacctgcg ctcttggacc    3000
gcggcggaca tggcagctca gaccaccaag cacaagtggg aggcggccca tgtggcggag    3060
cagttgagag cctacctgga gggcacgtgc gtggagtggc tccgcagata cctggagaac    3120
gggaaggaga cgctgcagcg cacggacgcc cccaaaacgc atatgactca ccacgctgtc    3180
tctgaccatg aagccaccct gaggtgctgg gccctgagct tctacctgc ggagatcaca     3240 ctgacctggc agcgggatgg ggaggaccag acccaggaca cggagctcgt ggagaccagg    3300
cctgcagggg atggaacctt ccagaagtgg gcggctgtgg tggtgccttc tggacaggag    3360
cagagataca cctgccatgt gcagcatgag ggtttgccca gcccctcac cctgagatgg     3420 gagccgtctt cccagcccac catccccatc gtgggcatca ttgctggcct ggttctcttt    3480
ggagctgtga tcactggagc tgtggtcgct gctgtgatgt ggaggaggaa gagctcagat    3540
agaaaaggag ggagctactc tcaggctgca agcagtgaca gtgcccaggg ctctgatgtg    3600
tctctcacag cttgtaaagt gtgagcggcc gctggattag tccaatttgt taaagacagg    3660
atatcagtgg tccaggctct agttttgact caacaatatc accagctgaa gcctatagag    3720
tacgagccat agataaaata aaagattta tttagtctcc agaaaaggg gggaatgaaa      3780 gacccccacct gtaggtttgg caagctagct taagtaacgc cattttgcaa ggcatggaaa   3840
aatacataac tgagaataga gaagttcaga tcaaggtcag gaacagatgg aacagctgaa    3900
tatgggccaa acaggatatc tgtggtaagc agttcctgcc ccggctcagg gccaagaaca    3960
```

```
gatggaacag ctgaatatgg gccaaacagg atatctgtgg taagcagttc ctgccccggc    4020
tcagggccaa gaacagatgg tccccagatg cggtccagcc ctcagcagtt tctagagaac    4080
catcagatgt ttccagggtg ccccaaggac ctgaaatgac cctgtgcctt atttgaacta    4140
accaatcagt tcgcttctcg cttctgttcg cgcgcttctg ctccccgagc tcaataaaag    4200
agcccacaac ccctcactcg gggcgccagt cctccgattg actgagtcgc ccgggtaccc    4260
gtgtatccaa taaaccctct tgcagttgca tccgacttgt ggtctcgctg ttccttggga    4320
gggtctcctc tgagtgattg actacccgtc agcggggtc tttcacacat gcagcatgta    4380
tcaaaattaa tttggttttt tttcttaagt atttacatta aatggccata gtgggtaccg    4440
agctcgaatt ccgtaatcat ggtcatagct gtttcctgtg tgaaattgtt atccgctcac    4500
aattccacac aacatacgag ccggaagcat aaagtgtaaa gcctggggtg cctaatgagt    4560
gagctaactc acattaattg cgttgcgctc actgcccgct ttccagtcgg gaaacctgtc    4620
gtgccagctg cattaatgaa tcggccaacg cgcggggaga gcggtttgc gtattgggcg    4680 ctcttccgct tcctcgctca ctgactcgct gcgctcggtc gttcggctgc ggcgagcggt    4740
atcagctcac tcaaaggcgg taatacggtt atccacagaa tcaggggata acgcaggaaa    4800
gaacatgtga gcaaaaggcc agcaaaaggc caggaaccgt aaaaaggccg cgttgctggc    4860
gtttttccat aggctccgcc ccctgacga gcatcacaaa aatcgacgct caagtcagag    4920
gtggcgaaac ccgacaggac tataaagata ccaggcgttt ccccctggaa gctccctcgt    4980
gcgctctcct gttccgaccc tgccgcttac cggatacctg tccgcctttc tcccttcggg    5040
aagcgtggcg ctttctcaat gctcacgctg taggtatctc agttcggtgt aggtcgttcg    5100
ctccaagctg ggctgtgtgc acgaacccc cgttcagccc gaccgctgcg ccttatccgg    5160
taactatcgt cttgagtcca acccggtaag acacgactta tcgccactgg cagcagccac    5220
tggtaacagg attagcagag cgaggtatgt aggcggtgct acagagttct tgaagtggtg    5280
gcctaactac ggctacacta gaaggacagt atttggtatc tgcgctctgc tgaagccagt    5340
taccttcgga aaaagagttg gtagctcttg atccggcaaa caaaccaccg ctggtagcgg    5400 tggtttttt gtttgcaagc agcagattac gcgcagaaaa aaaggatctc aagaagatcc    5460
tttgatcttt tctacggggt ctgacgctca gtggaacgaa aactcacgtt aagggatttt    5520
ggtcatgaga ttatcaaaaa ggatcttcac ctagatcctt ttaaattaaa aatgaagttt    5580
taaatcaatc taaagtatat atgagtaaac ttggtctgac agttaccaat gcttaatcag    5640
tgaggcacct atctcagcga tctgtctatt tcgttcatcc atagttgcct gactccccgt    5700
cgtgtagata actacgatac gggagggctt accatctggc cccagtgctg caatgatacc    5760
gcgagaccca cgctcaccgg ctccagattt atcagcaata accagccag ccggaagggc    5820 cgagcgcaga gtggtcctg caactttatc cgcctccatc cagtctatta attgttgccg    5880
ggaagctaga gtaagtagtt cgccagttaa tagtttgcgc aacgttgttg ccattgctac    5940
aggcatcgtg gtgtcacgct cgtcgtttgg tatggcttca ttcagctccg gttcccaacg    6000
atcaaggcga gttacatgat cccccatgtt gtgcaaaaaa gcggttagct ccttcggtcc    6060
tccgatcgtt gtcagaagta agttggccgc agtgttatca ctcatggtta tggcagcact    6120
gcataattct cttactgtca tgccatccgt aagatgcttt tctgtgactg gtgagtactc    6180
aaccaagtca ttctgagaat agtgtatgcg gcgaccgagt tgctcttgcc cggcgtcaat    6240
acgggataat accgcgccac atagcagaac tttaaaagtg ctcatcattg gaaaacgttc    6300
ttcggggcga aaactctcaa ggatcttacc gctgttgaga tccagttcga tgtaacccac    6360
```

-continued

```
tcgtgcaccc aactgatctt cagcatcttt tactttcacc agcgtttctg ggtgagcaaa    6420
aacaggaagg caaatgccg caaaaaggg aataagggcg acacggaaat gttgaatact    6480
catactcttc cttttcaat attattgaag catttatcag ggttattgtc tcatgagcgg    6540
atacatattt gaatgtattt agaaaaataa acaaataggg gttccgcgca catttccccg    6600
aaaagtgcca cctgacgtct aagaaaccat tattatcatg acattaacct ataaaaatag    6660
gcgtatcacg aggccctttc gtctcgcgcg tttcggtgat gacggtgaaa acctctgaca    6720
catgcagctc ccggagacgg tcacagcttg tctgtaagcg gatgccggga gcagacaagc    6780
ccgtcagggc gcgtcagcgg gtgttggcgg gtgtcggggc tggcttaact atgcggcatc    6840
agagcagatt gtactgagag tgcaccatat gcggtgtgaa ataccgcaca gatgcgtaag    6900
gagaaaatac cgcatcaggc gccattcgcc attcaggctg cgcaactgtt gggaagggcg    6960
atcggtgcgg gcctcttcgc tattacgcca gctggcgaaa gggggatgtg ctgcaaggcg    7020
attaagttgg gtaacgccag ggttttccca gtcacgacgt tgtaaaacga cggccagtcc    7080
```

<210> SEQ ID NO 32
<211> LENGTH: 108
<212> TYPE: DNA
<213> ORGANISM: Artificial
<220> FEATURE:
<223> OTHER INFORMATION: Synthetic

<400> SEQUENCE: 32

```
ccggccgtag acggcatcgc agcttggata cacgccgccc acgtgaaggc tgccgacccc    60
gggggtggac catcctctag actgccatgg ctcgctcggt gaccctgg                 108
```

<210> SEQ ID NO 33
<211> LENGTH: 33
<212> TYPE: DNA
<213> ORGANISM: Artificial
<220> FEATURE:
<223> OTHER INFORMATION: Synthetic

<400> SEQUENCE: 33

```
cgcgcggcgg ccgctcacac tttacaagct gtg                                 33
```

<210> SEQ ID NO 34
<211> LENGTH: 64
<212> TYPE: DNA
<213> ORGANISM: Artificial
<220> FEATURE:
<223> OTHER INFORMATION: Synthetic

<400> SEQUENCE: 34

```
ctgaccggtt tgtatgctaa cctggtgcca atggtggcta ccgtgggagg aggtgctagc    60
ggtg                                                                 64
```

<210> SEQ ID NO 35
<211> LENGTH: 64
<212> TYPE: DNA
<213> ORGANISM: Artificial
<220> FEATURE:
<223> OTHER INFORMATION: Synthetic

<400> SEQUENCE: 35

```
caccgctagc acctcctccc acggtagcca ccattggcac cagggtagca tacaaaccgg    60
tcag                                                                 64
```

```
<210> SEQ ID NO 36
<211> LENGTH: 64
<212> TYPE: DNA
<213> ORGANISM: Artificial
<220> FEATURE:
<223> OTHER INFORMATION: Synthetic

<400> SEQUENCE: 36
ctgaccggtt tgtatgctgg cctgtgcacc ctggtggcca tgctgggagg aggtgctagc    60
ggtg                                                                 64

<210> SEQ ID NO 37
<211> LENGTH: 64
<212> TYPE: DNA
<213> ORGANISM: Artificial
<220> FEATURE:
<223> OTHER INFORMATION: Synthetic

<400> SEQUENCE: 37
caccgctagc acctcctccc agcatggcca ccagggtgca caggccagca tacaaaccgg    60
tcag                                                                 64

<210> SEQ ID NO 38
<211> LENGTH: 64
<212> TYPE: DNA
<213> ORGANISM: Artificial
<220> FEATURE:
<223> OTHER INFORMATION: Synthetic

<400> SEQUENCE: 38
ctgaccggtt tgtatgctat catggaccag gtgcctttct ccgtgggagg aggtgctagc    60
ggtg                                                                 64

<210> SEQ ID NO 39
<211> LENGTH: 63
<212> TYPE: DNA
<213> ORGANISM: Artificial
<220> FEATURE:
<223> OTHER INFORMATION: Synthetic

<400> SEQUENCE: 39
accgctagca cctcctccca cggagaaagg cacctggtcc atgatagcat acaaaccggt    60
cag                                                                  63

<210> SEQ ID NO 40
<211> LENGTH: 9
<212> TYPE: PRT
<213> ORGANISM: Artificial
<220> FEATURE:
<223> OTHER INFORMATION: Synthetic

<400> SEQUENCE: 40

Tyr Pro His Gly Met Pro Thr Asn Leu
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic

<400> SEQUENCE: 41

Tyr Pro Asn Val Asn Ile His Asn Phe
1               5
```

```
<210> SEQ ID NO 42
<211> LENGTH: 4
<212> TYPE: PRT
<213> ORGANISM: Artificial Sequence
<220> FEATURE:
<223> OTHER INFORMATION: Synthetic

<400> SEQUENCE: 42

Ser Ile Tyr Arg
1
```

SINGLE CHAIN TRIMERS AND USES THEREFOR

PRIORITY

This application is a Divisional of and claims the benefit of priority to U.S. Nonprovisional application Ser. No. 11/397,377, filed Apr. 4, 2006, which is pending, and which is incorporated herein by reference in its entirety.

GOVERNMENT RIGHTS

This invention was made with the support of Grants AI19687, AI42793 and AI46553 from the National Institutes of Health. The government of the United States of America has certain rights in this work.

REFERENCE TO A SEQUENCE LISTING

The Sequence Listing, which is a part of the present disclosure, includes a text file comprising primer nucleotide and/or amino acid sequences of the present invention on a compact disc. The subject matter of the Sequence Listing is incorporated herein by reference in its entirety.

INTRODUCTION

Responses of the immune system to foreign antigens involve, in part, presentation of antigenic peptides to antigen-specific T cells such as CD8 by antigen presenting cells (APCs). Antigenic peptides can be presented on APCs (which include many cell types, including "professional APC's" such as dendritic cells) by cell surface molecules comprising three non-covalently linked components: an antigenic peptide, a Class I major histocompatability complex (MHC) polypeptide, and a β2-microglobulin polypeptide (reviewed in Fundamental Immunology, 2d Ed., W. E. Paul, ed., Ravens Press N.Y. 1989).

$CD8^+$ T cells have numerous clinical, research and therapeutic uses. In particular, cellular immunotherapy methods, such as adoptive T cell immunotherapy, can involve administering to a patient about one billion antigen-specific $CD8^+$ T cells. However, presently practiced methods, such as the Rapid Expansion Method (REM) require at least 3 months following establishment of an ex vivo culture of a patient's T cells to generate sufficient numbers of antigen-specific $CD8^+$ T cells (Riddell, S., et al., J. Immunol. Methods 128: 189-201, 1990; Blattman, J. N., et al., Science 305: 200-205, 2004).

Initial methods that attempted to selectively expand antigen-specific CD8+ T cells required single cell cloning. This approach requires a prolonged culture period of in vitro antigen-driven selection followed by a period of (non-specific) expansion with anti-CD3 monoclonal antibody to generate sufficient numbers of antigen-specific CD8+ T cells. As described by the rapid expansion method (REM), this typically requires 3-4 months to generate one billion antigen-specific T cells. A recent approach taken by NIH investigators uses a modified REM to treat patients with melanoma. Melanoma metastases are surgically resected from individual patients and T cells are isolated ex vivo from each tumor and cultured in the presence of IL-2 only in microtiter trays. Each well exhibiting growth is tested for antigen-specificity using standard cytokine release assays. Wells that exhibit melanoma reactivity are then expanded through multiple rounds of REM. The T cells are infused to the patient generally 2-4 months later.

Other methods employing anti-CD3 monoclonal antibody based strategies to activate and promote the in vitro expansion of T cells have been described. One approach employs paramagnetic beads coated with activating combinations of antibodies and/or proteins (such as anti-CD3/anti-CD28) which induce significant polyclonal activation of α/β T cells. A second variation involves using the anti-CD3/anti-CD28 combination in the presence of CD137 ligand (aka 4-IBBL) with K562 cells to propagate human CD8+ T cells. One limitation of these approaches using anti-CD3 monoclonal antibodies is the lack of enrichment for antigen-specific T cell responses. Long term cultures propagated using this technology (either REM or anti-CD3/anti-CD28 methods) require a prior enrichment step to obtain antigen-specific T cells in sufficient numbers for therapeutic use. Sufficient numbers for therapeutic use are generally thought to be a minimum of one billion T cells ($1\times10^9$ cells). One variation of this approach is to employ HLA class I-immunoglobulin protein dimers coupled to paramagnetic beads in place of anti-CD3 monoclonal antibody. The HLA class I molecule is loaded with exogenous peptide. The peptide loaded magnetic beads (with anti-CD28 immobilized) are then added to purified CD8+ T cells every week to stimulate growth. This strategy results in selective enrichment and growth but generally requires >2 months of repeated stimulations done weekly.

One additional method describes an artificial antigen presenting cell (murine NIH 3T3) transfected with multiple (6 genes) constructs encoding HLA class I allele, human β2-microbulin, CD54, CD58, CD80 and antigen. Human CD8+ T cells can be selectively grown by this method and expanded up to $3\times10^7$ total cells after multiple weekly rounds of stimulation. Additional data presented using this method supports some degree of enrichment over an extended period (3 months) of culture.

An MHC heavy chain comprises about 350 amino acids; a β2-microglobulin comprises about 100 amino acids; and an antigen peptide having a length of from about 8 to about 15 amino acids. The class I heavy chains are encoded by genes of the major histocompatability complex, designated HLA-A, -B and -C in humans, and H-2K, D, and L in mice. The class I heavy chains and β2-microglobulin are separately encoded on different chromosomes. Antigen peptides are normally processed by APCs from protein sources such as, for example, viruses, bacteria, or cancer cells. Diverse variants have been identified for the polypeptides encoded by the HLA-A, -B and -C MHC genes in humans, as well as the murine H-2K, D, and L MHC genes.

Previously, covalently fused components of MHC molecules have been used to stimulate T cells. For example, Mottez et al. (J. Exp. Med. 181: 493-502, 1995) reported producing soluble $K^d$ MHC-peptide fusions comprising a single polypeptide chain comprising, in amino-to-carboxyl terminal order, a $K^d$ antigen peptide, an extracellular portion of a heavy chain of a murine $K^d$ class I heavy chain, and a β2-microglobulin polypeptide. The peptide-Kd sequence was linked to the β2-microglobulin sequence by a 15 residue spacer. Cells expressing these constructs were shown to be immunogens capable of inducing specific murine cytotoxic T cells. However, the antigen peptide does not stably bind to the heavy chain (Madden et al. Cell 70: 1035-1048, 1992; Matsumura et al., Science 257: 927-934, 1992).

In one approach, β2-microglobulin has been coupled to the amino terminals of different class I MHC molecules with a linker (Mage et al., Proc. Natl. Acad. Sci. USA 89: 10658-10662, 1992; Toshitani et al, 1996; Chung et al, 1999). In addition, antigen peptide covalently attached to free β2-microglobulin has been reported (Uger and Barber, The Journal of Immunology 160: 1598-1605, 1998; Uger et al., The Journal of Immunology 162, pp. 6024-6028, 1999; White et al., J. Immunol. 162: 2671-2676, 1999).

PCT Patent application WO 96/04314 discloses "fusion complexes" of MHC molecules in which a presenting peptide is covalently bound to an MHC heavy chain such a class II heavy chain. In some embodiments, the MHC fusion complexes include a flexible linker sequence interposed between the MHC molecule and the presenting peptide. However, WO 96/04314 does not describe a single-chain fusion polypeptide comprising an antigen peptide, a β2-microglobulin and a class I heavy chain.

U.S. Pat. No. 6,011,146 to Mottez discloses an altered MHC class I determining comprising $\alpha_1$, $\alpha_2$, $\alpha_3$ β2-microglobulin polypeptide domains encoded by a mammalian MHC class I locus in which the $\alpha_3$ domain is covalently linked to the β2-microglobulin domain. This patent does not describe a single chain trimer comprising an antigen peptide sequence, a β2-microglobulin sequence and a class I heavy chain sequence as set forth below.

U.S. Pat. No. 4,478,823 discloses an immunologically active preparation comprising an antigenic material in combination with an MHC antigen, including an MHC-β2-microglobulin complex combined with further antigenic material. This patent does not describe a single chain trimer comprising an antigen peptide sequence, a β2-microglobulin sequence and a class I heavy chain sequence as set forth below.

SUMMARY

The present inventors have developed single chain trimer (SCT) molecules which are unbranched polypeptide chains comprising, in amino-to-carboxy terminal order, an antigen peptide sequence, a β2-microglobulin sequence, and a class I heavy chain sequence comprising sequences of extracellular, transmembrane, and intracellular domains of a class I heavy chain molecule. An SCT can further comprise a signal peptide sequence at the amino terminal, as well as first linker sequence extending between the peptide sequence and the β2-microglobulin sequence, and/or a second linker sequence extending between the β2-microglobulin sequence and the class I heavy chain sequence. In various aspects, the β2-microglobulin and the class I heavy chain sequences can be of human and/or murine origin.

In some aspects, an antigen peptide sequence can be that of a peptide which can be presented by an MHC class I molecule. In various configurations, an antigen peptide sequence can comprise from about 8 to about 15 contiguous amino acids. In some configurations, the antigen peptide sequence can comprise 9 contiguous amino acids. In various aspects, a peptide sequence can be that of a protein fragment, wherein the protein is a pathogen protein or a cellular protein, such as, for example, a protein expressed by a cancer cell, and wherein the peptide sequence can be bound by the MHC class I heavy chain sequence. In some configurations, the SCT can comprise any antigen peptide sequence that can bind the corresponding MHC class I heavy chain comprised by the SCT (discussed below). In some aspects, an antigen peptide sequence can be that of an HLA-A restricted peptide or HLA-B restricted peptide, such as an HLA-A*0201-restricted peptide. In some aspects, an antigen peptide can have a sequence as set forth in Table 1:

TABLE 1

Antigen Peptide Sequences*

| Name | Source | Sequence | Identification |
|------|--------|----------|----------------|
| CMVpp65 | Cytomegalovirus | NLVPMVATV | SEQ ID NO: 1 |
| EBV BMLF I | Ebstein-Barr virus | GLCTLVAML | SEQ ID NO: 2 |
| fluM1 | Influenza A virus | GILGFVFTL | SEQ ID NO: 3 |
| G209-2M | human melanoma | IMDQVPFSV | SEQ ID NO: 4 |
| G280-9V | human melanoma | YLEPGPVTV | SEQ ID NO: 5 |

*Sequences are presented using standard single-letter amino acid abbreviations as follows: A = alanine; C = cysteine; D = aspartic acid; E = glutamic acid; F = phenylalanine; G = glycine; H = histidine; I = isoleucine; K = lysine; L = leucine; M = methionine; N = asparagine; P = proline; Q = glutamine; R = arginine; S = serine; T = threonine; V = valine; W = tryptophan; Y = tyrosine.

In some aspects, a β2-microglobulin sequence comprised by an SCT can be a human β2-microglobulin sequence or a murine β2-microglobulin sequence. The β2-microglobulin sequence can a contiguous full-length β2-microglobulin sequence as expressed on the cell surface (i.e., without the leader peptide sequence). Accordingly, in some configurations, the β2-microglobulin sequence can comprise about 99 amino acids, and can be a human β2-microglobulin sequence as set forth in SEQ ID NO: 6.

In various aspects, an MHC class I heavy chain sequence comprised by an SCT can be a human MHC class I heavy chain sequence or a murine MHC class I heavy chain sequence. A human MHC class I heavy chain sequence can be any human class I heavy chain sequence, such as an HLA-A or an HLA-B class I heavy chain sequence. In some configurations, an HLA-A sequence can be an HLA-A*0201 sequence. In various aspects, an SCT can include all the domains of an MHC class I heavy chain, i.e., extracellular, transmembrane, and intracellular domains. In various aspects, the MHC class I heavy chain sequence can be the sequence set forth as SEQ ID NO: 7.

In some configurations, the MHC class I heavy chain sequence of an SCT can include single amino acid substitutions, additions, and/or deletions, such as a substitution of tyr-84 with a non-aromatic amino acid other than proline. In these configurations, the amino acid substitution can be an amino acid encoded by the standard genetic code such leucine, isoleucine, valine, serine, threonine, alanine, histidine, glutamine, asparagine, lysine, aspartic acid, glutamic acid, cysteine, arginine, serine or glycine, or can be a modified or unusual amino acid such as an amino acid recited in WIPO standard ST.25 (1998), Appendix 2, Table 4, which is incorporated by reference herein. In some aspects, the MHC class I heavy chain sequence can have the sequence set forth in SEQ ID NO: 8. In some aspects, tyr-84 can be substituted with an alanine, so that the MHC class I heavy chain sequence comprised by an SCT can have the sequence set forth as SEQ ID NO: 9.

In some aspects of the present teachings, the inventors disclose nucleic acid molecules comprising sequences encoding single chain trimers. In these aspects, a nucleic acid encoding a single chain trimer molecule can further comprise a sequence encoding a leader peptide sequence. In various aspects, the leader peptide sequence can be that of any secreted or cell surface protein that is expressed with a leader peptide sequence. In some embodiments, the leader peptide sequence can be that of secreted or cell surface polypeptide such as a human or murine β2-microglobulin, and can comprise about 20 amino acids. In some configurations, the leader peptide sequence can be that of the amino terminal sequence of a human β2-microglobulin or a murine β2-microglobulin, such as the 20 contiguous amino acid sequence from the amino terminal of murine β2-microglobulin, as set forth as SEQ ID NO: 10. Expression of a nucleic acid encoding an SCT including a leader peptide can, in some configurations, lead to expression of an SCT polypeptide which includes a complete leader peptide at the amino terminus, but in various configurations, an expressed SCT can omit the leader peptide sequence. Without being limited by theory, it is presumed that a cell expressing an SCT can proteolytically remove a leader peptide from an SCT post-translation.

In various aspects, an SCT can further comprise linker sequences, which can be sequences which impart flexibility between neighboring domains. In some aspects, a first linker sequence can extend between the antigen peptide sequence and the β2-microglobulin sequence. In some aspects, a first linker sequence can comprise at least about 10 amino acids up to about 15 amino acids, or up to about 20 amino acids. In other aspects, a second linker can extend between the β2-microglobulin sequence and the MHC class I heavy chain sequence, and can comprise, in some configurations, at least about 10 amino acids, or at least about 15 amino acids, up to about 20 amino acids. In various configurations, the first and second linkers can each contain at least about 80 percent glycine, alanine and/or serine residues, and in some aspects, about 80 percent glycine residues. In some configurations, the first linker can have a sequence (stated using standard single-letter amino acid abbreviations), of GGGGSGGGGS (SEQ ID NO: 11), GGGASGGGGSGGGGS (SEQ ID NO: 12), GGGGSGGGGSGGGGS (SEQ ID NO: 13), or GGGASGGGGS (SEQ ID NO: 27) and the second linker can have a sequence set forth as GGGGSGGGGSGGGGS (SEQ ID NO: 13) or GGGGSGGGGSGGGGSGGGGS (SEQ ID NO: 14).

Accordingly, a full-length single chain trimer molecule of the present teachings comprises, in amino-to-carboxy terminal order, a leader peptide sequence, an antigen peptide sequence, a first linker sequence, a β2-microglobulin sequence, a second linker sequence, and an MHC class I heavy chain sequence. In various configurations, the MHC class I heavy chain sequence can be that of any vertebrate, such as an HLA-A, -B or -C human class I heavy chain sequence, or, among murine sequences, a class I heavy chain sequence, an H-2-L class I heavy chain sequence such as an $1^b$ sequence, an H-2-K class I heavy chain sequence, an H-2-D heavy chain sequence such as an H-2-D$^d$ class I sequence or an H-2-L class I heavy chain sequence such as an H-2-L$^d$ sequence. In some aspects, the MHC heavy chain sequence can be a human HLA-A or an HLA-B sequence, and the SCT can have a sequence set forth as SEQ ID NO: 15, SEQ ID NO: 16, or SEQ ID NO: 17.

Other aspects of the present teachings include cells comprising a single chain trimer. Such cells can be antigen presenting cells, such as dendritic cells, B cells or macrophages. In various embodiments, the cells can be mammalian cells such as cells of human or rodent origin, including murine cells.

In some aspects, the present teachings encompass nucleic acids comprising sequences encoding the single chain trimers described herein. In certain embodiments of these aspects, a nucleic acid comprising a sequence encoding an SCT can further comprise a promoter operably linked to the SCT-encoding sequence. A nucleic acid of these aspects can also be comprised by a vector, such as a virus or a plasmid. In addition, in some aspects a nucleic acid can be comprised by a cell. A cell of these aspects can be a eukaryotic or prokaryotic cell, such as a vertebrate cell, an *E. coli*, or an insect cell. A vertebrate cell can be a mammalian cell, including a human cell or a rodent cell, such as a murine cell. A vertebrate cell can be, in various aspects, an antigen presenting cell such as a dendritic cell, a B cell or a macrophage.

The present inventors also disclose herein methods for expanding populations of antigen-specific CD8$^+$ T cells ex vivo using single chain trimers. The antigen-specific CD8$^+$ T cells to be expanded can be, in various aspects, autologous to a patient in need of adoptive T cell immunotherapy, or can be allogeneic to such a patient. In various configurations, methods of expanding a population of antigen-specific CD8$^+$ T cells ex vivo comprise first co-culturing, in a first culture, a population of antigen-specific CD8$^+$ T cells with a first population of antigen presenting cells comprising an MHC antigen peptide sequence. The initial co-culturing is then followed by co-culturing, in a second culture, the population of antigen-specific CD8$^+$ T cells with a population of cells comprising a single chain trimer (SCT) comprising the same MHC antigen peptide sequence as used in the first co-culture. These methods can be used to obtain about $1 \times 10^9$ antigen-specific CD8$^+$ T cells autologous to a patient in less than about two months after initiating the co-culturing of the antigen-specific CD8$^-$ T cells with the first population of antigen presenting cells, and, in some aspects, the methods can be used to obtain at least about $1 \times 10^9$ antigen-specific CD8$^+$ T cells autologous to a patient within about 28 days after initiating the co-culturing of the antigen-specific CD8$^+$ T cells with the first population of antigen presenting cells. In various configurations, expansion of a population of antigen-specific CD8$^+$ T cells can comprise an expansion of at least about 10,000 fold in less than about 2 months after initiating the co-culturing of the antigen-specific CD8$^+$ T cells with the first population of antigen presenting cells, or, in some configurations, at least about 100,000 fold within about 28 days after initiating the co-culturing of the antigen-specific CD8$^+$ T cells with the first population of antigen presenting cells. In various aspects, the population of antigen-specific CD8$^+$ T cells following the expanding can be at least about 55% pure, at least about 75% pure, or at least about 95% pure. In addition, following the expanding, the population of antigen-specific CD8$^+$ T cells can exhibit an increase of at least about $1.1 \times 10^5$ fold in Tetramer-positive cells (Altman, J. D. et al., Science 274: 94-96, 1996), or an increase of at least about $4.1 \times 10^6$ fold increase in Tetramer-positive cells. Furthermore, in some aspects, the population of antigen-specific CD8$^+$ T cells following the expanding can comprise at least one antigen selected from the group consisting of CD62L$^+$, CD27$^+$, CCR7$^+$ and CD28$^+$, and in some aspects, the population of antigen-specific CD8$^+$ T cells following the expanding can effect at least about 50% specific lysis at a 2:1 effector:target ratio.

In various aspects of these methods for expanding populations of antigen-specific CD8$^+$ T cells ex vivo, the antigen presenting cells of the first co-culture can be dendritic cells, B cells, macrophages or a combination thereof. In some configurations, these antigen presenting cells can be cells autologous to a patient in need of adoptive T cell immunotherapy. In some configurations, the culturing of the antigen-specific CD8$^+$ T cells with the antigen presenting cells comprising an MHC antigen peptide in the first culture can have a duration of about 7-21 days, such as about 14 days. In some aspects, the first culture can comprise a culture medium comprising interleukin-7 and/or interleukin-2. In various other aspects, in the second culture, the cells comprising a single chain trimer can include any cell type capable of harboring an SCT on the cell surface, such as a second population of antigen presenting cells. In various configurations, these cells can be cells expressing the SCT, and can be cells comprising a nucleic acid comprising a sequence encoding an SCT. These cells can be, in various aspects, hematopoietic cells including human hematopoietic cells, such as K562 human erythroleukemia cells. In some aspects, an SCT can be displayed by antigen presenting cells such as dendritic cells, B cells, macrophages or a combination thereof These cells can also be cells autologous to a patient in need of adoptive T cell immunotherapy. In some configurations, the culturing of the antigen-specific $CD8^+$ T cells with the cells comprising an SCT in the second culture can have a duration of about 7-21 days, such as about 14 days.

In various aspects, a single chain trimer comprised by a population of antigen presenting cells in the second culture medium can comprise a human $\beta_2$-microglobulin sequence, and can further comprise a human class I heavy chain sequence, such as an HLA-A or an HLA-B class I heavy chain sequence, including, in non-limiting example, the sequence of an HLA-A*0201 heavy chain. In addition, in some aspects, an antigen peptide portion of a single chain trimer can comprise at least about 8 contiguous amino acids up to about 13 contiguous amino acids, and, in some configurations, 9 contiguous amino acids, and can comprise a sequence of an MHC antigen. A sequence of an antigen peptide portion of a single chain trimer can be, in various configurations, identical to that of an MHC antigen comprised by a cell infected with a pathogen, such as a viral pathogen or a bacterial pathogen. In other configurations, a sequence of an antigen peptide portion of a single chain trimer can be, in various configurations, identical to that of an MHC antigen comprised by a cancer cell. Cancer cells comprising antigens for which single chain trimers can be produced include, without limitation, cells of a melanoma, a glioma, a lung carcinoma, a prostate carcinoma, a breast carcinoma, a colon carcinoma, a leukemia, a lymphoma, a myeloma, and a pancreatic carcinoma. An MHC antigen peptide portion comprised by a single chain trimer comprised by cells comprising the second culture medium the cells can be, in various configurations, identical to or have conservative substitutions in comparison to the MHC antigen peptide comprised by the antigen presenting cells comprised by the first culture. Sequences of antigen peptide portions of single cell trimers can be, for example, those set forth in Table 1, supra.

The present inventors also disclose herein methods for treating infection in a human subject. In various aspects, these methods comprise expanding a population of antigen-specific $CD8^-$ T cells autologous to a human subject in need of treatment of a pathogen infection in accordance with the methods disclosed herein, and administering the expanded population to the human subject.

The present inventors also disclose herein methods for treating cancer in a human subject. In various aspects, these methods comprise expanding a population of antigen-specific $CD8^-$ T cells autologous to a human subject in need of treatment of a cancer in accordance with the methods disclosed herein, and administering the expanded population to the human subject.

The present inventors also disclose herein nucleic acids which encode single chain trimers. A nucleic acid of these configurations can be, in various configurations, a vector comprising a promoter operably linked to a sequence encoding a single chain trimer, such as a plasmid or virus comprising a promoter operably linked to a sequence encoding an SCT.

The present inventors also disclose embodiments of the present teachings in which a vaccine comprises a single chain trimer, and/or a nucleic acid comprising a sequence encoding a single chain trimer. In various configurations, administration of an SCT to a mammal including a human can elicit a humoral antibody response and/or a cellular immunity response. The present inventors also contemplate a complex comprising a plurality of SCTs, such as for example a tetramer, a hexamer, or an octomer of an SCT. SCTs comprising such complexes can be attached covalently or non-covalently, such as through avidin-biotin or streptavidin-biotin complexes (see, e.g., Altman, J. D. et al., Science 274: 94-6, 1996) or with covalent cross-linkers such as, for example, those distributed by Pierce Chemical Co. (Rockford Ill.) or Sigma Chemical Co. (St. Louis Mo.). In some configurations, such complexes can be used in detection assays, such as, for example, flow cytometry analyses.

In various aspects, an SCT of the present teachings can also be used as probes to quantify the number of antigen/class I-specific complexes on the surface of cells such as tumor cells or pathogen-infected cells. Such complex-specific probes could be used to aid in the diagnosis of cancer or infection, or as laboratory research reagents.

In various aspects, an SCT of the present teachings can also be used as immunogen to raise antibodies peptides directed against MHC class I molecules comprising a bound peptide. The antibodies can be, in some configurations, monoclonal or polyclonal antibodies which recognize a complex comprising an MHC heavy chain and an antigen peptide. In some configurations, polyclonal antibodies raised against an SCT can be affinity purified using the SCT. Furthermore, in some configurations, an antibody reactive with MHC class I heavy chain but not specific for the peptide-heavy chain complex for a particular MHC peptide antigen can be removed by adsorption using methods well known in the art.

BRIEF DESCRIPTION OF THE FIGURES

FIG. 1 illustrates flow cytometric analysis of cell surface expression and T cell recognition of $L^d$-derived murine SCTs.

FIG. 2A illustrates flow cytometric analysis of LM1.8 cells expressing either OVA.$\beta 2m^b$.$K^d$ single chain trimer or a single chain dimer of $\beta 2m^b$.$K^d$, with or without OVA peptide. OVA peptide is derived from ovalbumin and has the sequence Ser-Ile-Ile-Asn-Phe-Glu-Lys-Leu (SIINFEKL) (SEQ ID NO: 18). FIG. 2B illustrates cytotoxic T cell recognition of OVA.$\beta 2m^b$.$K^d$ single chain trimer expressed by mouse L cells.

FIG. 4 flow cytometric analysis of cell surface expression and T cell recognition of varying OVA. $\beta$2-microglobulin.$K^b$ SCTs.

FIG. 5A illustrates immunoprecipitation of $K^b$, $\beta$2-microglobulin.$K^b$, and OVA.$\beta$2-microglobulin.$K^b$ SCT. FIG. 5B illustrates Endo-H sensitivity of these molecules.

FIG. 7 illustrates alignment of sequences of selected single chain trimers.

FIG. 8 illustrates a representative experiment in which CD8+ T cells from a normal volunteer were activated with autologous dendritic cells pulse with MHC antigen peptide P495 (SEQ ID NO: 1).

FIG. 9 illustrates ex vivo generation of large numbers of functional antigen-specific human CD8+ cells using K562 cells expressing a single chain trimer.

DETAILED DESCRIPTION

Figure 1A:
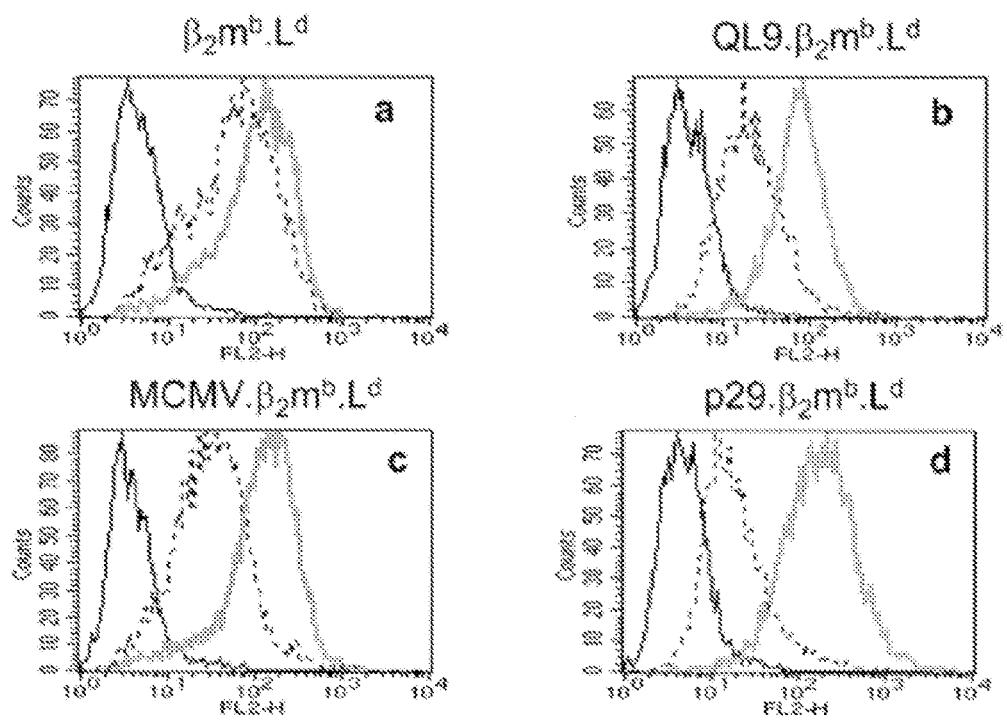
FIG. 1A illustrates flow cytometric analysis of DLD-1 cells expressing either QL9.$\beta 2m^b$.$L^d$ single chain trimer OVA.or a single chain dimer of $\beta 2m^b$.$L^d$.

The present inventors have developed single chain trimer ("SCT") molecules. In various configurations, an SCT molecule comprises, in amino-to-carboxy terminal order, an antigen peptide segment, a β2-microglobulin segment, and a class I heavy chain segment. In various configurations, an SCT molecule can further comprise a first linker segment extending between the peptide ligand segment and the β2-microglobulin segment, and/or a second linker segment extending between the β2-microglobulin and the class I heavy chain segment. In some configurations, an SCT molecule can further comprise a leader peptide. Disclosed herein are SCT's using both human and murine sequences, prepared using MHC antigen peptides from both human and murine pathogens or cells. Some non-limiting examples of SCTs and nucleic acid vectors comprising sequences encoding the SCTs are disclosed in table 2, and in the sequence listings which are incorporated herein by reference:

TABLE 2

| SCT name | Source | Identification | Identification of vector comprising DNA sequence encoding SCT |
| --- | --- | --- | --- |
| CMV SCT | Cytomegalovirus | SEQ ID NO: 21 | SEQ ID NO: 28 |
| EBV BMLF I SCT | Epstein-Barr virus | SEQ ID NO: 22 | SEQ ID NO: 29 |
| fluM1 SCT | Influenza A virus | SEQ ID NO: 23 | |
| G209-2M SCT | Human melanoma | SEQ ID NO: 24 | SEQ ID NO: 30 |
| G280-9V SCT | Human melanoma | SEQ ID NO: 25 | SEQ ID NO: 31 |
| SCT consensus | | SEQ ID NO: 26 | |

Adoptive T cell immunotherapy is a promising modality for the treatment of infectious diseases and cancer. However, the major limitation toward further progress is the difficulty obtaining large numbers of autologous antigen-specific T cells (either CD3+CD4+ [helper subset] or CD3+CD8+ [cytotoxic subset]) in a timely manner for therapeutic use. Implementation of this approach in clinical medicine will depend on manufacturing large numbers (>one billion) of antigen-specific T cells in a timeframe that is feasible and does not compromise the standards of patient care for any given disorder. The present disclosure describes a method using single chain trimer (SCT) to amplify, enrich and rapidly expand antigen peptide-specific CD8+ T cells in less than one month. This is accomplished using a two step culture process starting with purified CD8+ T cells co-cultured with autologous dendritic cells pulsed with the relevant peptide. The CD8+ T cell-DC cultures are maintained for no greater than 14 days and require addition of IL-7 (at time 0) and IL-2 (every 2-4 days). The responding T cells are then co-cultured with artificial APC (aAPC) expressing SCT for an additional 14 days in the presence of IL-2. Our experience to date shows that ~50 fold expansion of tetramer positive CD8+ T cells occurs during the initial culture period with peptide-pulsed DC. Amplification using aAPC with SCT results in significant expansion (2000-43,000 fold) with enrichment (55-95% positive by tetramer staining). After the start of the culture period, the percentage (0.07-4.5%, range) and number (18000-680,000 range) of antigen peptide-specific CD8+ T cells were low as expected in a group of healthy normal volunteers. After 28 days of culture, the CD8+ cells grown using SCT method as described exhibited features of enrichment (55-95% pure by tetramer staining), growth ($1.1 \times 10^5$-$4.1 \times 10^6$-fold tetramer positive cells), central memory phenotype (CD62L+CD27+CD28+), and potent function (50% specific lysis at 2:1 effector to target ratio). Advantages of this new method include: no need for single cell cloning or cell sorting/selection, brief culture period of less than one month, and reproducibility.

The present teachings describe the use of a two step culture process to obtain large numbers of antigen-specific CD8+ T cells. The entire culture period can be 28 days and can result in from about 10,000-fold to about 100,000-fold expansion of antigen-specific CD8+ T cells. The resultant T cells can show potent cytolytic activity and can contain central memory cells as well as effector memory T cells. Adoptive transfer of the resultant T cells to tumor-bearing animals can result in rapid tumor clearance as monitored by whole body bioluminescence imaging.

The methods and compositions described herein utilize laboratory techniques well known to skilled artisans and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999.

SCTs disclosed herein i) can undergo expeditious heavy chain folding and ER to Golgi transport, ii) can remain covalently attached, iii) can be at least 1000 fold less accessible to exogenous peptide than class I molecules loaded with endogenous peptides, and iv) can be potent stimulators of peptide-specific cytotoxic T lymphocytes ("CTL"). Furthermore, these SCTs reduce or circumvent immune evasion by viruses and tumors. Nucleic acids comprising sequences encoding SCT molecules have application as DNA vaccines against virus infection or tumors, as well as probes of molecular mechanisms of class I assembly. Accordingly, in various embodiments, the present teachings include a vaccine comprising a single chain trimer, a nucleic acid encoding a single chain trimer, or a combination thereof.

The amino acid sequences of class I heavy chains that comprise the class I heavy chain segment, as well as nucleic acids encoding these proteins, are well known in the art and are available from numerous sources including GenBank.

The present invention also provides sequence variants of the class I heavy chain. In some embodiments, the heavy chain can comprise a substitution for tyrosine at position 84 in the natural sequence. The substitution can be any amino acid other than proline or an aromatic amino acid.

Sequences of the present teachings, including variants thereof, can be prepared by methods well known to skilled artisans, such as organic synthetic methods, molecular cloning of a nucleic acid into a vector such as plasmid, bacteriophage or virus, polymerase chain reaction, and/or site-directed mutagenesis (e.g., Wallace et al., 1981, Nucleic Acids Res. 9, 3647-3656; Zoller and Smith, 1982, Nucleic Acids Res. 10, 6487-6500; and Deng and Nickoloff, 1992, Anal. Biochem. 200, 81-88). Some examples of sequences of primers which can be used in the construction of nucleic acids comprising sequences encoding SCTs are set forth in table 3:

TABLE 3

| Name of primer | Sequence | Identification |
|---|---|---|
| G280-9V F1 | CCGGCCGTAGACGGCATCGCAG CTTGGATACACGCCGCCCACGT GAAGGCTGCCGACCCCGGGGGT GGACCATCCTCTAGACTGCCAT GGCTCGCTCGGTGACCCTGG | SEQ ID NO: 32 |
| SCT R1 | CGCGCGGCGGCCGCTCACACTT TACAAGCTGTG | SEQ ID NO: 33 |
| CMV SCT-SDM-F | CTGACCGGTTTGTATGCTAACC TGGTGCCAATGGTGGCTACCGT GGGAGGAGGTGCTAGCGGTG | SEQ ID NO: 34 |
| CMV SCT-SDM-R | CACCGCTAGCACCTCCTCCCAC GGTAGCCACCATTGGCACCAGG GTAGCATACAAACCGGTCAG | SEQ ID NO: 35 |
| EBV SCT SDM-F | CTGACCGGTTTGTATGCTGGCC TGTGCACCCTGGTGGCCATGCT GGGAGGAGGTGCTAGCGGTG | SEQ ID NO: 36 |
| EBV SCT SDM-R | CACCGCTAGCACCTCCTCCCAG CATGGCCACCAGGGTGCACAGG CCAGCATACAAACCGGTCAG | SEQ ID NO: 37 |
| G209-2M SDM-F | CTGACCGGTTTGTATGCTATCA TGGACCAGGTGCCTTTCTCCGT GGGAGGAGGTGCTAGCGGTG | SEQ ID NO: 38 |

TABLE 3-continued

| Name of primer | Sequence | Identification |
|---|---|---|
| G209-2M SDG-R | ACCGCTAGCACCTCCTCCCACG GAGAAAGGCACCTGGTCCATGA TAGCATACAAACCGGTCAG | SEQ ID NO: 39 |

The peptide linkers which can comprise an SCT of the present teachings can predominantly comprise amino acids with small side chains, such as glycine, alanine and serine. In some aspects, at least about 80 percent of the linkers comprise glycine, alanine or serine residues, particularly glycine and serine residues. In various aspects, the linkers do not contain any proline residues. In various embodiments, linkers which can be used can comprise any of a number of flexible linker designs that have been used successfully to join antibody variable regions together (see M. Whitlow et al., Methods: A Companion to Methods in Enzymology, 2:97-105 (1991). Suitable linkers can be readily identified empirically. In non-limiting example, a DNA construct coding for an SCT which includes a linker can be cloned and expressed, and the SCT molecule can be tested to determine if it is capable of modulating the activity of a T cell receptor, either to induce T-cell proliferation or to inhibit or inactivate T cell development. Suitable size and sequences of linkers also can be determined by conventional computer modeling techniques based on the predicted size and shape of the SCT.

In various embodiments, an SCT can comprise a first flexible linker interposed between the peptide ligand segment and the β2-microglobulin segment. Such linkers can extend from and connect the carboxy terminal of the peptide ligand segment to the amino terminal of the β2-microglobulin segment. Without being limited by theory, it is believed that when an SCT is expressed, the linked peptide ligand can fold into the binding groove resulting in a functional SCT. In various embodiments, this linker can comprise at least about 10 amino acids, up to about 15 amino acids.

In various embodiments, an SCT can comprise a second flexible linker interposed between the β2-microglobulin segment and the heavy chain segment. Such linkers can extend from and connect the carboxy terminal of the β2-microglobulin segment to the amino terminal of the heavy chain segment. Without being limited by theory, it is believed that when an SCT is expressed, the β2-microglobulin and the heavy chain can fold into the binding groove resulting in a molecule which can function in promoting T cell expansion. In various embodiments, this linker can comprise at least about 15 amino acids, up to about 20 amino acids.

A polypeptide or peptide disclosed herein can be of a variety of lengths, either in a neutral (uncharged) form or in a salt form, and can include one or more modifications such as glycosylation, side chain oxidation, or phosphorylation, provided that the modification not destroy biological activity.

As used herein, the term "peptide" refers to a peptide, glycopeptide, glycolipid or any other compound associated with a ligand binding groove of various different molecules with an MHC class I or MHC class I-like structure (Fundamental Immunology, 2d Ed., W. E. Paul, ed., Ravens Press N.Y. 1989). Antigen peptides from a number of sources have been characterized in detail, including, in some non-limiting examples, antigen peptides from honey bee venom allergens, dust mite allergens, toxins produced by bacteria (such as tetanus toxin) and human tissue antigens involved in autoimmune diseases. Detailed discussions of such peptides are presented in U.S. Pat. Nos. 5,595,881, 5,468,481 and 5,284, 935. Other non-limiting examples of antigen peptides include those identified in the pathogenesis of rheumatoid arthritis (type II collagen), myasthenia gravis (acetyl choline receptor), and multiple sclerosis (myelin basic protein). As an additional example, suitable peptides which induce Class I MHC-restricted CTL responses against HBV antigen are disclosed in U.S. Pat. No. 6,322,789.

As used herein, the term antigen peptide encompasses peptides derived from both non-self and self sources which can associate with the binding groove of an MHC molecule.

In various configurations, an antigen peptide sequence comprised by an SCT can comprise from about 8 contiguous amino acid residues to about 15 contiguous amino acid residues, and in some configurations, 9 contiguous amino acid residues.

In general, preparation of an SCT can be accomplished by procedures disclosed herein and by recognized recombinant DNA techniques, e.g., preparation of plasmid DNA, cleavage of DNA with restriction enzymes, ligation of DNA, transformation or transfection of a host, culturing of the host, and isolation and purification of the expressed fusion complex. Such procedures are generally known and disclosed in standard references such as in Sambrook et al., supra.

In some aspects, DNA encoding a class I heavy chain can be obtained from a suitable cell line such as, for example, human lymphoblastoid cells. In various configurations, a gene or cDNA encoding a class I heavy chain can be amplified by the polymerase chain reaction (PCR) or other means known in the art. In some aspects, a PCR product can also include sequences encoding linkers, and/or one or more restriction enzyme sites for ligation of such sequences.

In some configurations, a vector encoding an SCT can be prepared by ligation of sequences encoding the MHC heavy chain and the $\beta$2-microglobulin to a sequence encoding an antigen peptide. DNA encoding the antigen peptide can be obtained by isolating DNA from natural sources or by known synthetic methods, e.g., the phosphate triester method. See, e.g., Oligonucleotide Synthesis, IRL Press (M. Gait, ed., 1984). Synthetic oligonucleotides can also be prepared using commercially available automated oligonucleotide synthesizers. A DNA sequence encoding a linker as discussed supra can be interposed between a sequence encoding a $\beta$2-microglobulin segment and a sequence encoding an antigen peptide segment, and can be interposed between a $\beta$2-microglobulin segment and the heavy chain segment. In some configurations, the segments can be joined using a ligase.

Other nucleotide sequences also can be included in the gene construct. For example, a promoter sequence, which controls expression of the sequence coding for the $\beta$2-microglobulin segment covalently bound to the peptide ligand segment, and a sequence encoding a leader peptide (which can direct an SCT to the cell surface or the culture medium), can be included in the construct or present in the expression vector into which the construct is inserted. In non-limiting example, an immunoglobulin or CMV promoter can be used for expression of an SCT. A strong translation initiation sequence also can be included in the construct to enhance efficiency of translational initiation, such as, for example, the Kozak consensus sequence (CCACCATG), or an internal ribosome entry site (IRES). In some configurations, a nucleic acid encoding an SCT can further encode an amino terminal leader peptide. When expressed in a host cell, the primary translation product of such a nucleic acid can comprise a leader peptide which can be removed by the host cell post-translationally.

In some configurations, a leader sequence encoded by a DNA construct can contain one or more restriction sites so that an oligonucleotide encoding an antigen peptide segment of interest can be attached to the first linker. In some aspects, a restriction site can be incorporated into the 3' end of the DNA sequence encoding a leader peptide sequence, and can be, for example, about 2 to 10 codons in length, and can be positioned before the coding region for the peptide ligand. A non-limiting example of a restriction site is the AflII site, although other cleavage sites also can be incorporated before the peptide ligand coding region. As discussed supra, use of such a restriction site in combination with a second restriction site, typically positioned at the beginning of the sequence coding for the linker, can allow rapid and straightforward insertion of sequences coding for a wide variety of peptide ligands into a DNA construct encoding an SCT.

A number of strategies can be employed to express an SCT. For example, the SCT can be incorporated into a suitable vector by known methods such as by use of restriction enzymes and ligases (see, e.g., Sambrook et al., supra). A vector can be selected based on factors relating to the cloning protocol. For example, the vector should be compatible with, and have the proper replicon for the host that is being employed. Suitable host cells include eukaryotic and prokaryotic cells, and can be cells that can be easily transformed and exhibit rapid growth in culture medium. Examples of hosts cells include prokaryotes such as *E. coli* and *Bacillus subtilis*, and eukaryotes such as animal cells and yeasts, such as, for example, *S. cerevisiae*. Non-limiting examples of mammalian cells which can be used as hosts to express an SCT include J558, NSO, SP2-O and CHO. Other examples of possible hosts include insect cells such as Sf9, which can be grown using conventional culturing conditions. See Sambrook, et al., supra. In various configurations, cells expressing an SCT can be identified using known methods. For example, expression of an SCT can be determined by an ELISA or Western blot using an antibody probe directed against the MHC heavy chain portion of the SCT.

An expressed SCT can be isolated and purified by known methods. For example, an SCT containing a human HLA-DR1 sequence can be purified by affinity chromatography on a monoclonal antibody L243-SEPHAROSE column by procedures that are generally known and disclosed, e.g., see Harlow, E. et al., Antibodies, A. Laboratory Manual (1988). The L243 monoclonal antibody is specific to a conformational epitope of the properly folded HLA-DR1 molecule (J. Gorga et al. J. Biol. Chem., 262: 16087-16094), and therefore can be used for purifying a biologically active SCT. In some configurations, an SCT also can also contain a sequence to aid in purification; e.g., a 6×His tag.

In some embodiments, an SCT can be useful in mediating cell immunity as evidenced by an ability to expand a population of cytotoxic T lymphocytes specific for a class I/peptide complex. Furthermore, plasmid DNA that encodes an SCT can be used to produce an SCT which can be used an immunogen for producing an antibody. Such antibody can be, for example, a monoclonal antibody which can recognize and bind a complex comprising an MHC antigen peptide and an MHC class I molecule. A monoclonal antibody can be produced using methods well known to skilled artisans. In some configurations, a monoclonal antibody can be tagged with any tag known to skilled artisans, such as, for example, a fluorophore. An antibody of these configurations can be used in research and/or diagnostically, for example as part of a flow cytometry analysis of a sample from a human patient.

In other embodiments, an SCT or a composition containing an antigen peptide bound to an SCT can be used as immunogen for the preparation of antibodies directed against the antigen or the SCT. A polyclonal or monoclonal antibody against an SCT can be prepared by any of a variety of methods known to skilled artisans (see, e.g., Kohler et al., Nature 256:495 (1975); Kohler et al., Eur. J. Immunol. 6:511 (1976); Kohler et al., Eur. J. Immunol. 6:292 (1976); Hammerling et al., In: Monoclonal Antibodies and T-Cell Hybridomas, Elsevier, N.Y., pp. 563-681 (1981), and U.S. Pat. No. 2,658, 197). In some configurations, an antibody can be labeled. Examples of labels that can be employed include, but are not limited to, enzymes, radioisotopes, fluorophores, chromophores, chemiluminescent compounds, bioluminescent compounds, and metal chelates.

Examples of enzymes include malate dehydrogenase, staphylococcal nuclease, delta-V-steroid isomerase, yeast alcohol dehydrogenase, alpha-glycerophosphate dehydrogenase, triose phosphate isomerase, biotin-avidin peroxidase, horseradish peroxidase, alkaline phosphatase, asparaginase, glucose oxidase, β.-galactosidase, ribonuclease, urease, catalase, glucose-VI-phosphate dehydrogenase, glucoamylase and acetylcholine esterase.

Examples of isotopes are $^3H$, $^{125}I$, $^{32}P$, $^{35}S$, $^{14}C$, $^{51}Cr$, $^{36}Cl$, $^{57}Co$, $^{58}Co$, $^{59}Fe$, and $^{75}Se$. Among the most commonly used fluorescent labeling compounds are fluoroscein, isothiocyanate, rhodamine, phycoerythrin, phycocyanin, allophycocyanin, o-phthaldehyde, and fluorescamine Examples of typical chemiluminescent labeling compounds are luminal, isoluminol, theromatic acridinium ester, imidazole, acridinium salts, oxalate ester, and dioxetane.

Those of ordinary skill in the art will know of other suitable labels for binding to antibodies, or will be able to ascertain the same by the use of routine experimentation. Furthermore, the binding of these labels to antibodies can be accomplished using standard techniques commonly known to those of ordinary skill in the art. Bioluminescent compounds for purposes of labeling include luciferin, luciferase and aequorin.

In some aspects, antibodies and antigens of the present teachings can be comprised by a kit. A kit can comprise, in various embodiments, a carrier such as a carrier compartmentalized to receive one or more containers, such as vials or tubes.

In various embodiments, an SCT, a composition containing antigen bound to an SCT, and antibodies to these substances can be used in diagnostic applications. For example, an SCT can be used to target lymphocyte receptors, such as $CD4^+$ and $CD8^+$ receptors of T lymphocytes, and the resulting bound determinant can be assayed, for example, by use of an antibody to the bound determinant. In addition, it will be understood that an SCT can be labeled in a manner previously described for antibodies. In this case, the label on the molecule can be detected and quantified. Compositions comprising an antigen bound to an SCT can be used in a similar manner with MHC-restricted receptors recognizing the antigen and a determinant. Typical examples of assays based on the antibodies of the invention are radioimmunoassays (RIA), enzyme immunoassays (ETA), enzyme-linked immunosorbent assays (ELISA), and immunometric or sandwich immunoassays, including simultaneous sandwich, forward sandwich, and reverse sandwich immunoassays.

In another embodiment, an SCT, a composition containing an antigen bound to an SCT, and antibodies to these substances can be administered to a mammal to produce a therapeutic effect. For example, an immune response to self components can cause an autoimmune disease. In some configurations, an SCT, or an antibody against an antigen peptide-MHC complex which is generated against an SCT as immunogen, can be used administered therapeutically to a patient in need thereof. Thus, for example, an SCT can be utilized to treat T cell mediated autoimmune diseases, such as thyroiditis or multiple sclerosis. Other therapeutic uses include therapeutics for bacterial and viral infections, as well as for cancer treatments. In various aspects, these SCTs can be soluble SCTs.

This present teachings also provide an SCT for use in therapeutic or vaccine compositions. Conventional modes of administration can be employed. For example, administration can be carried out by oral, respiratory, or parenteral routes. Intradermal, subcutaneous, and intramuscular routes of administration are preferred when the vaccine is administered parenterally. A therapeutic or vaccine formulation can be prepared by mixing a single chain trimer with an excipient, and dosages and administration routes can be determined according to methods well-known in the art, for example, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003.

In some configurations, the ability of an SCT to exhibit a therapeutic or immunizing effect can be enhanced by emulsification with an adjuvant, incorporation in a liposome, coupling to a suitable carrier or even in cells or by combinations of these techniques. For example, the molecules and compositions can be administered with a conventional adjuvant, such as aluminum phosphate and aluminum hydroxide gel, in an amount sufficient to mediate humoral or cellular immune response in the host. Other suitable water soluble adjuvants, such as the Ribi adjuvant system available from Corixa, Seattle, Wash.

In addition, any of the common liquid or solid vehicles can be employed, which are acceptable to the host and do not have any adverse side effects on the host nor any detrimental effects on the reagents of the invention. Conveniently, phosphate buffered saline at a physiological PH can be employed as the carrier. One or more injections may be required, particularly one or two additional booster injections. It will be understood that conventional adjuvants, such as SAF-1, complete Freund's adjuvant and incomplete Freund's adjuvant, or oil-based adjuvants, such as mineral oil, can be administered with an SCT to elicit or enhance an antibody or cell-mediated immune response.

In some aspects, a humanized antibody against an SCT can be prepared using procedures well known in the art (using either chimeric antibody production or CDR grafting technology). U.S. Pat. No. 4,816,567 Cabilly et al., EPA 0120694 Publication No., assigned to Celltech, EPA 0173494 Publication No. assigned to Stanford University, and EPA 0125023 Publication No. assigned to Genentech, describing chimeric antibody procedures and EPA 0194276 Publication No. assigned to Celltech describing CDR grafting procedures.

A humanized antibody can be used therapeutically in humans so as to avoid the problems associated with the use of non-human antibodies in human therapy.

EXAMPLES

The following examples are illustrative, and are not intended to limit the scope of the claims. The description of a composition or a method in an example does not imply that a described composition or article has, or has not, been produced, or that a described method has been performed, irrespective of verb tense used.

Example 1

Figure 8A:
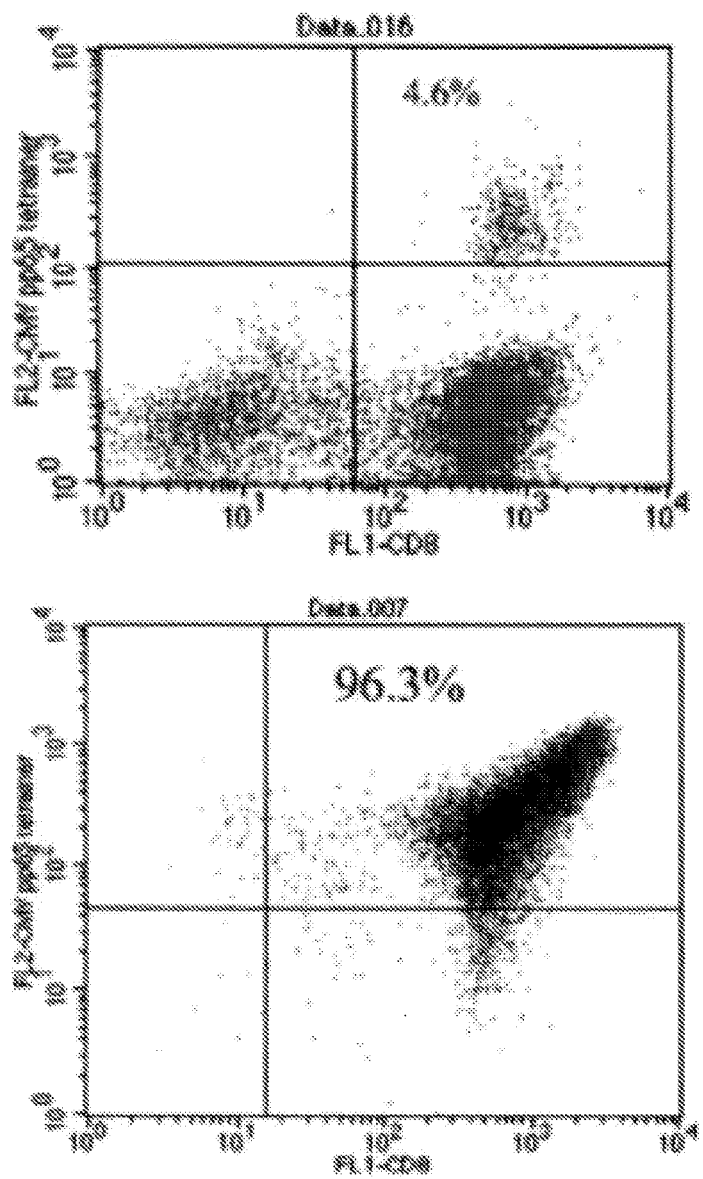
FIG. 8A illustrates flow cytometric analysis of CD8+ T cells showing increasing percentages of T cells specific for P495 as determined by tetramer staining (Altman, J. D. et al., Science 274: 94-96, 1996): 4.6% at start of culture; 61.1% positive at day 14 of culture, and 96.3% at day 28 of culture.
Figure 8A:
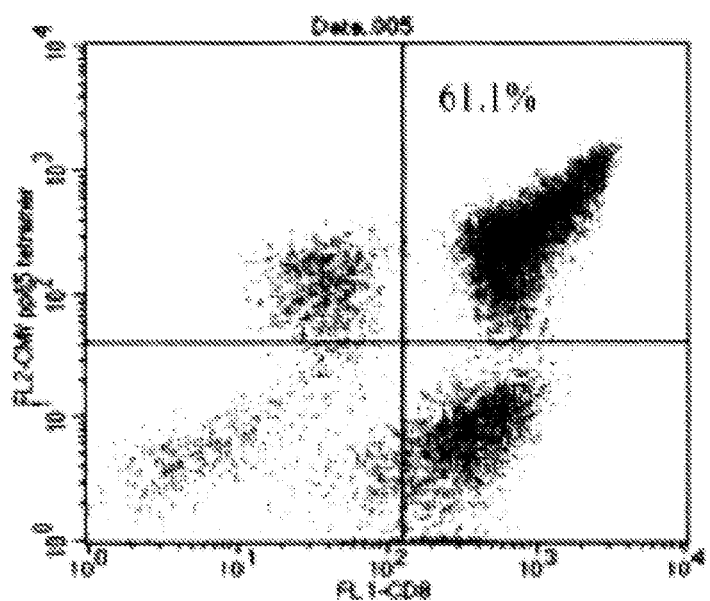
Figure 8B:
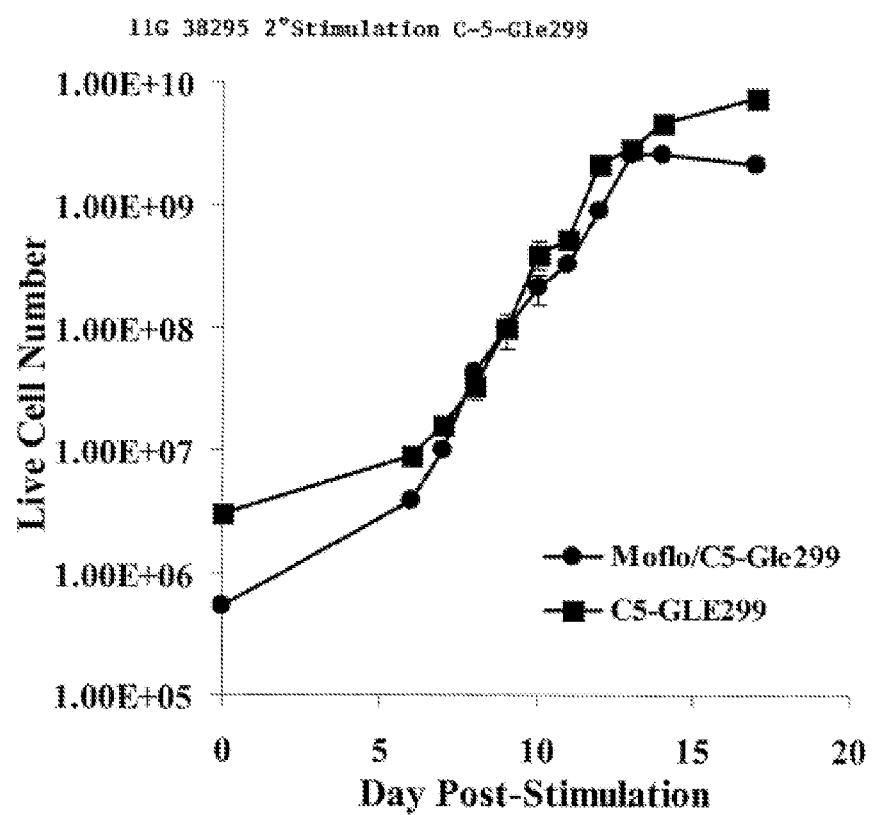
FIG. 8B illustrates a growth curve during secondary stimulation, in which diamonds represent CD8+ cells purified on a cell sorter, compared to unpurified CD8+ cells (squares).

This example, as illustrated in FIG. 8, provides a representative experiment in which CD8+ T cells from healthy human volunteer (11G38295) were activated with autologous dendritic cells pulsed with P495 peptide (SEQ ID NO: 1) and cultured for 14 days. At the start of culture, 4.6% CD8+ T cells were specific for P495 peptide antigen as assessed by tetramer statining. At day 14, the percentage increased to 61.1%. The CD8+ T cells were then washed and placed in culture with SCT transfectants (called C5-Gle299 cells) in the presence of interleukin-2 (IL-2). Fourteen days later (day 28 of culture), 96.3% of the cells were specific for P495 as assessed by tetramer analysis. The growth curve (11G38295 secondary stimulation) for this experiment is shown: CD8: T cells purified on a cell sorter (MoFlo, diamonds) compared to unpurified CD8+ cells (squares).

Example 2

Figure 9A:
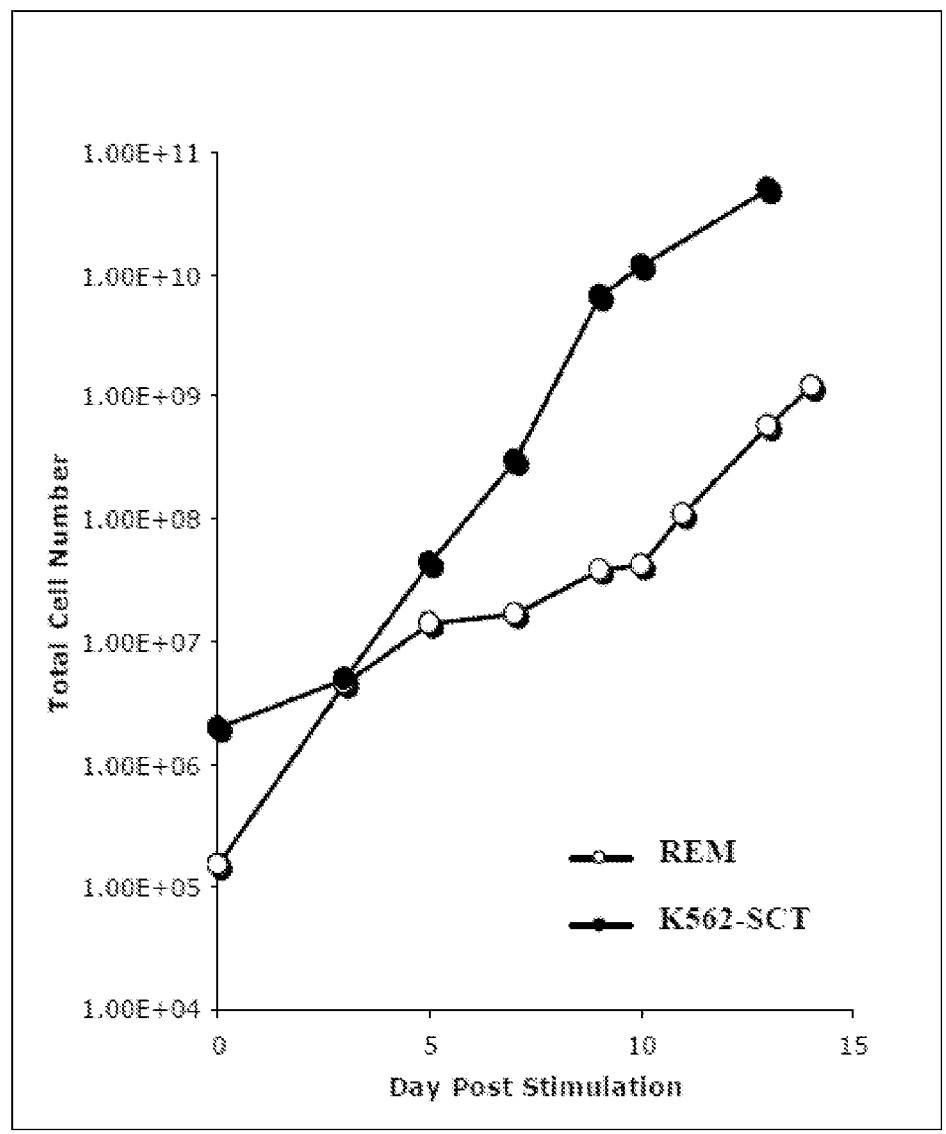
FIG. 9A illustrates CD8+ T cell growth over a 28 day period, comparing stimulation using the present methods including dendritic cells expressing a single chain trimer comprising NLVPMVATV (SEQ ID NO: 1) antigen peptide sequence (closed circles) vs. stimulation using a rapid expansion method (REM) protocol (open circles).
Figure 9B:
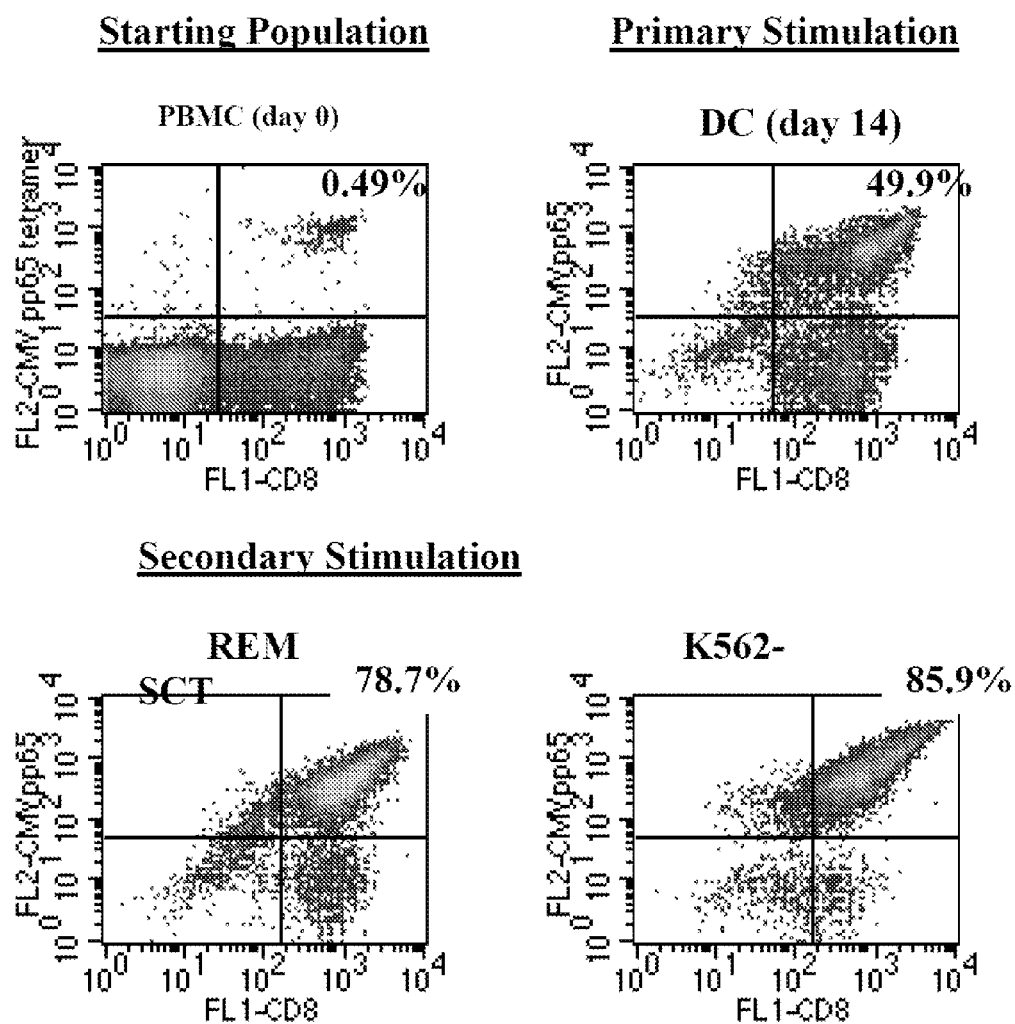
FIG. 9B illustrates flow cytometry analysis of CD8+ cells during the culture period.

This example, as illustrated in FIG. 9, demonstrates that large numbers of functional antigen-specific human CD8+ T cells can be generated ex vivo using K562 cells expressing single chain HLA-A2/CMV peptide/B-microglobulin trimer (K562-SCT). Fresh peripheral blood CD8+ T cells were first stimulated with autologous DC and pp65 peptide (NLVPMVATV (SEQ ID NO: 1)) for 14 days (primary stimulation), harvested and stained using HLA-A2/CMV pp65 tetramer. (A) For the secondary restimulation, CD8+ cells were purified by high speed sorting based on tetramer staining and restimulated for 14 days using the REM method (open circles) or alternatively, unsorted CD8+ T cells were re-stimulated for 14 days in the presence of K562-SCT (closed circles). A representative experiment shows CD8+ T cell growth (total cell number, mean of triplicate determinations) in a secondary 14 days culture period for each group; (B) Flow cytometry analysis of CD8+ T cells during the culture period. Percentages of HLA-A2-CMV pp65 peptide tetramer positive (tet+) CD8+ T cells at initiation of the culture (day 0, 0.49%) after DC stimulation (day 14, 49.9%) and after REM (day 28, 78.7%) or K562-SCT (day 28, 85.9%) expansion. The entire culture period is 28 days.

The results demonstrate a rapid (28 day) and efficient 2-step stimulation method for the expansion of antigen-specific (tet+) CD8+ T cells. These methods do not require the isolation of antigen-specific cells prior to expansion, and can achieve at least about $10^4$-fold increase in antigen-specific CD8+ T cells (see Table 4).

Example 3

Figure 10:
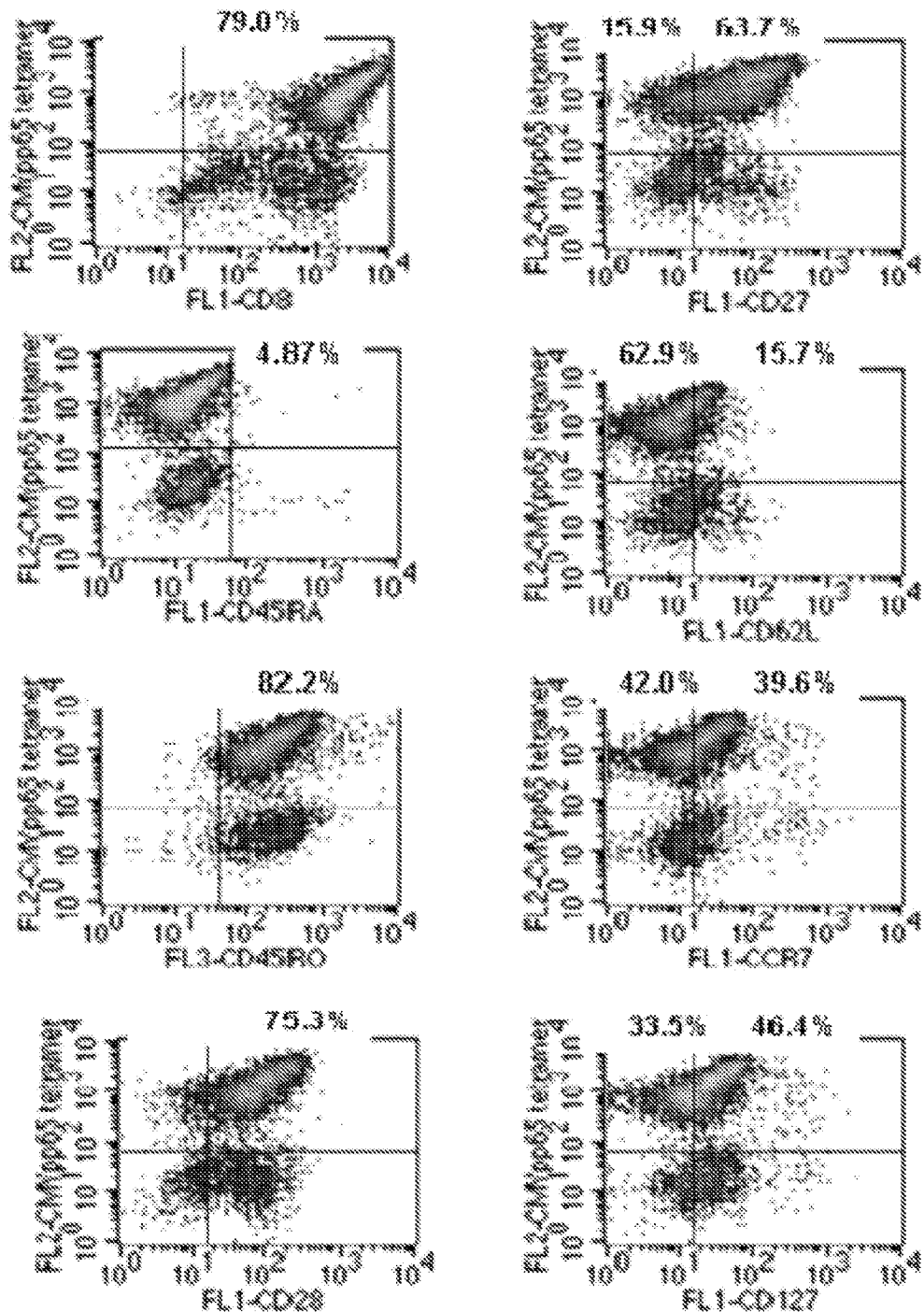
FIG. 10 illustrates retention of CD28 expression and display of a phenotype consistent with central memory, effector memory and effector T cell subsets in CD8+ T cells expanded with K562-SCT.

This example, as illustrated in FIG. 10, demonstrates retention of CD28 expression and display of a phenotype consistent with central memory, effector memory and effector T cell subsets in CD8+ T cells expanded with K562-SCT. K562-SCT expanded CD8+ T cells retain CD28 expression and display a phenotype consistent with central memory, effector memory and effector T cell subsets. CD8+ T cells were expanded using DC and peptide in primary stimulation for 14 days followed by K5652-SCT in secondary stimulation. On day 18 after the secondary stimulation, cells were harvested and stained using PE-conjugated HLA-A2/CMV-pp65 tetramers (tet-) and FITC-conjugated anti-CD8, -CD45RA, -CD45RO, -CD-28, -CD27, -CD62L, -CCR7 and -CD127 (IL-7Rα).

Adoptive transfer of tumor-specific CD8+ T cells in tumor-bearing mice has shown that terminally differentiated effector T cells are less potent at curing animals with advanced tumors (Gattinoni et al (2005) J. Clin. Invest. 115: 1616). Other published methods on ex vivo expansion of T cells require multiple rounds of in vivo stimulation resulting in terminally differentiated effector T cells (ref). We show that K562-SCT expanded CD8+/tet+ T cells express CD45RO (memory t cells) and retained CD28 expression. A significant percentage of tetramer+ T cells retain expression of CD 27, CD62L, CCR7 and CD127. These results demonstrate that a 2-step method of T cell stimulation using K562-SCT allows for the expansion of multiple T cell subsets including central memory (CD45RO/CCR7+/CD127+), effector memory (CD45RO/CCR7-/CD127+) and effector (CD45RO/CCR7-/CD127-) T cells.

Example 4

Figure 11:
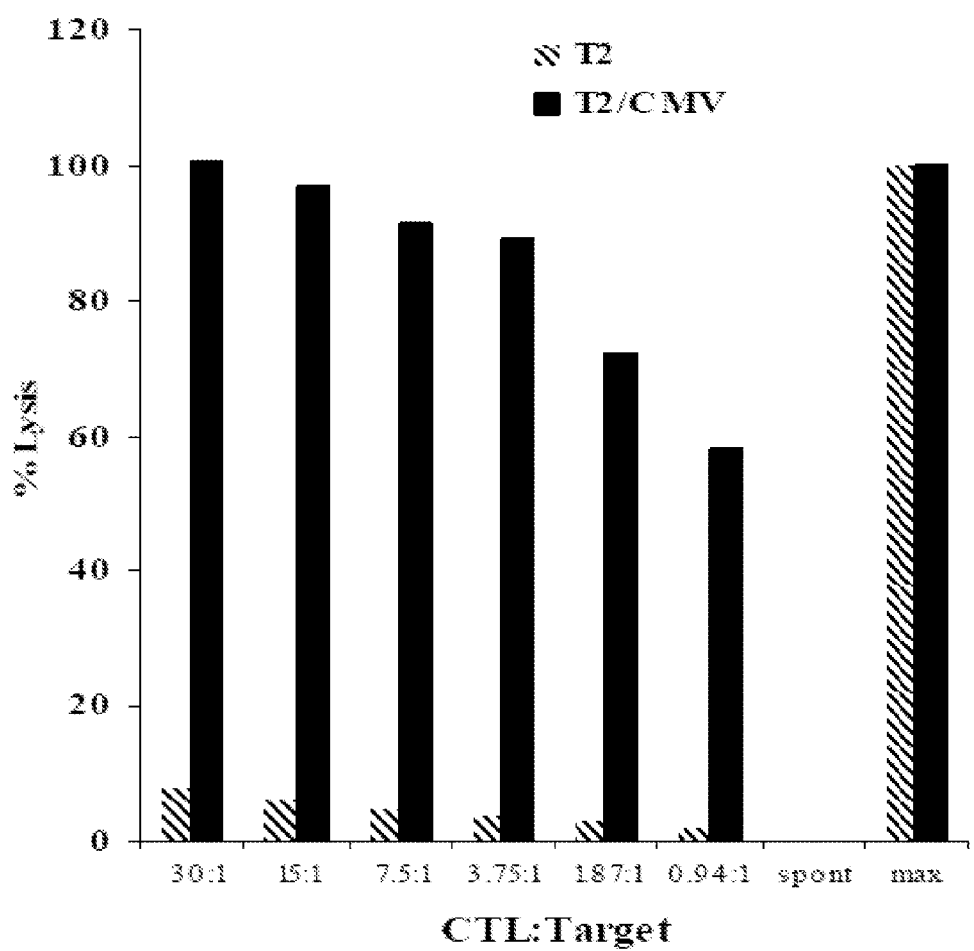
FIG. 11 illustrates lytic activity of CD8+ T cells expanded with K562-SCT.

This example, as illustrated in FIG. 11, demonstrates the K562-SCT expanded CD8+ T cells show potent lytic activity. In these experiments, CD8+ T cells were expanded using K562-SCT cells as described in Example 3. K562-SCT expanded CD8+ T cells show potent lytic activity. CD8+ T cells were expanded using K562-SCT cells. T cells were tested for their ability to kill CMV pp65 peptide-pulsed (solid bars) T2 target cells in a standard 4 hr $^{51}$Cr release assay. Target cells with no peptide (dashed bars) are shown as the control. Data is presented as the mean percent specific lysis of triplicate samples. Results have been repeated in 3 donors.

Example 5

Figure 12B:
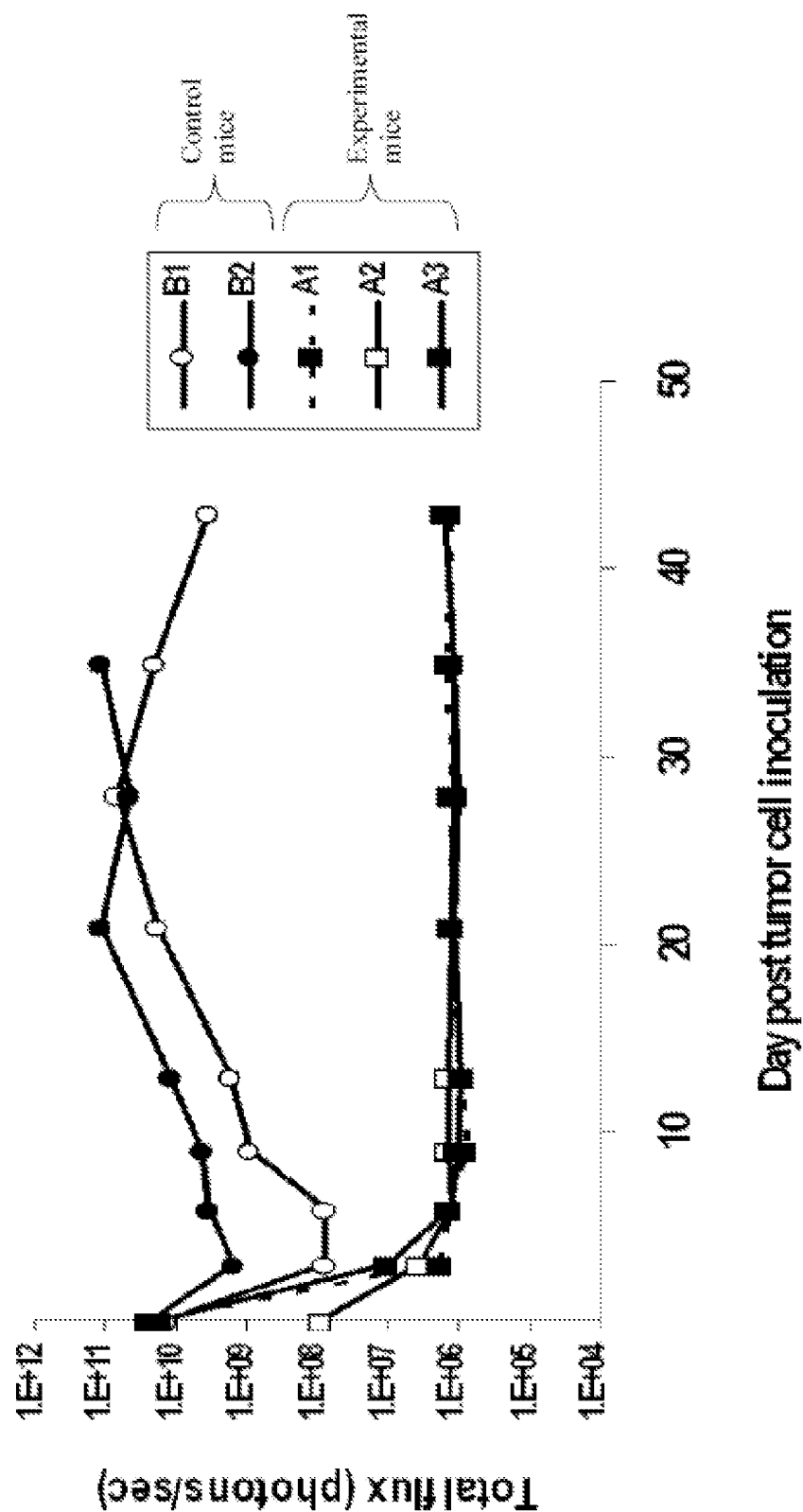
FIG. 12 illustrates that adoptive transfer of K562-SCT expanded CMV-specific human CD8+ T cells can result in tumor regression. Bioluminescence images are shown in FIG. 12A, and light emission quantification is shown in FIG. 12B.

This example, as illustrated in FIG. 12, demonstrates tumor regression following adoptive transfer of K562-SCT expanded CD98+ cytomegalovirus-specific human CD8+ T cells. Adoptive transfer of K562-SCT expanded CMV-specific human CD8+ T cell results in tumor regression. CD8+ T cells were expanded using K562-SCT as described in FIG. 10. On day 0, NOD/Scid β2m (NSB) null mice were injected intra-peritoneal (i.p.) with CMV pp65-expressing tumor cells ($5\times10^6$ cells) and CD8+ expanded T cells ($5\times10^7$ cells/dose). Mice received 2 additional injections of T cells ($5\times10^7$ cells/dose) on days 3 and 6. At the indicated times, mice were injected with an aqueous solution of luciferin (150 mg/kg, i.p.) 5 minutes prior to imaging. Animals were placed in chamber with a CCD camera system (IVIS, Xenogen) and tumor growth was quantitated by measuring light emission (bioluminesence). Mice A1-3 received tumor and CMV-specific T cells, mice B1-2 received tumor but no T cells. Bioluminescence images are shown in (A) and light emission quantification is shown in (B).

Inhibition of tumor growth is observed in mice treated with K562-SCT expanded CD8+ CMV-specific T cells. These results indicate that K562-SCT expanded CD8+ T cells effectively recognize tumor cells expressing CMV antigen in vivo resulting in tumor growth inhibition. On autopsy, no visible tumor was found in any animal given T cells while large tumor deposits were found in both control mice.

Example 6

This example, as illustrated in Tables 3a and 3b, provides an example of the number of T cells at initiation of culture (day 0):

TABLE 3a

Primary stimulation - Dendritic cells + peptide

| Donor ID | | Initial # | Final # |
|---|---|---|---|
| 1A | Total T cells (% tet+) | $1.4 \times 10\ 7$ (.49%) | $7.4 \times 10\ 6$ (49.9%) |
|  | tet+ T cells | $6.9 \times 10.4$ | $3.7 \times 10\ 6$ |
| 1B | Total T cells (% tet+) | $6 \times 10\ 6$ (1.5%) | $1.6 \times 10\ 7$ (34%) |
|  | tet+ T cells | $9 \times 10\ 4$ | $5.4 \times 10\ 6$ |
| 2 | Total T cells (% tet+) | $2.67 \times 10\ 7$ (0.07%) | $2.2 \times 10\ 8$ (20.1%) |
|  | tet+ T cells | $1.86 \times 10\ 4$ | $4.42 \times 10\ 7$ |

TABLE 3b

Secondary stimulation - REM vs K562-SCT

| 1A | REM | | $1.5 \times 10\ 5$ | $1 \times 10\ 9$ |
|---|---|---|---|---|
|  | K562-CMV SCT pp65 | Total T cells (% tet+) | $2 \times 10\ 6$ (49.9%) | $5 \times 10\ 10$ (85.9%) |
|  |  | tet+ T cells | $9.9 \times 10\ 5$ | $4.2 \times 10\ 10$ |
| 1B | REM | | $1.5 \times 10\ 5$ | $6 \times 10\ 9$ |
|  | K562-CMV SCT pp65 | Total T cells (% tet+) | $2 \times 10\ 6$ (34%) | $2.8 \times 10\ 9$ (55%) |
|  |  | tet+ T cells | $6.8 \times 10\ 5$ | $1.5 \times 10\ 9$ |
| 2 | REM | | $1.5 \times 10\ 5$ | $8.6 \times 10\ 9$ |
|  | K562-CMV SCT pp65 | Total T cells (% tet+) | $2 \times 10\ 6$ (20.3%) | $3.5 \times 10.9$ (70.4%) |
|  |  | tet+ T cells | $4 \times 10\ 5$ | $2.5 \times 10\ 9$ |

Shown is the number of T cells at initiation of culture (day 0) and at the end of the primary culture (day 14) and the secondary culture (day 28). ID 1A and 1B represent the same donor in 2 separate experiments. In the parenthesis are the percentages of antigen-specific CD8+ T cells as determined by staining with PE-HLA-A2/CMV pp65 tetramer and anti-CD8 Abs and analyzed by FACS. Absolute CD8+/Tet+ T cell numbers are calculated based on percentages obtained by FACS analysis. Cell sorting was performed on day 14 for REM stimulated cultures only.

Example 7

This example, as illustrated in Table 4, presents a comparison of T cell expansion using rapid expansion methods (REM) vs. K562-SCT mediated expansion methods.

TABLE 4

| Stimuli | Expt. | tet+ Fold Increased | % tet + cells |
|---|---|---|---|
| DC + REM | 1 | $2.8 \times 10\ 5$ | 78.7 |
|  | 2 | $1.7 \times 10\ 6$ | 70 |
|  | 3 | $9.7 \times 10\ 7$ | 73 |
| DC + K562 SCT | 1 | $2.3 \times 10\ 6$ | 85.9 |
|  | 2 | $1.3 \times 10\ 5$ | 55 |
|  | 3 | $1.4 \times 10\ 7$ | 70.4 |

Shown are CD8+/tet+ T cell fold-expansion obtained at 28 days in 3 independent experiments. Antigen-specific T cells fold increases are calculated based on percentages of tet+ cells as described in Table 3. Cell sorting was performed on day 14 for REM stimulated cultures only. No cell sorting is needed for K562-SCT stimulated cultures.

Example 8

This example sets forth many materials and methods used in experiments presented herein. In these experiments, single chain trimers, in which all three components of the completely assembled class I molecules are covalently attached to each other via flexible peptide linkers, were produced. Each of the SCTs consisted of the following elements beginning with the amino terminus: a leader sequence of β2-microglobulin, an antigen peptide sequence, a first flexible linker of 10 or 15 amino acid residues, the mature portion of murine or human β2-microglobulin, a second flexible linker of 15 or 20 amino acid residues, and a mature portion of an MHC class I heavy chain, including extracellular, transmembrane, and intracellular domains.

To serve as controls, constructs were also made with only β2-microglobulin covalently attached to a heavy chain. The control constructs consisted of the entire coding region of β2-microglobulin linked via a 15 or 20 amino acid residue linker to the mature portion of the respective heavy chain.

These constructs were stably introduced into mouse or human cell lines and cloned by limiting dilution. Structural integrity of these constructs was then examined by serological as well as functional assays.

Mice

B6 (H-$2^b$), BALB/c (H-$2^d$) and (C3H×B6)F1 (H-$2^{k \times b}$) were purchased from Charles River Laboratory (Wilmington, Mass.) and housed in the barrier animal facility at Washington University School of Medicine (St. Louis, Mo.). OT-1 transgenic mice (Hogquist et al., 1994) were obtained from R. Lorenz, the Washington University School of Medicine.

Cell Lines, Antibodies and Peptides

Cell lines used in this study were RMA, LM1.8, DLD-1, and B6/WT-3. RMA is a Rauscher leukemia virus-induced cell line of C57BL/6 (H-$2^b$) origin. LM1.8 was obtained from INSERM, Institut Pasteur, France and was derived by introducing the mouse ICAM-1 cDNA into the mouse Ltk⁻ fibroblast line DAP-3 under HAT selection (Jaulin et al., 1992). DLD-1 cells which were derived from human colon carcinomas (Dexter et al., 1979) were purchased from ATCC (American Type Culture Collection, 10801 University Boulevard, Manassas, Va. 20110-2209). The B6/WT-3 cells were derived by SV40 transformation of C57BL/6 embryo fibroblasts as described by Pretell et al. (1979) and were obtained from Louisiana State University Health Sciences Center, Shreveport, La.

MAbs used in this study included the followings: 30-5-7 and 64-3-7 which recognize the folded and open forms of L$^d$, respectively (Lie et al., 1991 and Smith et al., 1992); mAbs B8-24-3 and 15-5-5 (purchased from ATCC) which recognize folded K$^b$ and D$^k$, respectively; and mAb 25D-1.16 (obtained from, NIH, Rockville, Md.) which recognizes K$^b$+SIIN-FEKL (SEQ ID NO: 18) peptide (Porgador et al., 1997). The OVA-derived peptide SIINFEKL (SEQ ID NO: 18) and SIYR peptide SIYRYYGL (SEQ ID NO: 20) were synthesized on a peptide synthesizer (model 432a; PE Applied Biosystems, Foster City, Calif.). All cells were maintained in complete medium (either DMEM or RPMI 1640) which included 1 mM sodium pyruvate, 0.1 mM non-essential amino acids, 2 mM glutamine, 25 μM HEPES, and 100 U/ml penicillin/streptomycin and supplemented with 10% heat inactivated bovine calf serum (HyClone Laboratories, Logan, Utah).

The QL9 peptide QLSPFPFDL (SEQ ID NO: 19), the OVA-derived peptide SIINFEKL (SEQ ID NO: 18) and SIYR peptide SIYRYYGL (SEQ ID NO: 20) were synthesized using Merrifield's solid phase method (1963) on a peptide synthesizer (model 432A: Applied Biosystems, Foster City, Calif.). Peptides were purified by reverse phase HPLC and purity (>95%) was assessed as described by Gorka et al. (1989).

DNA Constructs

Table 5 lists single chain constructs and sequences of some peptide antigens and some linkers. All PCRs were performed using Expandase (Roche Molecular Biochemicals, Indianapolis, Ind.) under standard conditions and the amplified portions of each construct were sequenced for verification.

second linker of 15-20 residues, $(G_4S)_{3-4}$, then the mature $K^b$ class I heavy chain sequence. Constructs were expressed from the pIRES.neo vector (Clontech Laboratories, Palo Alto, Calif.). The 64-3-7 epitope-tagged $K^b$ mutant ($K^b$R48Q.R50P) was described previously (Myers, N. B. et al., J. Immunol. 165: 5656-5663, 2002.

The QL9.β2-microglobulin.$L^d$ construct was generated by engineering an Avr II site at the junction between the QL9 peptide and the beginning of the linker. Two PCR fragments, one encoding the β2-microglobulin ignal peptide and the QL9 peptide and cut with Xba I/Avr II and the other one encoding the linker+β2-microglobulin residues 1-27 and cut with Avr II/Sna BI cells were cloned into the Xba I and Sna BI sites of RSV.5.neo. β2-microglobulin $L^d$ by 3-piece ligation with the Rapid DNA Ligation Kit (Roche Molecular Biochemicals), to create RSV.5.neo.QL9.β2-microglobulin.$L^d$. To increase expression efficiency after stable transfection, all these constructs were subcloned into the pIRES.neo vector (Clontech, Palo Alto, Calif.).

The MCMV.β2-microglobulin.$L^d$, p29.β2-microglobulin.$L^d$ and OVA.β2-microglobulin.$K^b$ constructs were pre-

TABLE 5

Composition of the single chain constructs

| Name of Construct | Peptide | First Linker | Second Linker |
|---|---|---|---|
| $β_2m^b.L^d$ | n.a. | n.a. | $(G_4S)_3$ (SEQ ID NO: 13) |
| $β_2m^b(120).K^b$ | n.a. | n.a. | $(G_4S)_4$ (SEQ ID NO: 14) |
| QL9.$β_2m^b.L^d$ | QLSPFDFDL (SEQ ID NO: 19) | $(G_4S)_2$ (SEQ ID NO: 11) | $(G_4S)_3$ (SEQ ID NO: 13) |
| MCMV.$β_2m^b.L^d$ | YPHGMPTNL (SEQ ID NO: 20) | $(G_4S)_2$ (SEQ ID NO: 11) | $(G_4S)_3$ (SEQ ID NO: 13) |
| p29.$β_2m^b.L^d$ | YPNVNIHNF (SEQ. ID NO: 21) | $G_3ASG_4S$ (SEQ ID NO: 27) | $(G_4S)_3$ (SEQ ID NO: 13) |
| OVA.$β_2m^b·K^b$ (10/15) | SIINFEKL (SEQ ID NO: 18) | $G_3ASG_4S$ (SEQ ID NO: 27) | $(G_4S)_3$ (SEQ ID NO: 13) |
| OVA.$β_2m^b·K^b$ (10/20) | SIINFEKL (SEQ ID NO: 18) | $G_3ASG_4S$ (SEQ ID NO: 27) | $(G_4S)_4$ (SEQ ID NO: 14) |
| OVA.$β_2m^b·K^b$ (15/20) | SIINFEKL (SEQ ID NO: 18) | $G_3AS(G_4S)_2$ (SEQ ID NO: 12) | $(G_4S)_4$ (SEQ ID NO: 14) |

The β2-microglobulin.$L^d$ and β2-microglobulin $K^b$ constructs were made in two steps. First, an XbaI/BamHI cut PCR fragment encoding the β2-microglobulin coding sequence and the first 10 amino acid residues of the linker were cloned into the XbaI/BamHI sites of the mammalian expression vector RSV5.neo (Long, E. O., et al., Human Immunol. 31: 229-235, 1991) to create RSV.5.neo.β2-microglobulin+linker. Second, a BamHI cut PCR fragment encoding the last 7 amino acid residues of the linker and the mature portion of either $L^d$ or $K^b$ cDNA were cloned into the Bam HI site of RSV.5.neo.β2-microglobulin+linker to create RSV.5.neo.β2-microglobulin.$L^d/K^b$.

Constructs were produced using standard techniques and were confirmed by DNA sequence analysis. The $β_2m^b$ $K^b$ constructs encode, in amino-to-carboxy terminal order, $β_2$-$m^b$, a linker of 15 or 20 residues consisting of $(G_4S)_{3-4}$, and the mature $K^b$ H chain sequence. The OVA.$β_2m^b.K^b$ constructs encode, in amino-to-carboxy terminal order, the leader sequence of $β_2m^b$, the SIINFEKL sequence, a first linker of 10 or 15 residues $(G_4S)_{2-3}$, the mature $β_2m^b$ sequence, a pared using the same method. The epitope tagged $K^b$ mutant ($K^b$R48Q, R50P) was described previously (Myers, N. B. et al. J. Immunol. 165: 5656-5663, 2000). The different linker variants were made by PCRs using Nhe I and Bsp EI sites engineered into the first and second linkers, respectively. The K3 cDNA was amplified by PCR from a K3 encoding plasmid kindly obtained from Washington University, St. Louis, Mo. and cloned into the Eco RI and Bam HI sites of pIRES.puro2 (Clontech). The various constructs were transfected into LM1.8, DLD-1 or B6/WT-3 cells using transfection reagents LIPOFECTIN (Life Technologies, Gaithersburg, Md.) or FUGENE 6 (Roche Molecular Biochemicals) according to manufacturer's instructions, Neomycin resistance was selected in 0.6 mg/ml genetic-in (Life Technologies) and puromycin resistance was selected in 5 11 g/ml puromycin (Sigma, St. Louis. MO).

Cytotoxic Lymphocyte (CTL) Generation and Maintenance

The $L^d$-alloreactive CTL clone, 2C, was obtained from MIT, Cambridge, Mass. It was grown in sensitization medium [complete RPMI 1640 supplemented with 10% heat inactivated fetal calf serum (HyClone Laboratories), 50 µM 2-ME, 10 U/ml Ri1-2] and maintained by weekly restimulation with irradiated (2,000R) BALB/c splenocytes ($2.5 \times 10^5$ responders and $5 \times 10^6$ stimulators) in 24 well plates at 2 ml per well. The OT-1 T cells were derived by stimulating $2.5 \times 10^6$ OT-1 splenocytes with $5 \times 10^6$ irradiated B6 splenocytes in sensitization medium in the presence of $5 \times 10^{-6}$M SIINFEKL (SEQ ID NO: 18) but without Ri1-2 for 5 days. Thereafter, the OT-1 line was restimulated weekly with 10 U/ml Ri1-2 at $5 \times 10^5$ responders per $5 \times 10^6$ stimulators. To test the immunogenicity of the single chain constructs, $7.5 \times 10^6$ responding (C3H×B6) F1 splenocytes were co-cultured with $3.5 \times 10^5$ irradiated (10,000R) LM1.8-$\beta$2-microglobulin L20).etK$^b$ cells in the presence of $1 \times 10^{-4}$M SIINFEKL peptide or LM1.8-OVA.$\beta$2m$^b$.etK$^b$ (15/20) cells in 24-well Linbro trays containing 2 ml sensitization medium without Ri1-2. After 5 days, they were restimulated in sensitization medium without IL-2 at $2.5 \times 10^6$ responders per $3.5 \times 10^5$ stimulators with $1 \times 10^{-4}$M SIINFEKL peptide (for LM1.8-$\beta_2$m(L20).etK$^b$ cells). Thereafter, they were restimulated weekly in the presence of 10 U/ml Ri1-2 at $2.5 \text{-} 5 \times 10^5$ responders per $3.5 \times 10^5$ stimulators with $1 \times 10^{-5}$M SIINFEKL peptide (for LM1.8-$\beta_2$m(L20).etK$^b$ cells).

$^{51}$Cr Release Assay $1 \times 10^6$ target cells were labeled with 150-200 µCi of $^{51}$Cr (Na$^{51}$CrO$_4$, NEN, Boston, Mass.) in 0.2-0.3 ml of complete RPMI 1640 medium+10% bovine calf serum at 37° C. in 5% CO$_2$ for 1-2 hours. Effector cells were plated into round bottom 96-well microtiter plates at various concentrations in the absence or continuous presence of peptide, and $2 \times 10^3$ washed target cells per well were added. The plates were centrifuged at 50×g for 1 minute and incubated for 4 hours at 37° C. in 5% CO$_2$. Radioactivity in 100 µl of supernatant was measured in an Isomedic gamma counter (ICN Biomedicals, Huntsville, Ala.). The mean of triplicate samples was calculated, and percentage $^{51}$Cr release was determined according to the following equation: percentage $^{51}$Cr release=100×((experimental $^{51}$Cr release–control $^{51}$Cr release)/(maximum $^{51}$Cr release–control $^{51}$Cr release)), where experimental $^{51}$Cr release represents counts from target cells mixed with effector cells; control $^{51}$Cr release represents counts from target cells incubated with medium alone (spontaneous release); and maximum $^{51}$Cr release represents counts from target cells lysed by the addition of 5% Triton X-100. Spontaneous release ranged from 5-20%.

Flow Cytometry and Peptide Induction $3\text{-}5 \times 10^5$ cells were washed and incubated on ice in FACS medium (PBS containing 1% BSA and 0.1% NaN$_3$) in the presence of a saturating concentration of mAb for 30-60 minutes, washed twice in FACTS medium, and incubated on ice with a saturating concentration of FITC-labeled, Fc-specific goat anti mouse-IgG F(ab')$_2$ (ICN Biomedicals, Aurora, Ohio) or PE-labeled, goat anti mouse IgG (Pharmingen, San Diego, Calif.) for 20 min. Cells were washed twice and resuspended in FACS medium. Viable cells, gated by forward and side scatter, were analyzed and a FACSCALIBUR (Becton Dickinson, San Jose, Calif.) equipped with an argon ion laser tuned to 488 nm and operating at 150 Mw. The data are expressed as linear fluorescence values obtained from log-amplified data using CELLQUEST Software (Becton Dickinson). Cells incubated with an irrelevant primary mAb followed by secondary antibodies were used as negative controls. For peptide incubation, $1 \times 10^6$ cells were incubated with the indicated concentration of peptide in a final volume of 2 ml complete medium at 37° C. overnight in a 6 well plate.

Immunoprecipitation and Western Blotting

Immunoprecipitations and Western blots. Cells were lysed in 10 mM Tris buffered saline pH 7.4 (TBS) containing 1% digitonin Wako, Richmond, Va.) with 20 mM iodoacetamide (IAA) and 0.2 mM of freshly added PMSF (Sigma). Saturating amounts of the primary antibody were added to the lysis buffer. Post-nuclear lysates were added to protein A-SEPHAROSE CL-4B (Amersham Pharmacia, Uppsala Sweden) for 60 minutes on ice and protein A-bound material was washed in 0.1% digitonin in TBS. Immunoprecipitates were eluted from protein A by boiling for 5 minutes in elution buffer (LDS sample buffer; Invitrogen, Carlsbad, Calif.). Samples were electrophoresed on 7% tris-acetate polyacrylamide gels (Invitrogen) and transferred to IMMOBILON-P PVDF membranes (Millipore, Bedford, Mass.). After overnight blocking in 10% dried milk in PBS-0.05% Tween 20, membranes were incubated with mAb 64-3-7 for 1 hour, washed three times with PBS-0.05% Tween 20, and incubated for 1 hour with biotin-conjugated goat anti-mouse IgG$_{2b}$ (Caltag, San Francisco, Calif.). Following three washes with PBS-0.05% Tween 20, membranes were incubated for hour with streptavidin-conjugated HRP (Zymed, San Francisco, Calif.), washed three times with PBS-0.03% Tween 20, and incubated with ECL chemiluminescent reagents (Amersham Pharmacia Biotech, Piscataway, N.J.) prior to exposure to BIOMAX-MR film (Eastman Kodak, Rochester, N.Y.).

Pulse-chase and immunoprecipitations. After a 45 min pre-incubation in Met/Cys-free medium (DMEM with 5% dialyzed FCS), cells (at $20 \times 10^6$ cells/ml) were pulse labeled with Express $^{35}$S-Met/Cys labeling mix (Perkin Elmer Life Sciences, Boston, Mass.) at 300 µCi/ml for 10 min. Cells were then washed extensively, an aliquot removed for the zero time point, and the remaining cells returned to culture at 37 degrees for the indicated times. For immunoprecipitations, labeled cells were lysed in 1% NP-40 (Sigma) dissolved in TBS with 20 mM IAA and 5 mM PMSF. Post-nuclear lysates were pre-cleared over protein A-SEPHAROSE CL-4B for 30 min on ice. Lysates were then transferred to protein A-SEPHAROSE pellets containing the appropriate pre-hound mAbs. After binding for 45 min on ice, protein A pellets were washed 4 times with 0.1% NP-40 in TBS, and bound proteins were eluted by boiling in 10 mM tris-Cl, PH 6.8+0.5% SDS+1% 2-mercaptoethanol. Eluates were mixed with an equal volume of 100 mM sodium acetate, pH 5.4 and digested overnight with 1 Mu endoglycosidase H (ICN, Costa Mesa, Calif.) that was reconstituted in 50 mM sodium acetate, pH 5.4. Following SDS-PAGE, gels were treated with Amplify (Amersham), dried, and exposed to BIOMAX-MR film.

Example 9

This example illustrates correlation of the level and quality of surface expression of SCT molecules with the known affinity of peptide binding to an MHC class I molecule when non-covalently attached. To serologically determine the quality of an SCT and test the role of peptide affinity, an SCT was prepared containing a QL9 antigen peptide, $\beta$2-microglobulin and a L$^d$ heavy chain.

Monoclonal antibodies (mAbs) are available which distinguish L$^d$ heavy chain conformation as determined by occupancy with high affinity peptide ligands (Lie et al. 1991; Smith et al., 1992 and 1993; Yu et al., 1999). More specifically, two mAbs, 30-5-7 and 64-3-7, recognize the folded (peptide loaded) and open (peptide empty) conformers of L$^d$. Evidence for the reciprocal specificity of the two mAbs includes the fact that incubation with high affinity peptide ligands leads to an increase in 30-5-7+ $L^d$ and a decrease in 64-3-7+ $L^d$ affinity, whereas acid stripping leads to a sharp decrease in 30-5-7+ $L^d$ and a proportional increase in 64-3-7+ $L^d$ affinity. Thus these two mAbs can be used in tandem to assess the effect of covalent linkage on the expression of the resultant SCT.

For the antigen peptide portion of an SCT, a sequence encoding the nonomeric peptide termed QL9, QLSPFPFDL, (SEQ ID NO: 19) (Sykulev et al. 1994) was initially used to make the single chain construct QL9. B2-microglobulin.$L^d$. The QL9 peptide is recognized by a well characterized $L^d$-restricted alloreactive CTL clone 2C (Udaka et al., 1992). As a peptide minus control construct, β2-microglobulin.$L^d$, was generated by linking β2-microglobulin and $L^d$ together with a 15 residue flexible linker. These two constructs, QL9.β2-microglobulin.$L^d$ and β2-microglobulin.$L^d$, were then stably transfected into the human cell line DLD-1, which fails to express endogenous β2-microglobulin Bicknell et al., 1994). Clonal transfectants expressing QL9.β2-microglobulin.$L^d$ or β2-microglobulin.$L^d$ were then examined by flow cytometry with mAbs 30-5-7 and 64-3-7.

As shown in FIG. 1A (panels a and b), both constructs were expressed on the surface of the DLD-1 transfectants indicating that covalent linkage of β2-microglobulin can override the requirement for endogenous β2-microglobulin, in agreement with published observations (Toshitani et al., Proc. Nat'l Acad. Sci. 93: 236-240, 1996). In addition, it was found that the QL9.β2-microglobulin.$L^d$ construct containing all three elements of fully assembled $L^d$ can fold correctly and be expressed on the cell surface as detected by the mAb 30-5-7 that detects an $L^d$ conformation acquired after binding high affinity peptide ligands.

A comparison of the percentage of QL9.β2-microglobulin.$L^d$ vs. β2-microglobulin.$L^d$ in the open vs. folded conformation was also made. Whereas 39% of surface β2-microglobulin.$L^d$ molecules were detected in an open conformation, only 22% of surface QL9.β2-microglobulin.$L^d$ were detected in an open conformation. This difference suggests that covalent attachment of peptide improved the efficiency of peptide loading and reduced, but did not eliminate peptide dissociation. Relative to other class I molecules the $L^d$ molecule is known to be highly susceptible to peptide and β2-microglobulin issociation (Hansen, T., et al., Immunol. Today 21: 83-88, 2000). Indeed this propensity to disassemble results in normal (unattached) $L^d$ having a lower level of surface expression relative to other class I molecules. The propensity to disassemble makes $L^d$ an ideal candidate to test the role of peptide affinity in expression of SCT molecules. For these comparisons, SCT molecules were constructed that included two different $L^d$ ligands, MCMV (Reddehase, M. J., et al. Nature 337: 651-653, 1989) and p29 (Corr, M., et al., J. Exp. Med. 176: 1681-1692, 1992). In previously published data, it was determined that QL9/$L^d$ and MCMV/$L^d$ complexes have a half life of about 2 hours, whereas p29/$L^d$ complexes have a half life of greater that 6 hours (Smith, J. D. et al., J. Exp. Med. 175: 191-202, 1992). Indeed the p29 peptide was the only peptide to fold recombinant $L^d$ heavy chains to a sufficient extent to obtain crystals (Balendiran, G. K., et al., Proc. Nat'l. Acad. Sci. USA 94: 6880-6885, 1997). In agreement with the studies using $L^d$ ligands in solution, the MCMV.β2-microglobulin.$L^d$ construct behaved very similarly to QL9.β2-microglobulin.$L^d$ in that 22% of the surface MCMV.β2-microglobulin.$L^d$ molecules were detected in the open conformation (FIG. 1A, panel c). By contrast, the p29.$β_2m^b$.$L^d$ construct exhibited a higher level of expression of the folded conformers and a much lower expression of the open conformers which corresponds to roughly 8% of the surface pool (FIG. 1A, panel d). Identical FACS profiles were obtained when a second independent transfection of DLD-1 cells was performed with these constructs (data not shown). Thus, SCT with peptides known to bind better in solution also make more stable single chain molecules. Therefore, it was found that the level and quality of surface expression of non-covalently bound SCT correlates with the affinity of peptide bind to class I.

Example 10

Figure 1B:
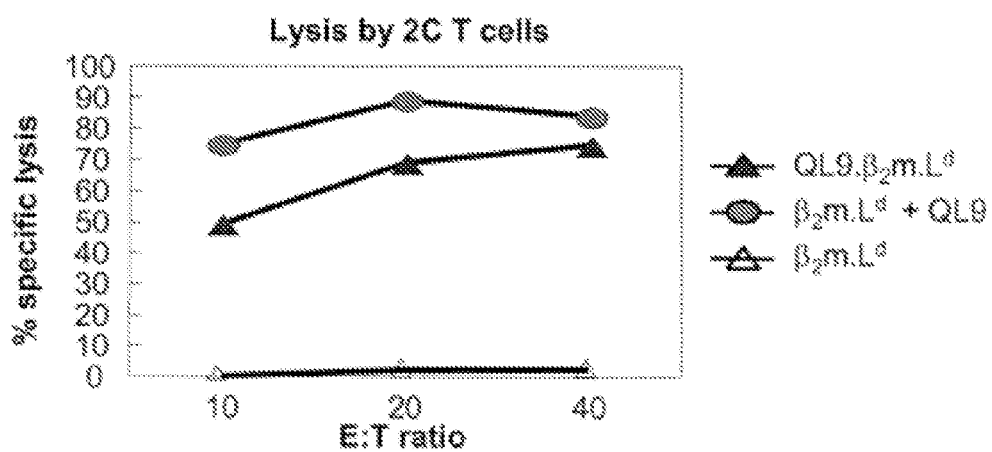
FIG. 1B illustrates cytotoxic T cell recognition of QL9.$\beta 2m^b$.$L^d$ expressed by DLD-1 cells.

This example illustrates SCT recognition by T cells and mAb specific for class I/peptide complexes. In these experiments, SCT constructs were tested with the 2C CTL clone to see if they maintained structural integrity as seen by specific T cells. The CTL clone specifically recognizes $L^d$/QL9 complexes (Sykulev, Y., et al., Proc. Nat'l. Acad. Sci. USA 91: 236-240, 1994). The β2-microglobulin.$L^d$ construct expressed on DLD-1 cells were not recognized by 2C T cells unless exogenous QL9 peptide was added (FIG. 1B). By comparison, DLD-1 cells expressing QL9.β2-microglobulin.$L^d$ molecules were recognized by 2C T cells in a dose dependent manner, similar to 2C T cell recognition of DLD-1 cells expressing the β2-microglobulin.$L^d$ construct when treated with exogenous QL9 peptide. Similar recognition by $L^d$/MCMV specific T cells was seen with the DLD-1 cells transfected with the MCMV.β2-microglobulin.$L^d$ construct (data not shown). Thus SCTs function as targets for antigen-specific T cells.

Figure 2:
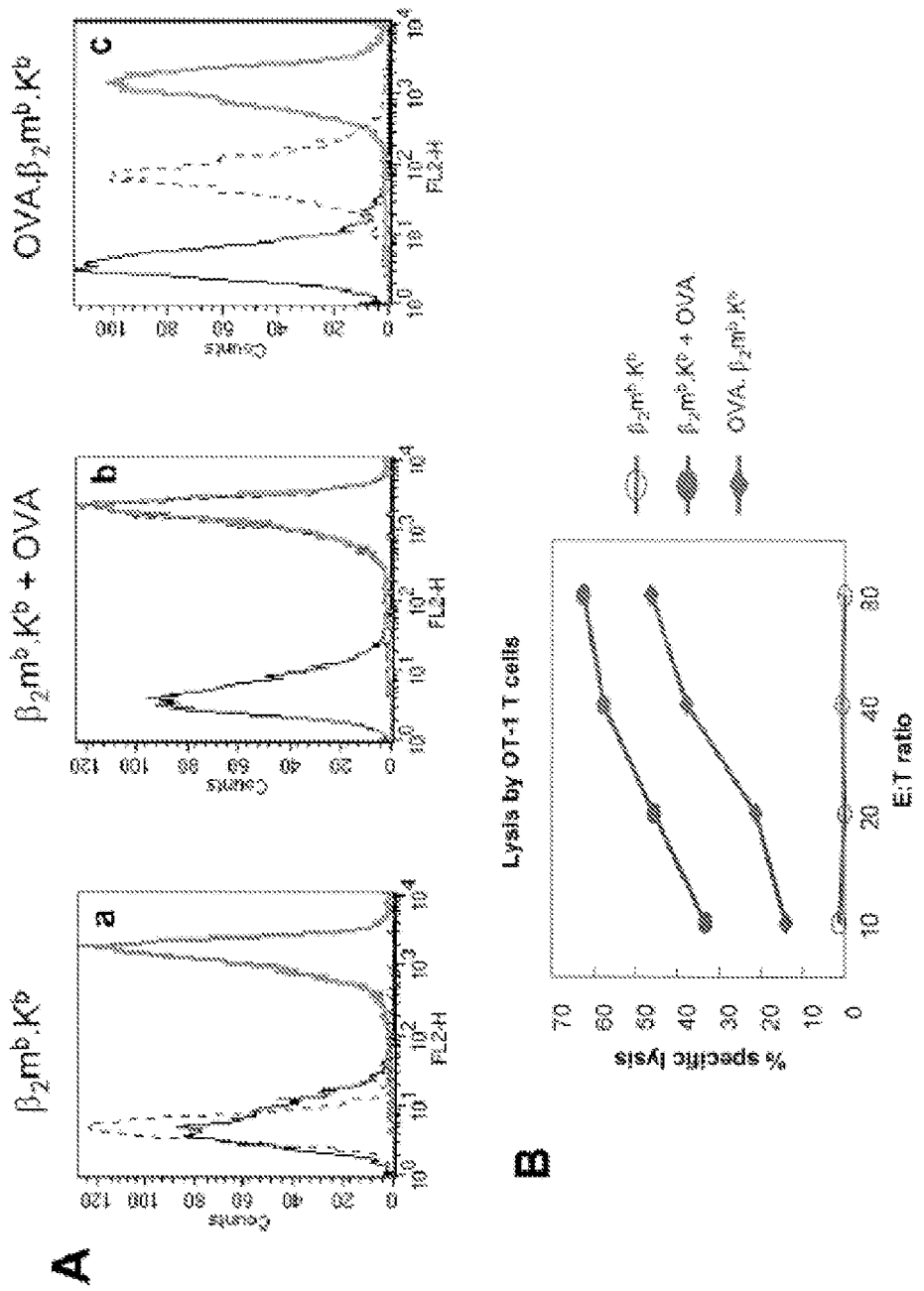
FIG. 2 illustrates flow cytometric analysis of cell surface expression and T cell recognition of OVA. $\beta$2-microglobulin.$K^b$ compositions.

SCT constructs were also prepared containing a $K^b$ heavy chain. $K^b$ was chosen because it is a prototypical class I molecule that has been used extensively for structure-function analyses. Furthermore, an mAb (25D-1.16) is available that specifically recognizes $K^b$+ the ovalbumin derived OVA peptide, SIINFEKL (SEQ ID NO: 18) (Porgador, A., et al. Immunity 6: 715-726, 1997). This reagent allowed the $K^b$/OVA complexes to be monitored serologically. Thus, a new construct, OVA.β2-microglobulin.$K^b$, was made by replacing the sequence encoding the p29 peptide and $L^d$ heavy chain from p29.β2-microglobulin.$L^d$ with sequence encoding the OVA peptide and the $K^b$ heavy chain. A corresponding β2-microglobulin.$K^b$ construct (β2-microglobulin+15 residue linker+$K^b$) was made for comparison. These constructs were transfected into mouse L cells co-expressing ICAM-1 (LM1.8) or DLD-1. The flow cytometry profiles of the LM1.8 transfectants are shown in FIG. 2A. When stained with anti-$K^b$ mAb B8-24-3 that is conformationally sensitive but not peptide specific, both constructs gave high level of expression. In accordance with its specificity, mAb 25D-1.16 was unreactive with the β2-microglobulin.$K^b$ construct unless exogenous OVA peptide was provided (Porgador et al. 1997). By contrast, the OVA.β2-microglobulin.$K^b$ construct was reactive with mAb 25D-1.16. This could explain the relatively low level of 25D-1.16 expression. In parallel, the integrity of the OVA.β2-microglobulin.$K^b$ construct was also tested by T cell recognition. In this case, $K^b$/OVA specific T cells derived from OT-1 transgenic mice were used (Hogquist et al., 1994). As shown in FIG. 2B, the OVA.β2-microglobulin.$K^b$ transfectants were lysed by these OT-1 derived T cells. Thus, the SCT made with both $L^d$ and $K^b$ are capable recognition by peptide specific T cells. In addition, the $K^b$/OVAN SCT can be detected by an mAb specifically recognizing this particular class I/peptide combination.

Example 11

Figure 3:
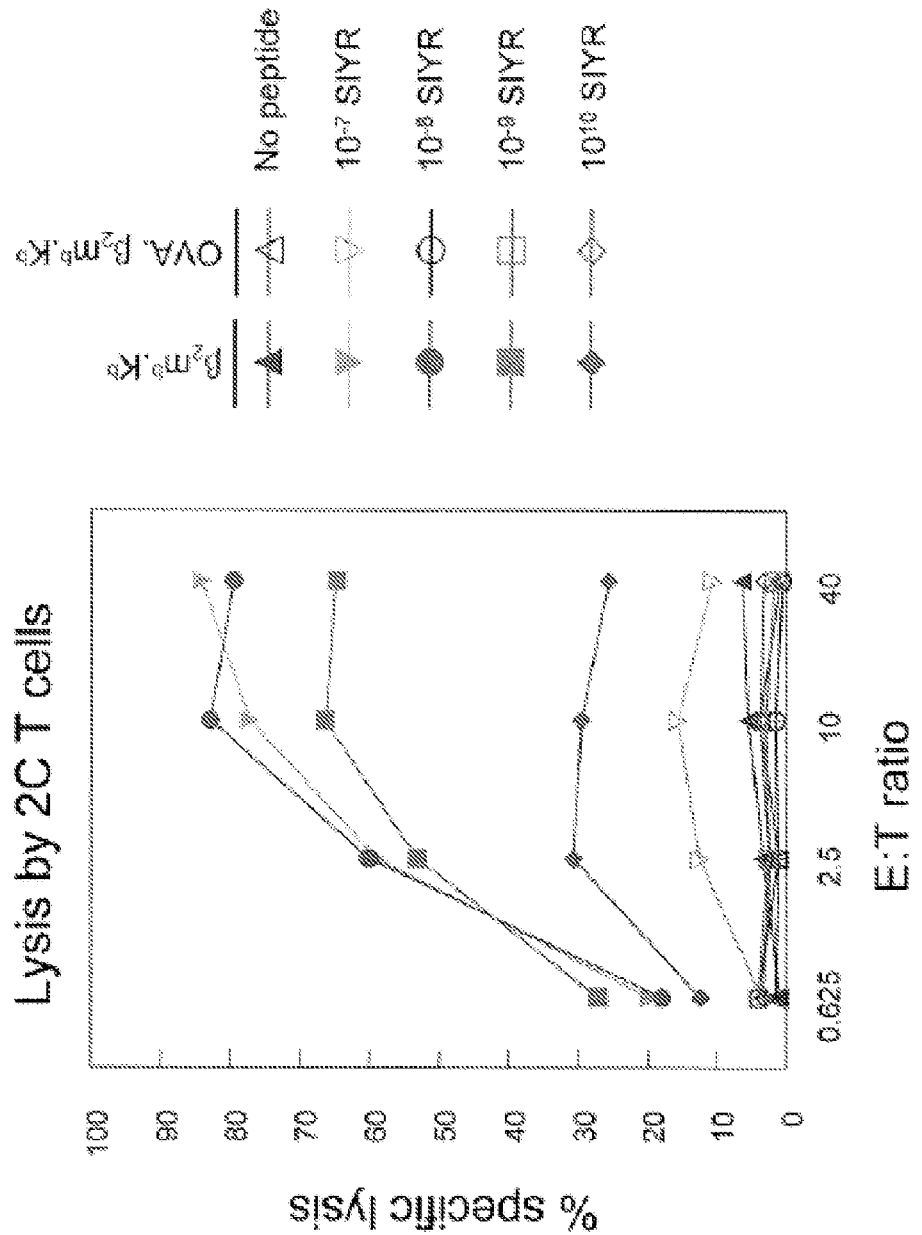
FIG. 3 illustrates accessibility of an SCT to loading with exogenous peptide, as indicated by resistance of an OVA.$\beta$2-microglobulin.$K^b$ SCT to displacement by high affinity $K^b$ binding peptide.

This example illustrates accessibility of SCT to loading with exogenous peptide. To assess the stability of the covalent peptide which is anchored in the peptide binding groove, peptide competition assays were performed. In this assay, the relative accessibility of the OV A.β2-microglobulin.$K^b$ construct to a different $K^b$ ligand was monitored. To do this, the 2C CTL clone was again utilized because it also recognizes $K^b$/SIYR (SEQ ID NO: 42) complex. SIYR (SEQ ID NO: 42) is a synthetic peptide identified from a peptide library (U daka et al., 1996) and has been reported to be as avid a $K^b$ binder as is SIINFEKL (SEQ ID NO: 18) (Tallquist, M.D., et al., J. Immunol. 160: 802-908, 1998). When LM1.8-β2-microglobulin.$K^b$ or LM1.8-OVA.β2-microglobulin.$K^b$ transfectants were compared as targets for 2C T cells after overnight incubation with graded doses of SIYR (SEQ ID NO: 42) peptide (FIG. 3), the OVA.β2-microglobulin.$K^b$ construct was completely resistant to displacement by exogenous SIYR (SEQ ID NO: 42) peptide at a concentration as high as $10^{-7}$M. Contrary to this, there was significant lysis of LM1.8-β2-microglobulin.$K^b$ transfectants at a concentration as low as $10^{-10}$M. This finding suggests that the OVA.β2-microglobulin.$K^b$ construct is more than 1000-fold less accessible to loading by an exogenous peptide of comparable affinity, when compared with the β2-microglobulin.$K^b$ constructs loaded with endogenous peptides. Thus, the covalent peptide is stably bound in the SCT peptide binding groove.

Example 12

Figure 4A:
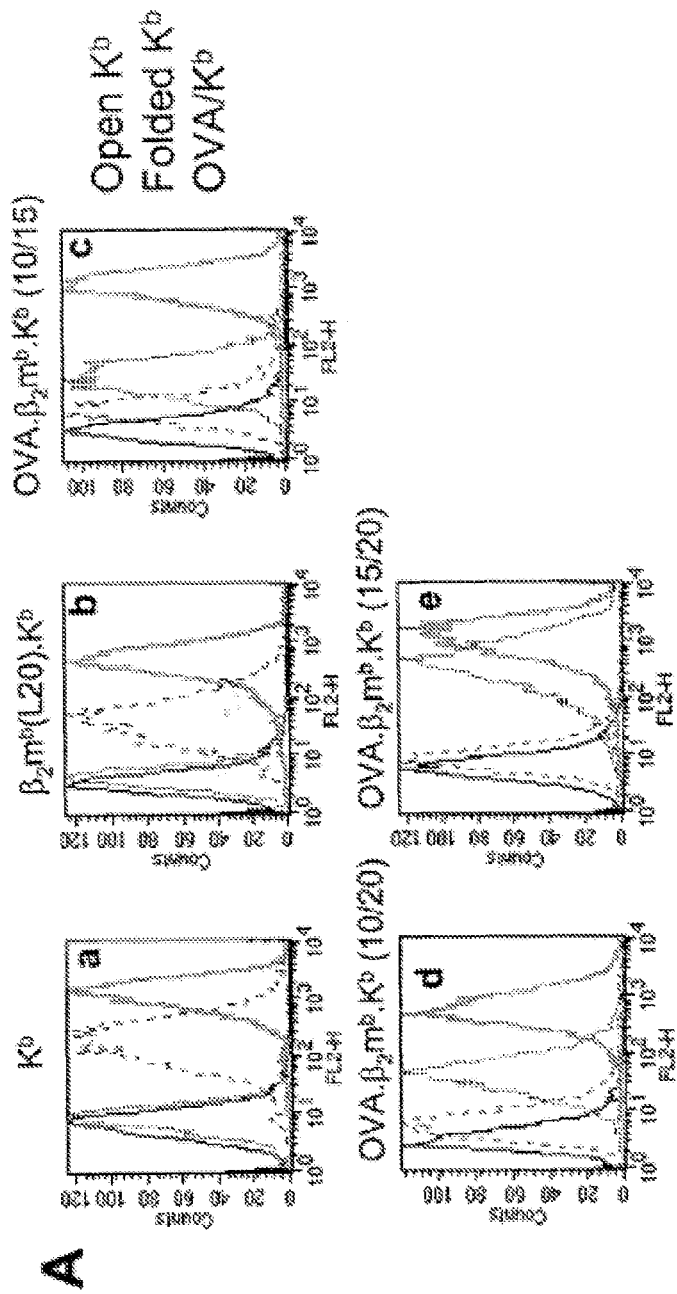
FIG. 4A illustrates expression of SCT's with varying linker lengths.
Figure 4B:
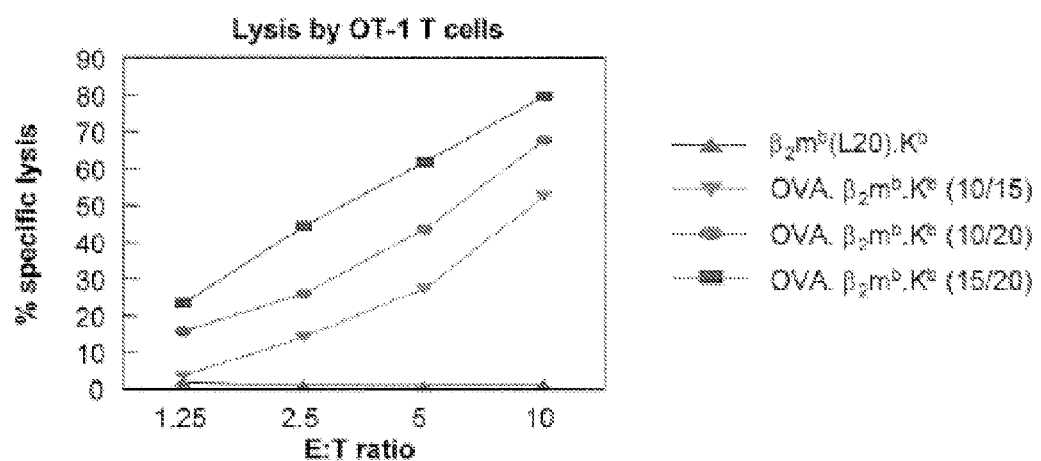
FIG. 4B illustrates cytotoxic T cell recognition of the SCT's of varying length.

This example illustrates the effects of varying the linker length on the immune recognition of a single chain trimer molecule. In these experiments, another set of OVA.β2-microglobulin.$K^b$ constructs with longer linkers compared to those disclosed above was created. In addition to varying the linker length, a double mutation R48Q, R50P was introduced into the $K^b$ heavy chain to allow the transfer of the epitope detected by the mAb 64-3-7 which recognizes the open conformers (Yu, Y. Y. L., Int. Immunol. 11: 1897-1906, et al., 1999). This epitope tagging (et) has been successfully applied to a number of class Ia and class Ib molecules including $K^b$, $K^d$, HLA-B27 and H2-M3, and found to remain specific for open conformers of the epitope tagged molecule without altering peptide binding specificity (Myers, N. B. et al. J. Immunol. 165: 5656-5663, 2000; Yu, Y. Y. L., Int. Immunol. 11: 1897-1906, et al., 1999; Harris, M. R., et al., Int. Immunol. 13: 1275-1282, 2001; Lybarger, L., et al., J. Immunol. 167: 2097-2105, 2001). A total of three constructs which were named OVA.β2-microglobulin.$K^b$ followed by a bracket indicating the length of the two linkers were made. Thus, for example, OVA.β2-microglobulin.$K^b$ (10/15) has a 10 residue linker between the OVA peptide and the β2-microglobulin and a 15 residue linker between β2-microglobulin and the $K^b$ heavy chain. The other two linker combinations were 10/20 and 15/20. These constructs were compared by flow cytometry to unattached $K^b$ or β2-microglobulin (L20).$K^b$ (20 residue linker between β2-microglobulin nd $K^b$) molecules. As shown in FIG. 4A, all of these constructs gave rise to high levels of expression of folded $K^b$ (B8-24-3) on LM1.8 cells. However, when examined for the presence of open conformers (64-3-7), only the $K^b$ (part a) and β2-microglobulin (L20).$K^b$ (part b) constructs expressed an appreciable amount (>10% when expressed as a fraction of the sum of B8-24-3 and 64-3-7 fluorescence intensity). Furthermore, the open conformers associated with the β2-microglobulin (L20).$K^b$ construct all but disappeared upon exogenous feeding with the OVA peptide (data not shown) thus reaffirming their "peptide-empty" nature. In stark contrast, the other three transfectants, namely, LM1.8-OVA.β2-microglobulin.$K^b$ (10/15), LM1.8-OVA.β2-microglobulin.$K^b$ (10/20) and LM1.8- OVA.β2-microglobulin.$K^b$ (15/20) expressed less than 1% open conformers. Thus, the covalent OVA peptide must be able to occupy the $K^b$ peptide binding groove virtually all the time. When mAb 25D-1.16 reactivity was compared, it was apparent that the linker combination of (15/20) was significantly better than the other two combinations. In parallel with the FACS profiles, the recognition by OT-1 derived T cells was also the best for the transfectants (FIG. 4B). Thus increasing the length of the flexible linkers results in improved recognition of the OVA.β2-microglobulin.$K^b$ construct by both the mAb 25D-1.16 and OT-1 T cells. This improved recognition with longer linkers in SCT could reflect better peptide positioning and/or reduced steric hindrance for TCR and Ab interaction. All subsequent experiments were preformed using OVAβ2-microglobulin $^b$.$K^b$ (15/20) molecules with such optimal linkers.

Example 13

Figure 5:
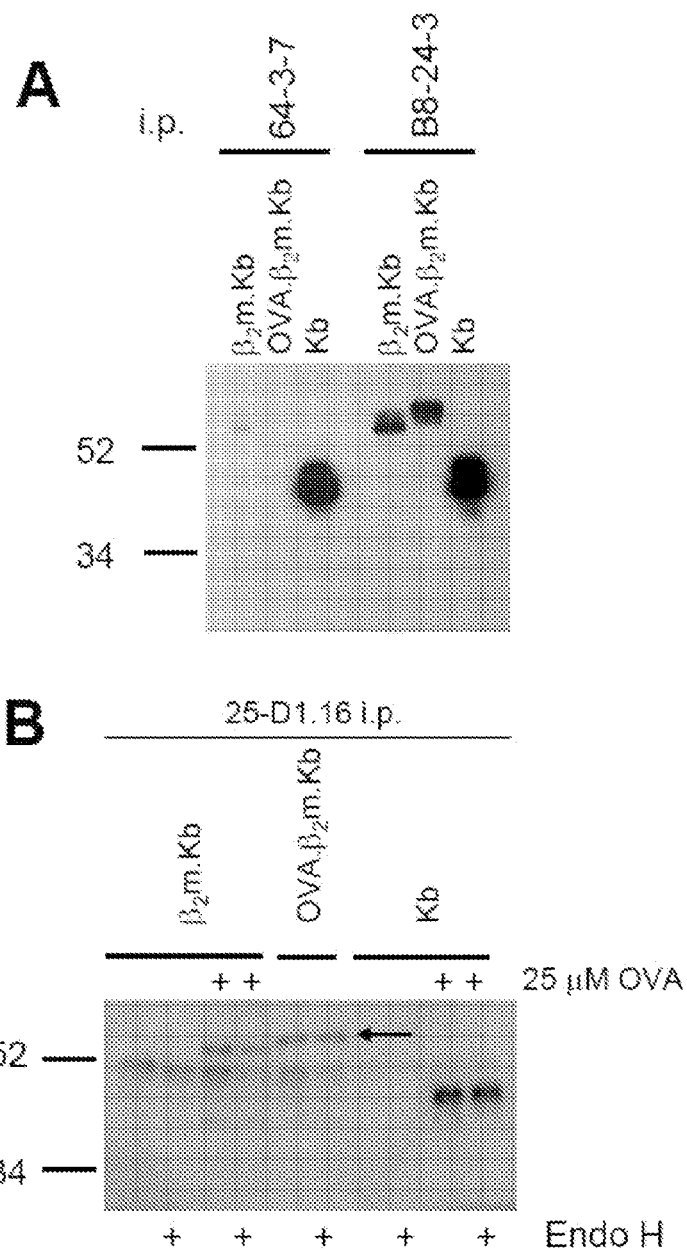
FIG. 5 illustrates biochemical stability of OVA.$\beta$2-microglobulin.$K^b$ SCT.

This example illustrates biochemical integrity of the SCT. To examine whether all of the components of the SCT remain intact at the cell surface (FIG. 3), biochemical analyses were performed to compare $K^b$, β2-microglobulin.$K^b$, and OVA.β2-microglobulin.$K^b$. Each of these molecules was immunoprecipitated from respective L cell transfectants and immunoblotted to compare the relative molecular weights of all three $K^b$ constructs. As shown in FIG. 5A, mAb 64-3-7 (specific for open heavy chains) precipitated high levels of $K^b$, but low to undetectable amounts of β2-microglobulin $K^b$ and OVA.β2-microglobulin $K^b$. By contrast, B8-24-3 (specific for folded $K^b$) was able to precipitate significant amounts of all three constructs. The differential reactivity with these two mAbs demonstrate that the covalent attachments to $K^b$ reduced the levels of open conformers existing at steady-state. In addition, this experiment demonstrated that the β2-microglobulin.$K^b$ and OVA.β2-microglobulin.$K^b$ covalent constructs exhibit a slower migration consistent with their expected molecular weights. Indeed, the migration of the OVA.β2-microglobulin,$K^b$ construct was even slower than β2-microglobulin.$K^b$, indicating that the covalent OVA peptide and linker remain attached. No breakdown products were evident, including fragments that would correspond in size to $K^b$ heavy chains from which the covalent appendages have undergone proteolysis. These results indicate that the preponderance of the single chain molecules, at steady-state, are structurally intact. The doublet bands seen with these constructs represent Endo H-sensitive (ER-resident) vs. Endo H-resistant (post-ER) (FIG. 5B). The β2-microglobulin.$K^b$ molecules were predominantly Endo H-sensitive, whereas the OVA.β2-microglobulin.$K^b$ molecules were predominantly Endo H-resistant. This observation suggests that addition of the covalent peptide facilitates faster ER to Golgi transport.

To demonstrate that the OVA peptide was not undergoing proteolysis from the SCT and then rebinding as an unattached peptide, precipitates were preformed using mAb 25-D1.16. To compare OVA.β2-microglobulin.$K^b$ molecules with $K^b$ molecules loaded with non-covalently attached OVA peptide, 25-D1.16 precipitates were also formed with β2-microglobulin.$K^b$ and $K^b$ constructs subsequent to overnight incubation with exogenous OVA peptide. FIG. 5C demonstrates that mAb 25-D1.16 precipitated OVA.β2-microglobulin.$K^b$, as well as β2-microglobulin.$K^b$ and $K^b$ molecules after incubation with exogenous OVA peptide. Importantly, the SCT migrated slightly slower than the β2-microglobulin.$K^b$ construct that was precipitated from cells incubated with exogenous peptide. Thus, these precipitates with mAb 25-D1.16 demonstrate that OVA.β2-microglobulin K$^b$ molecules retain covalently attached OVA peptide, rather than rebinding free OVA peptide after proteolysis of the SCT.

Example 14

This example illustrates accelerated folding and maturation of SCTs. To test whether direct covalent attachment of either β2-microglobulin or peptide/β2-microglobulin to the heavy chain increases the efficiency of folding, the maturation kinetics of the various K$^b$ constructs were compared using pulse-chase analysis. The data indicate that newly synthesized single chain molecules do, indeed, mature more quickly than K$^b$ alone. This was apparent both in terms of initial peptide-induced folding (revealed by a loss of 64-3-7 reactivity) and ER to Golgi transport (acquisition of Endo H resistance). Approximately one-half of the K$^b$ molecules were Endo H-resistant after 90 minutes, whereas virtually all of the SCTs were resistant at this time point (see mAb B8-24-3 precipitates). Furthermore, addition of the covalent OVA peptide appeared to enhance folding to a greater extent than addition of β2-microglobulin alone, since the 64-3-7$^+$ conformers of OVA.β2-microglobulin.K$^b$ were lost more rapidly than the 64-3-7$^+$.β2-microglobulin.K$^b$ molecules. Taken together, these data indicate that, by covalently appending all of the subunits required for full assembly, class I molecules can assume a folded conformation and traffic from the ER with high efficiency. These findings indicate that the kinetics of assembly with β2-microglobulin and peptide contribute to the overall rate of class I maturation and ER-to-Golgi transport.

Example 15

This example illustrates immunogenicity of SCTs. To test the ability of the single chain class I molecule to generate a T cell response, the ability of LM1.8 (H2$^k$) cells expressing OVA.β2-microglobulin.K$^b$ and β2-microglobulin.K$^b$ fed exogenous OVA peptide (10$^{-4}$M) to induce K$^b$/OVA specific T cell in vitro was compared. For this experiment, responder T cells from [C3H (H2$^k$)×B6 (H2$^b$)] F1 mice were used that potentially should respond to only K$^b$/OVA complexes presented by either OVA.β2-microglobulin.K$^b$ or peptide fed β2-microglobulin.K$^b$. Successful generation of antigen-specific CD8+ T cells typically requires in vivo priming, intracellular peptide loading or antigen pulsed, purified dendritic cells (Carbone and Bevan, J. Exp. Med. 169: 603-612, 1989: Mayordomo et al. Nature Med. 1: 1297-302, 1995). However, specific lysis was attainable after just 4 weekly rounds of stimulation splenocytes with cells expressing the OVA. β2-microglobulin.K$^b$ construct (data not shown). High levels K$^b$/OVA-specific lysis was observed after 5 weekly rounds of stimulation with this same construct (FIG. 2A, panel a). By comparison, after 5 weekly rounds of stimulation with cells expressing the β2-microglobulin.K$^b$ construct and fed 10$^{-4}$M continuous OVA peptide, little if any K$^b$/OVA-specific lysis was observed (FIG. 2A, panel b). Thus the single chain class I construct including peptide is superior in stimulating peptide specific T cells. Given that the OVA.β2-microglobulin.K$^b$ construct is more than a 1000 fold less accessible to exogenous peptide than the β2-microglobulin K$^b$ construct (FIG. 3), it is highly unlikely that the OVA.β2-microglobulin.K$^b$ construct is a more potent stimulator due to the covalent OVA peptide being clipped off and rebinding as a free peptide.

To demonstrate that SCTs retain immune recognition as intact structures in vivo, mice were vaccinated with DNA encoding OVA.β2-microglobulin.K and then tested for antibody production. DNA vaccination was preformed using allogeneic BALB/c mice to eliminate the possibility of cross presentation of the OVA peptide on self Kb molecules. After only two injections of DNA, 2/6 BALB/c recipients made significant antibodies (titer 1:16). These antibodies were found to be predominantly Kb/ova specific, since they did not detect Kb loaded with endogenous peptides (FIG. 6B), or an irrelevant peptide. Together these findings demonstrate that the OVA.β2-microglobulin.Kb single chain construct is highly immunogenic due to its capacity to remain covalently attached and to stimulate peptide-specific, class I restricted, CD8 T cells and antibodies.

Example 16

Figure 6:
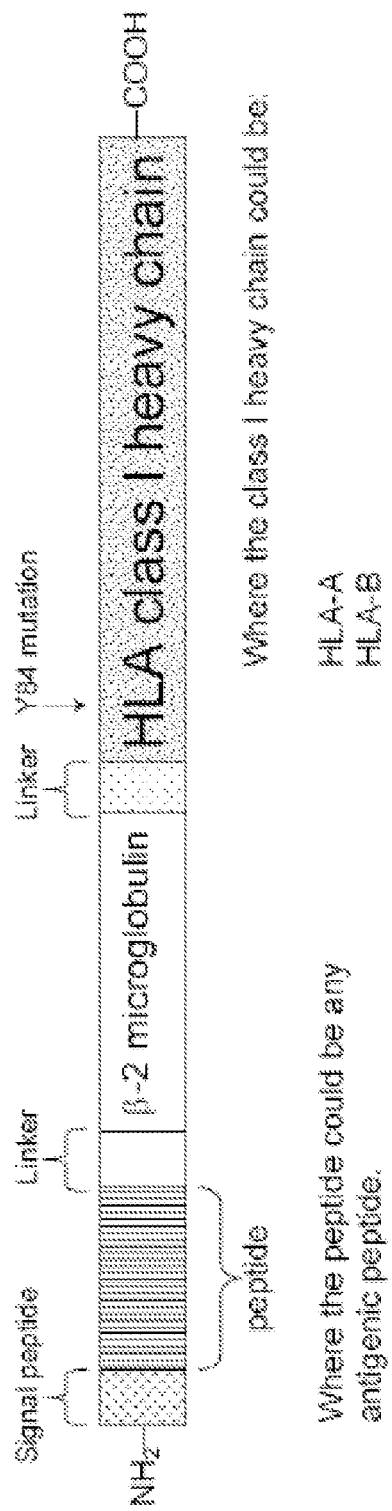
FIG. 6 illustrates structure of single chain trimers.

This example illustrates resistance of SCT to down regulation by the K3 protein of γ-HV68. To test the resistance of a single chain construct to down regulation by a virus protein, the K3 protein encoded by murine γ-HV68 was tested. In a recent report γ-HV68 K3 expression was shown to severely reduce K$^b$ and D$^b$ expression by inducing a rapid turnover of immature (EndoH-sensitive) class I molecules (Stevenson, P.G., et al., Proc. Nat'l Acad. Sci, USA 97: 8455-8460, 2000). To test whether single chain class I molecules were also susceptible to K3 mediated down regulation, a K3 cDNA was stably introduced into the LM1.8 transfectant expressing the OVA.β2-microglobulin.K$^b$ construct. As can be seen in FIG. 6B (panels a and b), the introduction of K3 almost completely shut down the endogenous D$^k$ expression while the OVA.β2-microglobulin.Kb expression remained largely unscathed. As a control, stable expression of K3 was found to sharply reduce the amount of endogenous K$^b$ (lacking any attachments) expressed on the cell surface of B6/WT-3 cells. Thus, the OVA.β2-microglobulin.K$^b$ single chain class I construct effectively escapes K3-mediated down regulation.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

All publications, patents, patent applications and other references cited in this application are herein incorporated by reference in their entirety as if each individual publication, patent, patent application or other reference were specifically and individually indicated to be incorporated by reference.

Aspects of the Present Teachings

Disclosed herein are various inventive teachings, including, without limitation, the following aspects.

ASPECT 1. A recombinant DNA molecule comprising a DNA sequence encoding a single chain trimer of a mature MHC molecule, the single chain trimer comprising in sequence:
(1) a peptide ligand segment;
(2) a first linker;
(3) a β2m segment;
(4) a second linker; and
(5) a class I heavy chain segment,
wherein the peptide ligand segment has a carboxy end, the β2m segment has amino and carboxy ends, and the heavy chain segment has an amino end, and wherein the peptide ligand segment is covalently linked via its carboxy end to the amino end of the β2m segment by the first linker, and wherein the β2m segment is covalently linked via its carboxy end to the amino end of the heavy chain segment by the second linker.

ASPECT 2. The recombinant DNA molecule of aspect 1 wherein the class I heavy chain segment is comprised of a HLA-A, HLA-B, HLA-C, 1a, 1b, H-2-K, H-2-Dd or H-2-Ld heavy chain.

ASPECT 3. The recombinant DNA molecule of aspect 1 wherein the class I heavy chain segment contains a mutated conserved residue.

ASPECT 4. The recombinant DNA molecule of aspect 3 wherein the tyrosine at position 84 is mutated.

ASPECT 5. The recombinant DNA molecule of aspect 1 wherein the first linker is comprised of at least 10 amino acid residues.

ASPECT 6. The recombinant DNA molecule of aspect 5 wherein the first linker is comprised of at least 15 amino acid residues.

ASPECT 7. The recombinant DNA molecule of aspect 6 wherein the first and second linkers are comprised of at least about 80 percent glycine, alanine or serine residues.

ASPECT 8. The recombinant DNA molecule of aspect 1 wherein the second linker is comprised of least 15 amino acid residues.

ASPECT 9. The recombinant DNA molecule of aspect 8 wherein the second linker is comprised of at least 20 amino acid residues.

ASPECT 10. The recombinant DNA molecule of aspect 9 wherein the first and second linkers are comprised of at least about 80 percent glycine, alanine or serine residues.

ASPECT 11. The recombinant DNA molecule of aspect 1 wherein the peptide ligand segment comprises an antigenic peptide.

ASPECT 12. The recombinant DNA molecule of aspect 11 wherein the peptide ligand segment contains from about 4 to 30 amino acid residues.

ASPECT 13. The recombinant DNA molecule of aspect 12 wherein the peptide ligand segment contains from about 6 to 20 amino acid residues.

ASPECT 14. The recombinant DNA molecule of aspect 13 wherein the peptide ligand segment contains from about 8 to 12 amino acid residues.

ASPECT 15. The recombinant DNA molecule as claimed in aspect 1, wherein the DNA sequence is contained in a vector.

ASPECT 16. A host transformed with the vector of aspect 15.

ASPECT 17. A recombinant DNA molecule comprising a DNA sequence encoding a single chain trimer of a mature MHC molecule, the single chain trimer comprising in sequence:
(1) an antigenic peptide ligand segment containing from about 4 to 30 amino acid residues;
(2) a first linker comprising at least 10 amino acid residues;
(3) a β2m segment;
(4) a second linker comprising at least 15 amino acid residues; and
(5) a heavy chain segment comprising an HLA-A, HLA-B, HLA-C, 1a, 1b, H-2-K, H-2-Dd or H-2-Ld heavy chain,
wherein the peptide ligand segment has a carboxy end, the β2m segment has amino and carboxy ends, and the heavy chain segment has an amino end, and wherein the peptide ligand segment is covalently linked via its carboxy end to the amino end of the β2m segment by the first linker, and wherein the β2m segment is covalently linked via its carboxy end to the amino end of the heavy chain segment by the second linker.

ASPECT 18. The recombinant DNA molecule of aspect 17 wherein the class I heavy chain segment contains a mutated conserved residue.

ASPECT 19. The recombinant DNA molecule of aspect 18 wherein a tyrosine at position 84 is mutated.

ASPECT 20. The recombinant DNA molecule of aspect 17 wherein the first linker comprises at least 15 amino acid residues and the second linker comprises at least 20 amino acid residues.

ASPECT 21. The recombinant DNA molecule of aspect 17 wherein the peptide ligand segment contains from about 8 to 12 amino acid residues.

ASPECT 22. A class I heavy chain containing a mutated conserved residue.

ASPECT 23. The class I heavy chain of aspect 22 wherein the tyrosine at position 84 is mutated.

ASPECT 24. The recombinant DNA molecule as aspected in aspect 17, wherein the DNA sequence is contained in a vector.

ASPECT 25. A host transformed with the vector of aspect 24.

ASPECT 26. A single chain trimer of a mature Class I MHC molecule comprising
(1) a peptide ligand segment having a carboxy end;
(2) a first linker;
(3) a β2m segment having amino and carboxy ends;
(4) a second linker; and
(5) a class I heavy chain segment having an amino end, wherein the β2m segment and the heavy chain segment are encoded by a mammalian Class I MHC locus, wherein the carboxy end of the peptide ligand segment is covalently linked to the amino end of the β2m segment via a first flexible peptide linker, and wherein the carboxy end of the β2m segment is covalently linked to the amino end of the class I heavy chain segment via a second flexible peptide linker.

ASPECT 27. The single chain trimer of aspect 26 wherein the class I heavy chain segment is comprised of an HLA-A, HLA-B, HLA-C, 1a, 1b, H-2-K, H-2-Dd or H-2-Ld heavy chain.

ASPECT 28. The single chain trimer of aspect 26 wherein the class I heavy chain segment contains a mutated conserved residue.

ASPECT 29. The single chain trimer of aspect 28 wherein the tyrosine at position 84 is mutated.

ASPECT 30. The single chain trimer of aspect 26 wherein the first linker comprises at least 10 amino acid residues.

ASPECT 31. The single chain trimer of aspect 30 wherein the first linker comprises at least 15 amino acid residues.

ASPECT 32. The single chain trimer of aspect 31 wherein at least about 80 percent of the linkers comprise glycine, alanine or serine residues.

ASPECT 33. The single chain trimer of aspect 32 wherein the second linker comprises at least 15 amino acid residues.

ASPECT 34. The single chain trimer of aspect 33 wherein the second linker comprises at least 20 amino acid residues.

ASPECT 35. The single chain trimer of aspect 34 wherein at least about 80 percent of the linkers comprise glycine, alanine or serine residues.

ASPECT 36. The single chain trimer of aspect 26 wherein the peptide ligand comprises an antigenic peptide.

ASPECT 37. The single chain trimer of aspect 36 wherein the peptide ligand contains from about 4 to 30 amino acid residues.

ASPECT 38. The single chain trimer of aspect 37 wherein the peptide ligand contains from about 6 to 20 amino acid residues.

ASPECT 39. The single chain trimer of aspect 38 wherein the peptide ligand contains from about 8 to 12 amino acid residues.

ASPECT 40. A single chain trimer of a mature Class I MHC molecule comprising:
(1) an antigenic peptide ligand segment containing from about 4 to 30 amino acid residues and having a carboxy end
(2) a first linker comprising at least 10 amino acid residues;
(3) a β2m segment having amino and carboxy ends;
(4) a second linker comprising at least 10 amino acid residues; and
(5) a heavy chain segment comprising an HLA-A, HLA-B, HLA-C, 1a, 1b, H-2-K, H-2-Dd, and H-2-Ld heavy chain having an amino end, wherein the β2m segment and the heavy chain segment are encoded by a mammalian Class I MHC locus, wherein the carboxy end of the peptide ligand segment is covalently linked to the amino end of the β2m segment via a first flexible peptide linker, and wherein the carboxy end of the β2m segment is covalently linked to the amino end of the class I heavy chain segment via a second flexible peptide linker.

ASPECT 41. The single chain trimer of aspect 40 wherein the class I heavy chain segment contains a mutated conserved residue.

ASPECT 42. The single chain trimer of aspect 41 wherein a tyrosine at position 84 is mutated.

ASPECT 43. The single chain trimer of aspect 42 wherein the first linker comprises at least 15 amino acids and the second linker comprises at least 15 amino acids.

ASPECT 44. The single chain trimer of aspect 40 wherein the peptide ligand contains from about 8 to 12 amino acid residues.

ASPECT 45. A mutein of a class I heavy chain molecule having an amino acid other than tyrosine substituted at position 84.

ASPECT 46. A composition comprising an antigen bound to a single chain trimer of a mature Class I MHC molecule, the single chain trimer comprising:
(1) a peptide ligand segment having a carboxy end;
(2) a first linker;
(3) a β2m segment having amino and carboxy ends;
(4) a second linker; and
(5) a class I heavy chain segment having an amino end, wherein the β2m segment and the heavy chain segment are encoded by a mammalian Class I MHC locus, wherein the carboxy end of the peptide ligand segment is covalently linked to the amino end of the β2m segment via a first flexible peptide linker, and wherein the carboxy end of the β2m segment is covalently linked to the amino end of the class I heavy chain segment via a second flexible peptide linker.

ASPECT 47. The composition in accordance with aspect 46 wherein the antigen is a lymphocyte receptor.

ASPECT 48. The composition in accordance with aspect 47 wherein the lymphocyte receptor is a CD4+ or and CD8+ receptor.

ASPECT 49. An immunogenically effective composition comprising a single chain trimer of a mature Class I MHC molecule, the single chain trimer comprising:
(1) a peptide ligand segment having a carboxy end;
(2) a first linker;
(3) a β2m segment having amino and carboxy ends;
(4) a second linker; and
(5) a class I heavy chain segment having an amino end, wherein the β2m segment and the heavy chain segment are encoded by a mammalian Class I MHC locus, wherein the carboxy end of the peptide ligand segment is covalently linked to the amino end of the β2m segment via a first flexible peptide linker, and wherein the carboxy end of the β2m segment is covalently linked to the amino end of the class I heavy chain segment via a second flexible peptide linker and a physiologically acceptable carrier.

ASPECT 50. An immunogenically effective composition comprising an antigen bound to a single chain trimer of a mature Class I MHC molecule, the single chain trimer comprising:
(1) a peptide ligand segment having a carboxy end;
(2) a first linker;
(3) a β2m segment having amino and carboxy ends;
(4) a second linker; and
(5) a class I heavy chain segment having an amino end, wherein the β2m segment and the heavy chain segment are encoded by a mammalian Class I MHC locus, wherein the carboxy end of the peptide ligand segment is covalently linked to the amino end of the β2m segment via a first flexible peptide linker, and wherein the carboxy end of the β2m segment is covalently linked to the amino end of the class I heavy chain segment via a second flexible peptide linker and a physiologically acceptable carrier.

ASPECT 51. The immunogenically effective composition in accordance with aspect 50 wherein the antigen is a lymphocyte receptor.

ASPECT 52. The immunogenically effective composition in accordance with aspect 51 wherein the lymphocyte receptor is a CD4+ or and CD8+ receptor.

ASPECT 53. A method of eliciting an immune response in a mammal comprising administering to the mammal an effective amount of a single chain trimer of a mature Class I MHC molecule, the single chain trimer comprising:
(1) a peptide ligand segment having a carboxy end;
(2) a first linker;
(3) a β2m segment having amino and carboxy ends;
(4) a second linker; and
(5) a class I heavy chain segment having an amino end, wherein the β2m segment and the heavy chain segment are encoded by a mammalian Class I MHC locus, wherein the carboxy end of the peptide ligand segment is covalently linked to the amino end of the β2m segment via a first flexible peptide linker, and wherein the carboxy end of the β2m segment is covalently linked to the amino end of the class I heavy chain segment via a second flexible peptide linker.

ASPECT 54. The method in accordance with aspect 53 wherein the mammal suffers from a T-cell mediated autoimmune disease.

ASPECT 55. The method in accordance with aspect 53 wherein the T-cell mediated autoimmune disease is thyroiditis or multiple sclerosis.

ASPECT 56. The method in accordance with aspect 53 wherein the mammal suffers from a bacterial or a viral infection.

ASPECT 57. The method in accordance with aspect 53 wherein the mammal suffers from cancer.

ASPECT 58. A method of eliciting an immune response in a mammal comprising: administering to the mammal an effective amount of composition comprising an antigen bound to a single chain trimer of a mature Class I MHC molecule, the single chain trimer comprising
  (1) a peptide ligand segment having a carboxy end;
  (2) a first linker;
  (3) a β2m segment having amino and carboxy ends;
  (4) a second linker; and
  (5) a class I heavy chain segment having an amino end, wherein the β2m segment and the heavy chain segment are encoded by a mammalian Class I MHC locus, wherein the carboxy end of the peptide ligand segment is covalently linked to the amino end of the β2m segment via a first flexible peptide linker, and wherein the carboxy end of the β2m segment is covalently linked to the amino end of the class I heavy chain segment via a second flexible peptide linker.

ASPECT 59. The method in accordance with aspect 58 wherein the mammal suffers from a T-cell mediated autoimmune disease.

ASPECT 60. The method in accordance with aspect 58 wherein the T-cell mediated autoimmune disease is thyroiditis or multiple sclerosis.

ASPECT 61. The method in accordance with aspect 58 wherein the mammal suffers from a bacterial or a viral infection.

ASPECT 62. The method in accordance with aspect 58 wherein the mammal suffers from cancer.

ASPECT 63. A method of vaccinating a mammal comprising administering to the mammal an effective amount of a single chain trimer of a mature Class I MHC molecule, the single chain trimer comprising:
  (1) a peptide ligand segment having a carboxy end;
  (2) a first linker;
  (3) a β2m segment having amino and carboxy ends;
  (4) a second linker; and
  (5) a class I heavy chain segment having an amino end, wherein the β2m segment and the heavy chain segment are encoded by a mammalian Class I MHC locus, wherein the carboxy end of the peptide ligand segment is covalently linked to the amino end of the β2m segment via a first flexible peptide linker, and wherein the carboxy end of the β2m segment is covalently linked to the amino end of the class I heavy chain segment via a second flexible peptide linker.

ASPECT 64. The method in accordance with aspect 63 wherein the single chain trimer is administered by an oral, a respiratory or a parenteral routes.

ASPECT 65. The method in accordance with aspect 63 wherein the single chain trimer is administered by an intradermal, a subcutaneous or an intramuscular route.

ASPECT 66. A method of vaccinating a mammal comprising administering to the mammal an effective amount of a composition comprising an antigen bound to a single chain trimer of a mature Class I MHC molecule, the single chain trimer comprising:
  (1) a peptide ligand segment having a carboxy end;
  (2) a first linker;
  (3) a β2m segment having amino and carboxy ends;
  (4) a second linker; and
  (5) a class I heavy chain segment having an amino end, wherein the β2m segment and the heavy chain segment are encoded by a mammalian Class I MHC locus, wherein the carboxy end of the peptide ligand segment is covalently linked to the amino end of the β2m segment via a first flexible peptide linker, and wherein the carboxy end of the β2m segment is covalently linked to the amino end of the class I heavy chain segment via a second flexible peptide linker.

ASPECT 67. The method in accordance with aspect 66 wherein the single chain trimer is administered by an oral, a respiratory or a parenteral routes ASPECT 68. The method in accordance with aspect 66 wherein the single chain trimer is administered by an intradermal, a subcutaneous or an intramuscular route.

ASPECT 69. An antibody which binds to a single chain trimer of a mature Class I MHC molecule, the single chain trimer comprising:
  (1) a peptide ligand segment having a carboxy end;
  (2) a first linker;
  (3) a β2m segment having amino and carboxy ends;
  (4) a second linker; and
  (5) a class I heavy chain segment having an amino end, wherein the β2m segment and the heavy chain segment are encoded by a mammalian Class I MHC locus, wherein the carboxy end of the peptide ligand segment is covalently linked to the amino end of the β2m segment via a first flexible peptide linker, and wherein the carboxy end of the β2m segment is covalently linked to the amino end of the class I heavy chain segment via a second flexible peptide linker.

ASPECT 70. The antibody in accordance with aspect 69, which is a monoclonal antibody.

ASPECT 71. The antibody in accordance with aspect 69, which is a polyclonal antibody.

ASPECT 72. An antibody which binds to a composition comprising an antigen bound to a single chain trimer of a mature Class I MHC molecule, the single chain trimer comprising:
  (1) a peptide ligand segment having a carboxy end;
  (2) a first linker;
  (3) a β2m segment having amino and carboxy ends;
  (4) a second linker; and
  (5) a class I heavy chain segment having an amino end, wherein the β2m segment and the heavy chain segment are encoded by a mammalian Class I MHC locus, wherein the carboxy end of the peptide ligand segment is covalently linked to the amino end of the β2m segment via a first flexible peptide linker, and wherein the carboxy end of the β2m segment is covalently linked to the amino end of the class I heavy chain segment via a second flexible peptide linker.

ASPECT 73. The antibody in accordance with aspect 72, which is a monoclonal antibody.

ASPECT 74. The antibody in accordance with aspect 72, which is a polyclonal antibody.

ASPECT 75. A method of detecting MHC gene products in biological preparations comprising:
  (a) contacting a biological preparation with the antibody of aspect 69 under conditions allowing the antibody to bind the MHC gene product; and
  (b) detecting the presence of the thus bound MHC gene product.

ASPECT 76. A composition comprising the antibody of aspect 69 and a pharmaceutically acceptable carrier.

ASPECT 77. The antibody of aspect 69 which is labeled.

ASPECT 78. The antibody of aspect 77 wherein the label is selected from the group consisting of enzymes, radioisotopes, fluorescent compounds, chemiluminescent compounds, bioluminescent compounds, and metal chelates.

ASPECT 79. A hybridoma that produces the antibody of aspect 69.

ASPECT 80. A method of detecting MHC gene products in biological preparations comprising:
(a) contacting a biological preparation with the antibody of aspect 72 under conditions allowing the antibody to bind the MHC gene product; and
(b) detecting the presence of the thus bound MHC gene product.

ASPECT 81. A composition comprising the antibody of aspect 72 and a pharmaceutically acceptable carrier.

ASPECT 82. The antibody of aspect 72 which is labeled.

ASPECT 83 The antibody of aspect 82 wherein the label is selected from the group consisting of enzymes, radioisotopes, fluorescent compounds, chemiluminescent compounds, bioluminescent compounds, and metal chelates.

ASPECT 84 A hybridoma that produces the antibody or fragment thereof of aspect 72.

ASPECT 85. A method of eliciting an immune response in a mammal comprising vaccinating a mammal with a recombinant DNA molecule encoding a single chain trimer of a mature Class I MHC molecule comprising:
(1) an antigenic peptide ligand segment containing from about 4 to 30 amino acid residues and having a carboxy end;
(2) a first linker comprising at least 10 amino acid residues;
(3) a β2m segment having amino and carboxy ends;
(4) a second linker comprising at least 10 amino acid residues; and
(5) a heavy chain segment encoded by an MHC class I gene or class I like gene, wherein the carboxy end of the peptide ligand segment is covalently linked to the amino end of the β2m segment via a first flexible peptide linker, and wherein the carboxy end of the β2m segment is covalently linked to the amino end of the class I heavy chain segment via a second flexible peptide linker.

ASPECT 86. A method of aspect 85 wherein the recombinant DNA molecule elicits an immune response against a tumor.

ASPECT 87. A method of aspect 85 wherein the recombinant DNA molecule elicits an immune response against a virus.

ASPECT 89. The method of aspects 86, 87, or 88 wherein the immune response is selected from the group consisting of T cell mediated and B cell mediated.

ASPECT 90. A method of obtaining antibodies against class I/peptide ligand complexes comprising;
a) vaccinating a mammal with a recombinant DNA molecule encoding a single chain trimer of a mature Class I MHC molecule comprising:
(1) an antigenic peptide ligand segment containing from about 4 to 30 amino acid residues and having a carboxy end;
(2) a first linker comprising at least 10 amino acid residues;
(3) a β2m segment having amino and carboxy ends;
(4) a second linker comprising at least 10 amino acid residues; and
(5) a heavy chain segment from an MHC class I gene or class I like gene, wherein the carboxy end of the peptide ligand segment is covalently linked to the amino end of the β2m segment via a first flexible peptide linker, and wherein the carboxy end of the β2m segment is covalently linked to the amino end of the class I heavy chain segment via a second flexible peptide linker.

ASPECT 91. A single chain trimer molecule comprising, in amino-to-carboxy terminal order, an antigen peptide sequence, a β2-microglobulin sequence, and a human MHC class I heavy chain sequence.

ASPECT 92. A single chain trimer molecule in accordance with aspect 91, wherein the antigen peptide sequence comprises from about 8 amino acids up to about 13 contiguous amino acid residues.

ASPECT 93. A single chain trimer molecule in accordance with aspect 91, wherein the antigen peptide sequence comprises 9 contiguous amino acids.

ASPECT 94. A single chain trimer molecule in accordance with aspect 91, wherein the antigen peptide sequence comprises a sequence selected from the group consisting of NLVPMVATV (SEQ ID NO: 1), GLCTLVAML (SEQ ID NO: 2), GILGFVFTL (SEQ ID NO: 3); IMDQVPFSV (SEQ ID NO: 4) and YLEPGPVTV (SEQ ID NO: 5).

ASPECT 95. A single chain trimer molecule in accordance with aspect 91, wherein the β2-microglobulin sequence is a human β2-microglobulin sequence.

ASPECT 96. A single chain trimer molecule in accordance with aspect 95, wherein the sequence of the human β2-microglobulin is set forth as SEQ ID NO: 6.

ASPECT 97. A single chain trimer molecule in accordance with aspect 91, wherein the human MHC class I heavy chain sequence is selected from the group consisting of an HLA-A MHC class I heavy chain sequence and an HLA-B MHC class I heavy chain sequence.

ASPECT 98. A single chain trimer molecule in accordance with aspect 97, wherein the HLA-A MHC class I heavy chain sequence is an HLA-A*0201 MHC class I heavy chain sequence.

ASPECT 99. A single chain trimer molecule in accordance with aspect 91, wherein the MHC class I heavy chain sequence is a human MHC class I heavy chain sequence consisting of the sequence set forth as SEQ ID NO: 7.

ASPECT 100. A single chain trimer molecule in accordance with aspect 91, wherein the MHC class I heavy chain sequence is a human MHC class I heavy chain sequence consisting of the sequence set forth as SEQ ID NO: 8, wherein the amino acid at position 84 is a non-aromatic amino acid other than proline.

ASPECT 101. A single chain trimer in accordance with aspect 91, wherein the human MHC class I heavy chain comprises the sequence set forth as SEQ ID NO: 9.

ASPECT 102. A single chain trimer molecule in accordance with aspect 91, further comprising a leader peptide sequence.

ASPECT 103. A single chain trimer molecule in accordance with aspect 102, wherein the leader peptide sequence comprises about 20 contiguous amino acids comprised by the amino terminal sequence of a β2-microglobulin.

ASPECT 104. A single chain trimer molecule in accordance with aspect 103, wherein the leader peptide sequence comprises the sequence set forth as SEQ ID NO: 10.

ASPECT 105. A single chain trimer molecule in accordance with aspect 91, further comprising a first linker sequence extending between the antigen peptide sequence and the β2-microglobulin sequence.

ASPECT 106. A single chain trimer molecule in accordance with aspect 105, wherein the first linker sequence comprises at least about 10 amino acids up to about 15 amino acids.

ASPECT 107. A single chain trimer molecule in accordance with aspect 105, wherein at least about 80 percent of the amino acids comprising the first linker are glycines.

ASPECT 108. A single chain trimer molecule in accordance with aspect 105, wherein the first linker comprises a sequence selected from the group consisting of SEQ ID NO: 11, SEQ ID NO: 12 and SEQ ID NO: 13.

ASPECT 109. A single chain trimer molecule in accordance with aspect 91, further comprising a second linker sequence extending between the β2-microglobulin sequence and the MHC class I heavy chain sequence.

ASPECT 110. A single chain trimer molecule in accordance with aspect 109, wherein the second linker sequence comprises at least about 15 amino acids up to about 20 amino acids.

ASPECT 111. A single chain trimer molecule in accordance with aspect 109, wherein at least about 80 percent of the amino acids comprising the second linker are glycines.

ASPECT 112. A single chain trimer molecule in accordance with aspect 109, wherein the second linker comprises a sequence selected from the group consisting of SEQ ID NO: 13 and SEQ ID NO: 14.

ASPECT 113. A single chain trimer molecule in accordance with aspect 91, wherein the molecule comprises, in amino-to-carboxy terminal order, an antigen peptide sequence, a first linker sequence, a β2-microglobulin sequence, a second linker sequence, and an MHC class I heavy chain sequence.

ASPECT 114. A single chain trimer molecule in accordance with aspect 91, wherein the molecule has a sequence selected from the group consisting of SEQ ID NO: 15, SEQ ID NO: 16 and SEQ ID NO: 17.

ASPECT 115. A cell comprising the single chain trimer molecule of aspect 91.

ASPECT 116. A cell in accordance with aspect 115, wherein the cell is an antigen presenting cell.

ASPECT 117. A cell in accordance with aspect 116, wherein the antigen presenting cell is selected from the group consisting of a dendritic cell, a B cell and a macrophage.

ASPECT 118. A nucleic acid comprising a sequence encoding a single chain trimer molecule of aspect 91.

ASPECT 119. A nucleic acid in accordance with aspect 118, wherein the antigen peptide sequence comprises a sequence selected from the group consisting of NLVPMVATV (SEQ ID NO: 1), GLCTLVAML (SEQ ID NO: 2), GILGFVFTL (SEQ ID NO: 3); IMDQVPFSV (SEQ ID NO: 4) and YLEPGPVTV (SEQ ID NO: 5).

ASPECT 120. A vector comprising a promoter operably linked to the sequence encoding a single chain trimer molecule of aspect 118.

ASPECT 121. A cell comprising the nucleic acid of aspect 118.

ASPECT 122. A cell in accordance with aspect 121, wherein the cell is an antigen presenting cell.

ASPECT 123. A method of expanding a population of antigen-specific CD8$^+$ T cells ex vivo, the method comprising:
a) co-culturing, in a first culture, a population of antigen-specific CD8$^+$ T cells with a first population of antigen presenting cells comprising an MHC antigen peptide; and
b) co-culturing, in a second culture, the population of antigen-specific CD8$^+$ T cells with a population of cells comprising a single chain trimer of aspect 1, wherein the single chain trimer comprises a segment comprising the sequence of the MHC antigen peptide, a segment comprising a human β2-microglobulin sequence, and a segment comprising a human MHC class I heavy chain sequence.

ASPECT 124. A method in accordance with aspect 123, wherein the first population of antigen presenting cells are selected from the group consisting of dendritic cells, B cells, macrophages and a combination thereof ASPECT 125. A method in accordance with aspect 123, wherein the first population of antigen presenting cells are dendritic cells.

ASPECT 126. A method in accordance with aspect 123, wherein the population of cells comprising the single chain trimer comprise a second population of antigen presenting cells.

ASPECT 127. A method in accordance with aspect 123, wherein the second population of antigen presenting cells are selected from the group consisting of K562 cells, dendritic cells, B cells, macrophages and a combination thereof ASPECT 128. A method in accordance with aspect 127, wherein the second population of antigen presenting cells are K562 cells.

ASPECT 129. A method in accordance with aspect 123, wherein the MHC class I heavy chain sequence is an HLA-A*0201 sequence.

ASPECT 130. A method in accordance with aspect 123, wherein the antigen peptide sequence comprises at least about 8 contiguous amino acids up to about 13 contiguous amino acids.

ASPECT 131. A method in accordance with aspect 130, wherein the antigen peptide sequence consists of 9 contiguous amino acids.

ASPECT 132. A method in accordance with aspect 123, wherein the antigen peptide sequence comprises an amino acid sequence identical to a sequence selected from the group consisting of an antigen peptide sequence comprised by a cell infected with a viral pathogen, a bacterial pathogen, or a combination thereof ASPECT 133. A method in accordance with aspect 132, wherein the MHC antigen peptide sequence is selected from the group consisting of NLVPMVATV (SEQ ID NO: 1), GLCTLVAML (SEQ ID NO: 2) and GILGFVFTL (SEQ ID NO: 3).

ASPECT 134. A method in accordance with aspect 123, wherein the MHC antigen peptide sequence comprises an amino acid sequence identical to an MHC antigen sequence of a protein comprised by a cell of a cancer selected from the group consisting of melanoma, glioma, lung carcinoma, prostate carcinoma, breast carcinoma, colon carcinoma, leukemia, lymphoma, myeloma, and pancreatic carcinoma.

ASPECT 135. A method in accordance with aspect 134, wherein the MHC antigen peptide sequence is selected from the group consisting of IMDQVPFSV (SEQ ID NO: 4) and YLEPGPVTV (SEQ ID NO: 5).

ASPECT 136. A method in accordance with aspect with aspect 123, wherein the antigen-specific CD8$^+$ T cells are autologous to a patient in need of adoptive T cell immunotherapy.

ASPECT 137. A method in accordance with aspect 123, wherein the first population of antigen presenting cells are autologous to a patient in need of adoptive T cell immunotherapy.

ASPECT 138. A method in accordance with aspect 123, wherein the expanding comprises obtaining about 1×10$^9$ of the antigen-specific CD8$^+$ T cells in less than about two months after initiating the co-culturing of the antigen-specific CD8$^+$ T cells with the first population of antigen presenting cells.

ASPECT 139. A method in accordance with aspect 123, wherein the expanding comprises obtaining at least about 1×10$^9$ of the antigen-specific CD8$^+$ T cells within about 28

ASPECT 140. A method in accordance with aspect 123, wherein expanding the population of antigen-specific CD8+ T cells comprises expanding the population at least about 10,000 fold in less than about 2 months after initiating the co-culturing of the antigen-specific CD8+ T cells with the first population of antigen presenting cells.

ASPECT 141. A method in accordance with aspect 123, wherein expanding the population of antigen-specific CD8+ T cells comprises expanding the population at least about 100,000 fold within about 28 days after initiating the co-culturing of the antigen-specific CD8+ T cells with the first population of antigen presenting cells.

ASPECT 142. A method in accordance with aspect 123, wherein the co-culturing the population of antigen-specific CD8+ T cells with the first population of antigen presenting cells in a first culture comprises co-culturing for about 14 days.

ASPECT 143. A method in accordance with aspect 123, wherein the co-culturing the population of antigen-specific CD8+ T cells with a population of cells comprising a single chain trimer comprising the MHC antigen peptide sequence in a second culture comprises co-culturing for about 14 days.

ASPECT 144. A method in accordance with aspect 123, wherein the population of cells comprising a single chain trimer comprise cells are comprising a nucleic acid encoding the single chain trimer, wherein the cells express the single chain trimer.

ASPECT 145. A method in accordance with aspect 123, wherein the cells comprising the single chain trimer are human hematopoietic cells expressing the single chain trimer.

ASPECT 146. A method in accordance with aspect 144, wherein the human hematopoietic cells expressing the single chain trimer are K-562 cells comprising a nucleic acid encoding the single chain trimer.

ASPECT 147. A method in accordance with aspect 123, wherein the population of antigen-specific CD8+ T cells following the expanding is at least about 55% pure.

ASPECT 148. A method in accordance with aspect 123, wherein the population of antigen-specific CD8+ T cells following the expanding are at least about 95% pure.

ASPECT 149. A method in accordance with aspect 123, wherein the population of antigen-specific CD8+ T cells following the expanding comprises at least about $1.1 \times 10^5$ fold increase in Tetramer-positive cells.

ASPECT 150. A method in accordance with aspect 123, wherein the population of antigen-specific CD8+ T cells following the expanding comprise at least about $4.1 \times 10^6$ fold increase in Tetramer-positive cells.

ASPECT 151. A method of treating infection in a human subject, the method comprising:
expanding a population of antigen-specific CD8+ T cells autologous to a human subject in need of treatment of a pathogen infection in accordance with the method of aspect 123; and
administering the expanded population to the human subject.

ASPECT 152. A method of treating cancer in a human subject, the method comprising:
expanding a population of antigen-specific CD8+ T cells autologous to a human subject in need of treatment of a cancer in accordance with the method of aspect 123; and
administering the expanded population to the human subject.

What is claimed is:

1. A method of expanding a population of antigen-specific CD8+ T cells ex vivo, the method comprising:
   establishing a first culture comprising a population of antigen-specific CD8+ T cells, a first population of antigen presenting cells comprising an MHC antigen peptide and a culture medium comprising IL-7;
   co-culturing the first culture for no greater than 14 days, wherein IL-2 is added to the first culture every 2-4 days; and
   subsequently establishing a second culture comprising the population of antigen-specific CD8+ T cells, a population of cells comprising a single chain trimer and a culture medium comprising IL-2;
   co-culturing the second culture for about 14 days, wherein the single chain trimer comprises, in amino-to-carboxy terminal order, a segment comprising the sequence of the MHC antigen peptide, a segment comprising a human β2-microglobulin sequence, and a segment comprising a human MHC class I heavy chain sequence.

2. A method in accordance with claim 1, wherein the first population of antigen presenting cells is selected from the group consisting of dendritic cells, B cells, macrophages and a combination thereof.

3. A method in accordance with claim 1, wherein the population of cells comprising the single chain trimer is a population of antigen presenting cells expressing the single chain trimer.

4. A method in accordance with claim 3, wherein the population of antigen presenting cells expressing the single chain trimer is a population of human hematopoietic cells expressing the single chain trimer.

5. A method in accordance with claim 1, wherein the MHC antigen peptide comprises a sequence selected from the group consisting of NLVPMVATV (SEQ ID NO: 1), GLCTLVAML (SEQ ID NO: 2), GILGFVFTL (SEQ ID NO: 3), IMDQVPFSV (SEQ ID NO: 4) and YLEPGPVTV (SEQ ID NO: 5).

6. A method in accordance with claim 1, wherein expanding the population of antigen-specific CD8+ T cells comprises obtaining about $1 \times 10^9$ of the antigen-specific CD8+ T cells.

7. A method in accordance with claim 1, wherein expanding the population of antigen-specific CD8+ T cells comprises expanding the population at least about 10,000 fold.

8. A method in accordance with claim 1, wherein expanding the population of antigen-specific CD8+ T cells comprises expanding the population at least about 100,000 fold.

9. A method in accordance with claim 1, wherein the population of antigen-specific CD8+ T cells following the expanding is at least about 55% pure.

10. A method in accordance with claim 1, wherein the population of antigen-specific CD8+ T cells following the expanding is at least about 95% pure.

11. A method in accordance with claim 1, wherein the population of antigen-specific CD8+ T cells following the expanding comprises at least about $1.1 \times 10^5$ fold increase in tetramer-positive cells.

12. A method in accordance with claim 1, wherein the population of antigen-specific CD8+ T cells following the expanding comprises at least about $4.1 \times 10^6$ fold increase in tetramer-positive cells.

* * * * *